United States Patent
Carroll et al.

(10) Patent No.: US 6,191,140 B1
(45) Date of Patent: Feb. 20, 2001

(54) PYRANO, PIPERIDINO, AND THIOPYRANO COMPOUNDS AND METHODS OF USE

(75) Inventors: William A. Carroll, Evanston; Konstantinos A. Agrios; Robert J. Altenbach, both of Chicago; Irene Drizin, Wadsworth; Michael E. Kort, Lake Bluff, all of IL (US)

(73) Assignee: Abbott Laboratories, Abbott Park, IL (US)

(*) Notice: Under 35 U.S.C. 154(b), the term of this patent shall be extended for 0 days.

(21) Appl. No.: 09/421,862

(22) Filed: Oct. 20, 1999

Related U.S. Application Data

(63) Continuation-in-part of application No. 09/181,690, filed on Oct. 28, 1998, now abandoned.

(51) Int. Cl.[7] .......................... A61K 31/44; A61K 31/55; C07D 513/00; C07D 491/00; C07D 219/00
(52) U.S. Cl. ................ 514/297; 514/211.1; 514/211.11; 514/215; 514/222.8; 514/291; 514/293; 540/578; 540/580; 544/34; 546/81; 546/82; 546/83; 546/89; 546/90; 546/93; 546/102
(58) Field of Search .......................... 514/211.1, 211.11, 514/215, 222.8, 291, 293, 297; 540/578, 580; 544/34; 546/81, 82, 83, 89, 90, 93, 102

(56) References Cited

U.S. PATENT DOCUMENTS

| | | |
|---|---|---|
| 4,321,384 | 3/1982 | Sulkowski et al. . |
| 4,551,534 | 11/1985 | Sulkowski et al. . |
| 4,596,873 | 6/1986 | Sulkowski et al. . |
| 4,618,678 | 10/1986 | Sulkowski et al. . |

FOREIGN PATENT DOCUMENTS

| | | |
|---|---|---|
| 0059291 | 9/1982 | (EP) . |
| 0211584 | 2/1987 | (EP) . |
| 0539153 | 4/1993 | (EP) . |
| 0539154 | 4/1993 | (EP) . |
| 9408966 | 4/1994 | (WO) . |
| 9602547 | 2/1996 | (WO) . |
| 9931059 | 6/1999 | (WO) . |

OTHER PUBLICATIONS

Berge, S. M., et al., "Pharmaceutical Salts", *Journal of Pharma. Sci.*, 66(1):1–19 (1977).
Dodd, J. H., et al., "Synthesis of Novel Cyclic Sulfone Dihydropyridines Facilitated by a Selective Ethyl Diazoacetate Ring Expansion", *J. Heterocyclic Chem.*, 27:1453–1456 (1990).
Freedman, J.E., et al., "ATP–sensitive Potassium Channels: Diverse Functions in the Central Nervous System", *The Neuroscientist*, 2(3):145–152 (1996).
Gehlert, D. R., et al., "ATP Sensitive Potassium Channels: Potential Drug Trgets in Neuropsychopharmacology", *Prog. Neuro–Psych. A. Biol. Psychiat.*, 18:1093–1102 (1994).

Gopalakrishnan, M., et al., "ATP_Sensitive K+ Channels: Pharmacologic Properties, Regulation, and Therapeutic Potential", *Drug Devel. Res.*, 28:95–127 (1993).
Howe, B. B., et al., "ZENECA AD6169: A Novel KATP Channel Opener with in Vivo Selectivity for Urinary Bladder", *The Journ. Of Pharmac. & Exp. Therap.*, 274():884–890 (1995).
Klockner. U., et al., Action potentials and net membrane currents of isolated smooth muscle cells (urinary bladder of the guinea–pig), *Pflugers Archiv*, 405:329–339 (1985).
Quast., U., et al., "Binding of the K+ Channel Opener {3H]P1075 in Rat Isolated Aorta: Relationship to Functional Effects of Openers and Blockers", *The Amer. Soc. For Pharma. & Exp. Terap.*, 43:474–481 (1993).
Lawson, K., "Potassium channel Activation: A Potential therapeutic Approach", *Pharmacol. Therap.*, 70(1):39–63 (1996).
Nurse, D. E., et al., "The Effect of Cromakallim on the Normal and Hyper–reflexic Human Detrusor Muscle", *British Journ. Of Urology* 68:27–31 (1991).
Silver, P. J., et al., "Wy–46,300 and Wy–46,531: Vascular Smooth Muscle Relaxant/Antihypertensive Agents with Combined CA2+ Antagonist/Myosin Phosphorylation Inhibitory Mechanism", *Journ of Cardio. Pharmacol.*, 8:1168–1175 (1986).
Spanswick, D., et al., "Leptin inhibits hypothalamic neurons by activation of ATP–sensitive postassium channels", *Letters to Nature*, 390:521–525 (1997).
Terasawa, T., et al., "Novel Heterocyclic Synthons, Synthesis and Properties of Thia– and Oxacyclohexane–3,5–diones", *J. Org. Chem.*, 42(7):1163–1169 (1977).
Ziegler, F. E., et al., "The Claisen Rearrangement in Indole Alkaloid Synthesis. The Total Syntheis of (±)–Tabersomine1", *Journ of the Amer. Chem. Soc.*, 95(22):7458–7463 (1973).
Frank, C. A., et al., "Dihydropyridine KATP potassium channel openers", *Chemical Abstracts*, 120(23):#289706— XP–002130833.
Jain, S. M., et al., "Synthesis and pharmacological screening of 1,8–dioxo–9–(substituted phenyl)–1,2,3,4,5,6,7,8,9, 10–decahydroacridines", *Chemical Abstracts*, 116(9):#84026—XP–002130834.
Tamura, et al., "Studies on 3,5–dioxopiperidines: novel and facile synthetic routes tol 3–amino–5–hydroxypyridine derivatives", *Chemical Abstracts*, 95(3):#24747— XP–002130835.

*Primary Examiner*—D. Margaret Seaman
(74) *Attorney, Agent, or Firm*—Michael J. Ward

(57) ABSTRACT

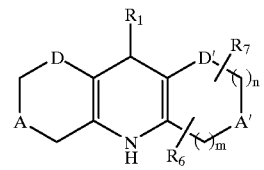

The present invention provides novel compounds of formula I which may be useful in hyperpolarizing cell membranes, opening potassium channels, relaxing smooth muscle cells, and inhibiting bladder contractions.

97 Claims, No Drawings

PYRANO, PIPERIDINO, AND THIOPYRANO COMPOUNDS AND METHODS OF USE

This application is a continuation-in-part of U.S. application Ser. No. 09/181,690, filed Oct. 28, 1998, ABN, incorporated herein by reference.

TECHNICAL FIELD

Novel dihydropyridine compounds and their derivatives can open potassium channels and are useful for treating a variety of medical conditions.

BACKGROUND OF INVENTION

Potassium channels play an important role in regulating cell membrane excitability. When the potassium channels open, changes in the electrical potential across the cell membrane occur and result in a more polarized state. A number of diseases or conditions can be treated with therapeutic agents that open potassium channels; see (K. Lawson, Pharmacol. Ther., v. 70, pp. 39–63 (1996)); (D. R. Gehlert et al., Prog. Neuro-Psychopharmacol & Biol. Psychiat., v. 18, pp. 1093–1102 (1994)); (M. Gopalakrishnan et al., Drug Development Research, v. 28, pp. 95–127 (1993)); (J. E. Freedman et al., The Neuroscientist, v. 2, pp. 145–152 (1996)); (D. E. Nurse et al., Br. J. Urol., v. 68 pp. 27–31 (1991)); (B. B. Howe et al., J. Pharmacol. Exp. Ther., v. 274 pp. 884–890 (1995)); and (D. Spanswick et al., Nature, v. 390 pp. 521–25 (Dec. 4, 1997)). Such diseases or conditions include asthma, epilepsy, hypertension, male sexual dysfunction, female sexual dysfunction, migraine, pain, urinary incontinence, stroke, Raynaud's Syndrome, eating disorders, functional bowel disorders, and neurodegeneration.

Potassium channel openers also act as smooth muscle relaxants. Because urinary incontinence can result from the spontaneous, uncontrolled contractions of the smooth muscle of the bladder, the ability of potassium channel openers to hyperpolarize bladder cells and relax bladder smooth muscle provides a method to ameliorate or prevent urinary incontinence.

Journal of Cardiovascular Pharmacology 8:1168–1175, (1986) Raven Press, New York, EP 0 059 291, EP 87051738, U.S. Pat. Nos. 4,321,384, 4,551,534, 4,596,873, and U.S. Pat No. 4,618,678 all disclose 4-(aryl)-4,5,6,7,8,-hexahydro-2-alkyl-5-oxo-1,7-naphthyridine-3-carboxylic esters as calcium entry blockers that may be useful as antihypertensive agents.

Compounds of the present Invention are novel, hyperpolarize cell membranes, open potassium channels, relax smooth muscle cells, inhibit bladder contractions and are useful for treating diseases that can be ameliorated by opening potassium channels.

SUMMARY OF THE INVENTION

In its principle embodiment of the present invention, compounds of the present invention have formula I or a pharmaceutically acceptable salt, amide, ester, or pro-drug thereof, wherein $n$ is 0-1;

$m$ is 1-2;

A is selected from the group consisting of $NR_2$, O, and S;

A' is selected from the group consisting of $NR_3$, O, S and $CR_4R_5$;

D is selected from the group consisting of $CH_2$ and $C(O)$;

D' is selected from the group consisting of $CH_2$, $C(O)$, $S(O)$, and $S(O)_2$;

$R_1$ is selected from the group consisting of aryl and heterocycle;

$R_2$ and $R_3$ are independently selected from the group consisting of hydrogen, alkoxyalkyl, alkyl, arylalkyl, cycloalkyl, cycloalkylalkyl, haloalkyl, heterocyclealkyl, hydroxy, hydroxyalkyl, $—NZ_1Z_2$, and $(NZ_1Z_2)$alkyl wherein $Z_1$ and $Z_2$ are independently selected from the group consisting of hydrogen, alkyl, alkylcarbonyl, aryl, arylalkyl, and formyl;

$R_4$ and $R_5$ are independently selected from the group consisting of hydrogen and alkyl;

$R_6$ and $R_7$ are independently selected from the group consisting of hydrogen and alkyl;

with the proviso that when D is $CH_2$ then D' is other than $CH_2$; and with the proviso that when D' is $S(O)$ or $S(O)_2$ then A' is $CR_4R_5$.

DETAILED DESCRIPTION OF THE INVENTION

All patents, patent applications, and literature references cited in the specification are herein incorporated by reference in their entirety. In the case of inconsistencies, the present disclosure, including definitions, will prevail.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

In its principle embodiment of the present invention, compounds of the present invention have formula I

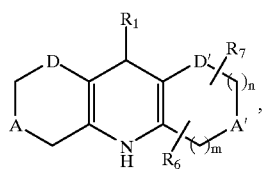

I or a pharmaceutically acceptable salt, amide, ester, or prodrug thereof, wherein n is 0-1;

m is 1-2;

A is selected from the group consisting of $NR_2$, O, and S;

A' is selected from the group consisting of $NR_3$, O, S and $CR_4R_5$;

D is selected from the group consisting of $CH_2$ and C(O);

D' is selected from the group consisting of $CH_2$, C(O), S(O), and $S(O)_2$;

$R_1$ is selected from the group consisting of aryl and heterocycle;

$R_2$ and $R_3$ are independently selected from the group consisting of hydrogen, alkoxyalkyl, alkyl, arylalkyl, cycloalkyl, cycloalkylalkyl, haloalkyl, heterocyclealkyl, hydroxy, hydroxyalkyl, —$NZ_1Z_2$, and ($NZ_1Z_2$)alkyl wherein $Z_1$ and $Z_2$ are independently selected from the group consisting of hydrogen, alkyl, alkylcarbonyl, aryl, arylalkyl, and formyl;

$R_4$ and $R_5$ are independently selected from the group consisting of hydrogen and alkyl;

$R_6$ and $R_7$ are independently selected from the group consisting of hydrogen and alkyl;

with the proviso that when D is $CH_2$ then D' is other than $CH_2$; and with the proviso that when D' is S(O) or $S(O)_2$ then A' is $CR_4R_5$.

In another embodiment, the present invention discloses compounds having formula II:

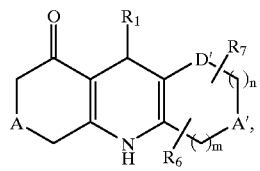

II or a pharmaceutically acceptable salt, ester, amide, or prodrug thereof wherein, A, A', D', $R_1$, $R_6$, $R_7$, m, and n are as defined in formula I.

In another embodiment of the present invention, compounds have formula II wherein, A is $NR_2$; and A', D', $R_1$, $R_2$, $R_6$, $R_7$, m, and n are as defined in formula I.

In another embodiment of the present invention, compounds have formula II wherein, A is O; and A', D', $R_1$, $R_6$, $R_7$, m, and n are as defined in formula I.

In another embodiment of the present invention, compounds have formula II wherein, A is S; and A', D', $R_1$, $R_6$, $R_7$, m, and n are as defined in formula I.

In another embodiment, the present invention discloses compounds having formula III:

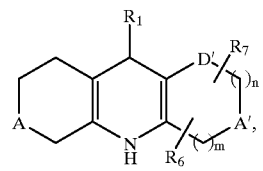

III or a pharmaceutically acceptable salt, ester, amide, or prodrug thereof wherein, A, A', D', $R_1$, $R_6$, $R_7$, m, and n are as defined in formula I with the proviso that D' is not $CH_2$.

In another embodiment of the present invention, compounds have formula III wherein, A is $NR_2$; and A', D', $R_1$, $R_2$, $R_6$, $R_7$, m, and n are as defined in formula I.

In another embodiment of the present invention, compounds have formula III wherein, A is O; and A', D', $R_1$, $R_6$, $R_7$, m, and n are as defined in formula I.

In another embodiment of the present invention, compounds have formula III wherein, A is S; and A', D', $R_1$, $R_6$, $R_7$, m, and n are as defined in formula I.

In another embodiment, the present invention discloses compounds having formula IV:

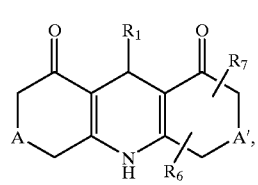

IV or a pharmaceutically acceptable salt, ester, amide, or prodrug thereof wherein, A, A', $R_1$, $R_6$, and $R_7$, are as defined in formula I.

In another embodiment of the present invention, compounds have formula IV wherein, A is $NR_2$; A' is $NR_3$; and $R_1$, $R_2$, $R_3$, $R_6$, and $R_7$ are as defined in formula I.

In another embodiment of the present invention, compounds have formula IV wherein, A is $NR_2$; A' is $NR_3$; $R_6$ is hydrogen; $R_7$ is hydrogen; and $R_1$, $R_2$, and $R_3$ are as defined in formula I.

In another embodiment of the present invention, compounds have formula IV wherein, A is $NR_2$; A' is O; and $R_1$, $R_2$, $R_6$, and $R_7$ are as defined in formula I.

In another embodiment of the present invention, compounds have formula IV wherein, A is $NR_2$; A' is S; and $R_1$, $R_2$, $R_6$, and $R_7$ are as defined in formula I.

In another embodiment of the present invention, compounds have formula IV wherein, A is O; A' is $NR_3$; and $R_1$, $R_3$, $R_6$, and $R_7$ are as defined in formula I.

In another embodiment of the present invention, compounds have formula IV wherein, A is O; A' is $NR_3$; $R_6$ is hydrogen; $R_7$ is hydrogen; and $R_1$ and $R_3$ are as defined in formula I.

In another embodiment of the present invention, compounds have formula IV wherein, A is O; A' is O; and $R_1$, $R_6$, and $R_7$ are as defined in formula I.

In another embodiment of the present invention, compounds have formula IV wherein, A is O; A' is O; $R_6$ is hydrogen; $R_7$ is hydrogen; and $R_1$ is as defined in formula I.

In another embodiment of the present invention, compounds have formula IV wherein, A is O; A' is S; and $R_1$, $R_6$, and $R_7$ are as defined in formula I.

In another embodiment of the present invention, compounds have formula IV wherein, A is O; A' is S; $R_6$ is hydrogen; $R_7$ is hydrogen; and $R_1$ is as defined in formula I.

In another embodiment of the present invention, compounds have formula IV wherein, A is S; A' is $NR_3$; and $R_1$, $R_3$, $R_6$, and $R_7$ are as defined in formula I.

In another embodiment of the present invention, compounds have formula IV wherein, A is S; A' is O; and $R_1$, $R_6$, and $R_7$ are as defined in formula I.

In another embodiment of the present invention, compounds have formula IV wherein, A is S; A' is S; and $R_1$, $R_6$, and $R_7$ are as defined in formula I.

In another embodiment, the present invention discloses compounds having formula V:

V or a pharmaceutically acceptable salt, ester, amide, or prodrug thereof wherein, A, A', $R_1$, $R_6$, and $R_7$, are as defined in formula I.

In another embodiment of the present invention, compounds have formula V wherein, A is $NR_2$; A' is $NR_3$; and $R_1$, $R_2$, $R_3$, $R_6$, and $R_7$ are as defined in formula I.

In another embodiment of the present invention, compounds have formula V wherein, A is $NR_2$; A' is O; and $R_1$, $R_2$, $R_6$, and $R_7$ are as defined in formula I.

In another embodiment of the present invention, compounds have formula V wherein, A is $NR_2$; A' is O; $R_6$ is hydrogen; $R_7$ is hydrogen; and $R_1$ and $R_2$ are as defined in formula I.

In another embodiment of the present invention, compounds have formula V wherein, A is $NR_2$; A' is S; and $R_1$, $R_2$; $R_6$, and $R_7$ are as defined in formula I.

In another embodiment of the present invention, compounds have formula V wherein, A is $NR_2$; A' is $CR_4R_5$; and $R_1$, $R_2$, $R_4$, $R_5$, $R_6$, and $R_7$ are as defined in formula I.

In another embodiment of the present invention, compounds have formula V wherein, A is $NR_2$; A' is $CR_4R_5$; $R_4$ is hydrogen; $R_5$ is hydrogen; $R_6$ is hydrogen; $R_7$ is hydrogen; and $R_1$ and $R_2$ are as defined in formula I.

In another embodiment of the present invention, compounds have formula V wherein, A is O; A' is $NR_3$; and $R_1$, $R_3$, $R_6$, and $R_7$ are as defined in formula I.

In another embodiment of the present invention, compounds have formula V wherein, A is O; A' is $NR_3$; $R_6$ is hydrogen; $R_7$ is hydrogen; and $R_1$ and $R_3$ are as defined in formula I.

In another embodiment of the present invention, compounds have formula V wherein, A is O; A' is O; and $R_1$, $R_6$, and $R_7$ are as defined in formula I.

In another embodiment of the present invention, compounds have formula V wherein, A is O; A' is O; $R_6$ is hydrogen; $R_7$ is hydrogen; and $R_1$ is as defined in formula I.

In another embodiment of the present invention, compounds have formula V wherein, A is O; A' is S; and $R_1$, $R_6$, and $R_7$ are as defined in formula I.

In another embodiment of the present invention, compounds have formula V wherein, A is O; A' is $CR_4R_5$; and $R_1$, $R_4$, $R_5$, $R_6$, and $R_7$ are as defined in formula I.

In another embodiment of the present invention, compounds have formula V wherein, A is O; A' is $CR_4R_5$; $R_4$ is hydrogen; $R_5$ is hydrogen; $R_6$ is hydrogen; $R_7$ is hydrogen; and $R_1$ is as defined in formula I.

In another embodiment of the present invention, compounds have formula V wherein, A is S; A' is $NR_3$; and $R_1$, $R_3$, $R_6$, and $R_7$ are as defined in formula I.

In another embodiment of the present invention, compounds have formula V wherein, A is S; A' is O; and $R_1$, $R_6$, and $R_7$ are as defined in formula I.

In another embodiment of the present invention, compounds have formula V wherein, A is S; A' is S; and $R_1$, $R_6$, and $R_7$ are as defined in formula I.

In another embodiment of the present invention, compounds have formula V wherein, A is S; A' is $CR_4R_5$; and $R_1$, $R_4$, $R_5$, $R_6$, and $R_7$ are as defined in formula I.

In another embodiment of the present invention, compounds have formula V wherein, A is S; A' is $CR_4R_5$; $R_4$ is hydrogen; $R_5$ is hydrogen; $R_6$ is hydrogen; $R_7$ is hydrogen; and $R_1$ is as defined in formula I.

In another embodiment, the present invention discloses compounds having formula VI:

VI or a pharmaceutically acceptable salt, ester, amide, or prodrug thereof wherein, A, A', $R_1$, $R_6$, and $R_7$, are as defined in formula I.

In another embodiment of the present invention, compounds have formula VI wherein, A is $NR_2$; A' is $NR_3$; and $R_1$, $R_2$, $R_3$, $R_6$, and $R_7$ are as defined in formula I.

In another embodiment of the present invention, compounds have formula VI wherein, A is $NR_2$; A' is O; and $R_1$, $R_2$, $R_6$, and $R_7$ are as defined in formula I.

In another embodiment of the present invention, compounds have formula VI wherein, A is $NR_2$; A' is S; and $R_1$, $R_2$, $R_6$, and $R_7$ are as defined in formula I.

In another embodiment of the present invention, compounds have formula VI wherein, A is $NR_2$; A' is $CR_4R_5$; and $R_1$, $R_2$, $R_4$, $R_5$, $R_6$, and $R_7$ are as defined in formula I.

In another embodiment of the present invention, compounds have formula VI wherein, A in $NR_2$; A' is $CR_4R_5$; $R_4$ is hydrogen; $R_5$ is hydrogen; $R_6$ is hydrogen; $R_7$ is hydrogen; and $R_1$ and $R_2$ are as defined in formula I.

In another embodiment of the present invention, compounds have formula VI wherein, A is O; A' is $NR_3$; and $R_1$, $R_3$, $R_6$, and $R_7$ are as defined in formula I.

In another embodiment of the present invention, compounds have formula VI wherein, A is O; A' is $NR_3$; $R_6$ is hydrogen; $R_7$ is hydrogen; and $R_1$ and $R_3$ are defined in formula I.

In another embodiment of the present invention, compounds have formula VI wherein, A is O; A' is O; and $R_1$, $R_6$, and $R_7$ are as defined in formula I.

In another embodiment of the present invention, compounds have formula VI wherein, A is O; A' is S; and $R_1$, $R_6$, and $R_7$ are as defined in formula I.

In another embodiment of the present invention, compounds have formula VI wherein, A is O; A' is $CR_4R_5$; and $R_1$, $R_4$, $R_5$, $R_6$, and $R_7$ are as defined in formula I.

In another embodiment of the present invention, compounds have formula VI wherein, A is O; A' is $CR_4R_5$; $R_6$ is hydrogen; $R_7$ is hydrogen; and $R_1$, $R_4$, and $R_5$ are as defined in formula I.

In another embodiment of the present invention, compounds have formula VI wherein, A is S; A' is $NR_3$; and $R_1$, $R_3$, $R_6$, and $R_7$ are as defined in formula I.

In another embodiment of the present invention, compounds have formula VI wherein, A is S; A' is O; and $R_1$, $R_6$, and $R_7$ are as defined in formula I.

In another embodiment of the present invention, compounds have formula VI wherein, A is S; A' is S; and $R_1$, $R_6$, and $R_7$ are as defined in formula I.

In another embodiment of the present invention, compounds have formula VI wherein, A is S; A' is $CR_4R_5$; and $R_1$, $R_4$, $R_5$, $R_6$, and $R_7$ are as defined in formula I.

In another embodiment of the present invention, compounds have formula VI wherein, A is S; A' is $CR_4R_5$; $R_4$ is hydrogen; $R_5$ is hydrogen; $R_6$ is hydrogen; $R_7$ is hydrogen; and $R_1$ is as defined in formula I.

In another embodiment, the present invention discloses compounds having formula VII:

VII or a pharmaceutically acceptable salt, ester, amide, or prodrug thereof wherein, A, $R_1$, $R_4$, $R_5$, $R_6$, and $R_7$, are as defined in formula I.

In another embodiment of the present invention, compounds have formula VII wherein, A is $NR_2$; and $R_1$, $R_2$, $R_4$, $R_5$, $R_6$, and $R_7$ are as defined in formula I.

In another embodiment of the present invention, compounds have formula VII wherein, A is $NR_2$; $R_4$ is hydrogen; $R_5$ is hydrogen; $R_6$ is hydrogen; $R_7$ is hydrogen; and $R_1$ and $R_2$ are as defined in formula I.

In another embodiment of the present invention, compounds have formula VII wherein, A is O; and $R_1$, $R_4$, $R_5$, $R_6$, and $R_7$ are as defined in formula I.

In another embodiment of the present invention, compounds have formula VII wherein, A is O; $R_4$ is hydrogen; $R_5$ is hydrogen; $R_6$ is hydrogen; $R_7$ is hydrogen; and $R_1$ is as defined in formula I.

In another embodiment of the present invention, compounds have formula VII wherein, A is S; and $R_1$, $R_4$, $R_5$, $R_6$, and $R_7$ are as defined in formula I.

In another embodiment, the present invention discloses compounds having formula VIII;

VIII or a pharmaceutically acceptable salt, ester, amide, or prodrug thereof wherein A, $R_1$, $R_4$, $R_5$, $R_6$, and $R_7$, are as defined in formula I.

In another embodiment of the present invention, compounds have formula VIII wherein, A is $NR_2$; and $R_1$, $R_2$, $R_4$, $R_5$, $R_6$, and $R_7$ are as defined in formula I.

In another embodiment of the present invention, compounds have formula VIII wherein, A is $NR_2$; $R_4$ is hydrogen; $R_5$ is hydrogen, $R_6$ is hydrogen; $R_7$ is hydrogen; and $R_1$ and $R_2$ are as defined in formula I.

In another embodiment of the present invention, compounds have formula VIII wherein, A is O; and $R_1$, $R_4$, $R_5$, $R_6$, and $R_7$ are as defined in formula I.

In another embodiment of the present invention, compounds have formula VIII wherein, A is O; $R_4$ is hydrogen; $R_5$ is hydrogen; $R_6$ is hydrogen; $R_7$ is hydrogen; and $R_1$ is as defined in formula I.

In another embodiment of the present invention, compounds have formula VIII wherein, A is S; and $R_1$, $R_4$, $R_5$, $R_6$, and $R_7$ are as defined in formula I.

Another embodiment of the present invention relates to pharmaceutical compositions comprising a therapeutically effective amount of a compound of formula I–VIII or a pharmaceutically acceptable salt, ester, amide, or prodrug thereof in combination with a pharmaceutically acceptable carrier.

Another embodiment of the invention relates to a method of treating male sexual dysfunction including, but not limited to, make erectile dysfunction and premature ejaculation comprising administering a therapeutically effective amount of a compound of formula I–VIII or a pharmaceutically acceptable salt, ester, amide, or prodrug thereof.

Another embodiment of the invention relates to a method of treating female sexual dysfunction including, but not limited to, female anorgasmia, clitoral erectile insufficiency, vaginal engorgement, dyspareunia, and vaginismus comprising administering a therapeutically effective amount of a compound of formula I–VIII or a pharmaceutically acceptable salt, ester, amide, or prodrug thereof.

Yet another embodiment of the invention relates to a method of treating asthma, epilepsy, hypertension, Raynaud's syndrome, migraine, pain, eating disorders, urinary incontinence, functional bowel disorders, neurodegeneration and stroke comprising administering a therapeutically effective amount of a compound of formula I–VIII or a pharmaceutically acceptable salt, ester, amide, or prodrug thereof.

The present invention utilizes novel intermediates for making compounds of formula I. In particular, an intermediate of formula I may be used in the process of synthesizing compounds of formula I,

IX wherein A is selected from the group consisting of O, S, and $NR_2$, wherein $R_2$ is selected from the group consisting of hydrogen, alkoxyalkyl, alkyl, arylalkyl, cycloalkyl, cycloalkylalkyl, haloalkyl, heterocyclealkyl, hydroxy, hydroxyalkyl, —$NZ_1Z_2$, and ($NZ_1Z_2$)alkyl wherein $Z_1$ and $Z_2$ are independently selected from the group consisting of hydrogen, alkyl, alkylcarbonyl, aryl, arylalkyl, and formyl.

DEFINITION OF TERMS

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like.

The term "alkoxy," as used herein, refers to an alkyl group, as defined herein, appended to the parent molecular moiety through an oxy moiety, as defined herein. Representative examples of alkoxy include, but are not limited to, methoxy, ethoxy, propoxy, 2-propoxy, butoxy, tert-butoxy, pentyloxy, hexyloxy and the like.

The term "alkoxyalkoxy," as used herein, refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, methoxymethoxy, and the like.

The term "alkoxyalkoxyalkyl," as used herein, refers to an alkoxyalkoxy group, as defined herein, appended to the parent molecular moiety through an alkyl group, as defined herein. Representative examples of alkoxyalkoxyalkyl include, but are not limited to, tert-butoxymethoxymethyl, ethoxymethoxymethyl, (2-methoxyethoxy)methyl, 2-(2-methoxyethoxy)ethyl, and the like.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, methoxymethyl, and the like.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, tert-butoxycarbonyl, and the like.

The term "alkoxycarbonylalkyl," as used herein, refers to an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, 2-tert-butoxycarbonylethyl, and the like.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like.

The term "alkylcarbonyl," as used herein, refers to an alkyl group as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, 1-oxopentyl, and the like.

The term "alkylcarbonylalkyl," as used herein, refers to an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, 3-oxopentyl, and the like.

The term "alkylcarbonyloxy," as used herein, refers to an alkylcarbonyl group, as defined herein, appended to the parent molecular moiety through an oxy moiety, as defined herein. Representative examples of alkylcarbonyloxy include, but are not limited to, acetyloxy, ethylcarbonyloxy, tert-butylcarbonyloxy, and the like.

The term "alkylsulfinyl," as used herein, refers to an alkyl group, as defined herein, appended to the parent molecular moiety through a sulfinyl group, as defined herein. Representative examples of alkylsulfinyl include, but are not limited, methylsulfinyl, ethylsulfinyl, and the like.

The term "alkylsulfonyl," as used herein, refers to an alkyl group, as defined herein, appended to the parent molecular moiety through a sulfonyl group, as defined herein. Representative examples of alkylsulfonyl include, but are not limited, methylsulfonyl, ethylsulfonyl, and the like.

The term "alkylthio," as used herein, refers to an alkyl group, as defined herein, appended to the parent molecular moiety through a thio moiety, as defined herein. Representative examples of alkylthio include, but are not limited, methylsulfanyl, ethylsulfanyl, tert-butylsulfanyl, hexylsulfanyl, and the like.

The term "alkynyl," as used herein, refers to a straight or branched chain hydrocarbon group containing from 2 to 10 carbon atoms and containing at least one carbon-carbon triple bond. Representative examples of alkynyl include, but are not limited to acetylenyl, 1-propynyl, 2-propynyl, 3-butynyl, 2-pentynyl, 1-butynyl and the like.

The term "aryl," as used herein, refers to a monocyclic carboxyclic ring system or a bicyclic carbocyclic fused ring system having one or more aromatic rings. Representative examples of aryl include, azulenyl, indanyl, indenyl, naphthyl, phenyl, tetrahydronaphthyl, and the like.

The aryl groups of this invention can be substituted with 1, 2, 3, 4, or 5 substituents independently selected from alkenyl, alkoxy, alkoxyalkoxy, alkoxyalkyl, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkyl, aryloxy, carboxy, cyano, formyl, halogen, haloalkyl, haloalkoxy, hydroxy, hydroxyalkyl, mercapto, nitro, sulfo, sulfonate, —$NR_{80}R_{81}$ (wherein, $R_{80}$ and $R_{81}$ are independently selected from hydrogen, alkyl, alkylcarbonyl, aryl, arylalkyl and formyl), and —$C(O)NR_{82}R_{83}$ (wherein, $R_{82}$ and $R_{83}$ are independently selected from hydrogen, alkyl, aryl, and arylalkyl).

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3-naphth-2-ylpropoxy, 5-phenylpentyloxy, and the like.

The term "arylalkoxycarbobyl," as used herein, refers to an arylalkoxy group, as defined herein, appended to the parent molecular moiety through a carbonyl group, as defined herein. Representative examples of arylalkoxycarbonyl include, but are not limited to, benzyloxycarbonyl, naphth-2-ylmethoxycarbonyl, and the like.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

The term "arylcarbonyl," as used herein, refers to an aryl group, as defined herein, appended to the parent molecular moiety through a carbonyl group, as defined herein. Representative examples of arylcarbonyl include, but are not limited to, benzoyl, naphthoyl, and the like.

The term "aryloxy," as used herein, refers to an aryl group, as defined herein, appended to the parent molecular moiety through an oxy moiety, as defined herein. Representative examples of aryloxy include, but are not limited to, phenoxy, napthhyloxy, 3-boromphenoxy, 4-chlorophenoxy, 4-methylphenoxy, 3,5-dimethoxyphenoxy, and the like.

The term "aryloxyalkyl," as used herein, refers to an aryloxy group, as defined herein, appended to the parent molecular moiety through an alkyl group, as defined herein. Representative examples of aryloxyalkyl include, but are not limited to, 2-phenoxyethyl, 3-naphth-2-yloxypropyl, 3-bromophenoxymethyl, and the like.

The term "azido," as used herein, refers to a —$N_3$ group.

The term "carbony," as used herein, refers to a —C(O)— group.

The term "carboxy," as used herein, refers to a —$CO_2H$ group.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, 3-carboxypropyl, and the like.

The term "cyano," as used herein, refers to a —CN group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, 3-cyanopropyl, and the like.

The term "cycloalkyl," as used herein, refers to a saturated cyclic hydrocarbon group containing from 3 to 8 carbons. Representative examples of cycloalkyl include, but are not limited to, cyclopropyl, cyclobutyl, cyclopentyl, cyclohexyl, cycloheptyl, cyclooctyl and the like.

The term "cylcoalkylalkyl," as used herein, refers to cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cylcohexylmethyl, 4-cycloheptylbutyl, and the like.

The term "formyl," as used herein, refers to a C(O)H group.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2,2,2-trifluoroethoxy, trifluromethoxy, pentafluoroethoxy, and the like.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluropentyl, and the like.

The term "heterocycle," as used herein, refers to a monocyclic- or a bicyclic-ring system. Monocyclic ring systems are exemplified by any 5-or 6-membered ring containing 1, 2, 3, or 4 heteroatoms independently selected from oxygen, nitrogen and sulfur. The 5-membered ring has from 0–2 double bonds and the 6-membered ring has from 0–3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridien, pyrimidine, pyridazine, pyrrole, pyroline, pyrrolidine, tetrahydrofuran, tetrahydrothiiphene, tetrazine, tetrazole, thiadizole, thiadoazoline, thiadiazolidine, thiazole, thiazoline, thiazolidine, thiophene, thiomorpholine, thiomorpholine sulfone, thiopyran, triazine, traizole, thrithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, isoindoline, ispquinoline, phthalazine, pyranopyridine, quinoline, quinolizine, quinoxaline, quinazoline, tetrahydroisoquinoline, tetrahydroquinoline, thiophyranopyridine, and the like.

The heterocycle groups of this invention can be sustituted with 1, 2, or 3 substituents independently selected form alkenyl, alkoxy, alkoxyalkoxy, alkoxyalkyl, alkoxycarbonly, alkyl, alkylcarbonyl, alkylcarbonyloxy, alkylsulfinyl, alkylsulfonyl, alkylthio, alkynyl, aryl, azido, arylalkoxy, arylalkoxycarbonyl, arylalkyl, aryloxy, carboxy, cyano, formyl, halogen, haloalkyl, haloalkoxy, hydroxy, hydroxyalkyl, mercapto, nitro, sulfo, sulfonate, —$NR_{80}R_{81}$ (wherein $R_{80}$ and $R_{81}$ are independently selected from hydrogen, alkyl, alkylcarbonyl, aryl, arylalkyl and formyl), and —$C(O)NR_{82}R_{83}$ (wherein $R_{82}$ and $R_{83}$ are independently selected from hydrogen, alkyl, aryl, and arylalkyl).

The term "heterocycleaklyl," as used herein, refers to a heterocycle, as defined herein, appended to the parent molecular moiety through an alkyl group, as defined herein. Representative examples of heterocyclealkyl include, but are not limited to, pyrid-3-ylmethyl, 2-pyridmidin-2-ylpropyl, and the like.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2-ethyl-4-hydroxyheptyl, and the like.

The term "lower alkyl," as used herein is a subset of alkyl and refers to a straight or branched chain hydrocarbon group containing from 1- to 4-carbon atoms. Representative examples of lower alkyl include, but are not limited to, methyl, ethyl, n-propyl, iso-propyl, n-butyl, iso-butyl, tert-butyl, and the like.

The term "mercapto," as used herein refers to a —SH group.

The term "nitro," as used herein, refers to a —$NO_2$ group.

The term "N-protecting group" or "nitrogen protecting group," as used herein, refers to those groups intended to protect an amino group against undesirable reactions during synthetic procedures. N-protecting groups comprise carbamates, amides including those containing hetero arylgroups, N-alkyl derivatives, amino acetal derivatives, N-benzyl derivatives, imine derivatives, enamine derivatives and N-heteroatom derivatives. Preferred N-protecting groups are formyl, acetyl, benzoyl, pivoloyl, phenylsulfonyl, benzyl, triphenylmethyl (trityl), t-butyloxycarbonyl (Boc), benzyloxycarbonyl (Cbz), and the like. Commonly used N-protecting groups are disclosed in T. H. Green and P. G. M. Wuts, Protective Groups in Organic Synthesis, 2nd edition, John Wiley & Sons, New York (1991), which is hereby incorporated by reference.

The term "$NA_1Z_2$," as used herein, refers to two groups $Z_1$ and $Z_2$, which are appended to the parent molecular moiety through a nitrogen atom. $Z_1$ and $Z_2$ are independently selected from hydrogen, alkyl, alkylcarbonyl, aryl, arylalkyl, and formyl. Representative examples of —$NZ_1Z_2$ include, but are not limited to, amino, benzylamino, methylamino, acetylamino, acetylmethylamino, and the like.

The term "($NZ_1Z_2$)alkyl," as used herein, refers to a —$NZ_1Z_2$ group, as defined herein, appended to the parent molecular moiety through an alkyl group, as defined herein. Representative examples of ($NZ_1Z_2$)alkyl include, but are not limited to, aminomethyl, dimethylaminomethyl, 2(amino)ethyl, 2-(dimethylamino)ethyl, and the like.

The term "oxo," as used herein, refers to an =O moiety.

The term "oxy," as used herein, refers to a —O— moiety.

The term "sulfinyl," as used herein, refers to a —S(O)— group.

The term "sulfo," as used herein, refers to a —$SO_3H$ group.

The term "sulfonate," as used herein, refers to —S(O)$_2OR_{96}$ group, wherein $R_{96}$ is selected from alkyl, aryl, and arylalky, as defined herein.

The term "sulfonyl," as used herein, refers to a —$SO_2$ group.

The term "thio," as used herein, refers to a —S— moiety.

The term "pharmaceutically acceptable prodrugs," as used herein represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in (T. Higuchi and V. Stella, Pro-drugs as Novel Delivery Systems, V. 14 of the A.C.S. Symposium Series, and in Edward B. Roche, ed., Bioreverisble Carriers in Drug Design, American Pharmaceutical Association and Pergamon Press (1987)).

The present invention contemplates pharmaceutically active metabolites formed by in vivo biotransformation of compounds of formula I–VIII. A thorough discussion of biotransformation is provided in Goodman and Gilman's, The Pharmacological Basis of Therapeutics, seventh edition.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention may be prepared synthetically form commercially available starting materials which contain asymmetric or chiral centers or by preparation of racemic mixtures followed by resolution well-known to those of ordinary skill in the art. Those methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Preferred compounds of the formula I include, but are not limited to:

5-[3-bromo-4-(triflurormethyl)phenyl]-5,10-dihydro-1H,3H-dipyrano[3,4-b:4,3-e]pyridine-4,6(7H,9H)-dione, 5-[4-fluro-3-(2-furyl)phenyl]-5,10-dihydro-1h,3H-dipyrano[3,4-b:4,3-e]pyridine-4,6(7H9H)-dione, 5-[3-(2-furyl)-4-methylphenyl]-5,10-dihydro-1h,3H-dipyrano[3,4-b:4,3-e]pyridine-4,6(7H,9H)-dione, 5-(5-bromo-4-fluoro-2-hydroxyphenyl)-5,10-dihydro-1H,3H-dipyrano[3,4-b:4,3-e]pyridine-4,6(7H,9H)-dione, 5-(4-fluoro-3-isopropenylphenyl)-5,10-dihydro-1H,3H-dipyrano[3,4b:4,3-e]pyridien-4,6(7H,9H)-dione, 5-(4-methyl-3-notrophenyl)-5,10-dihydro-1H,3H-dipyrano[3,4-b:4,3-e]pyridine-4,6(7H,9H)-dione, 5-[3-chloro-4-(trifluoeomethyl)phenyl]-5,10-dihydro-1H,3H-dipyrano[3,4-b:4,3-e]pyridine-4,6(7H,9H)-dione, 5-[3-iodo-4-(trifluoromethyl)phenyl]-5,10-dihydro-1H,3H-dipyrano[3,4-b:4,3-e]pyridine-4,6(7H,9H)-dione, 5-(3-iodo-4-methylphenyl)-5,10-dihydro-1H,3H-dipyrano[3,4-b:4,3-e]pyridine-4,6(7H,9H)-dione, 5-(3-bromo-4-chlorophenyl)-5,10-dihydro-1H,3H-dipyrano[3,4-b:4,3-e]pyridine-4,6(7H,9H)-dione, 5-(4-bromo-3-chlorophenyl)-5,10-dihydro-1H,3H-dipyrano[3,4-b:4,3-e]pyridine-4,6(7H,9H)-dione, 5-[4-chloro-3-(trifluromethyl)phenyl]-5,10-dihydro-1H,3H-dipyrano[3,4-b:4,3-e]pyridine-4,6(7H,9H)-dione, 5-(3-bromo-4-methylphenyl)-5,10-dihydro-1H,3H-dipyrano[3,4-b:4,3-e]pyridine-4,6(7H,9H)-dione, 5-(3,4-dibromophenyl)-5,10-dihydro-1H,3H-dipyrano[3,4-b:4,3-e]pyridine-4,6(7H,9H)-dione, 9-(3-bromo-4-fluorophenyl)-2,3,5,6,7,9-hexahydro-1H-pyrrolo[3,4-b][1,7]naphthyridine-1,8(4H)-dione, 5-(3-bromo-4fluorophenyl)-5,8,9,10-tetrahydro-1H-thiopyrano[3,4-b][1,7]naphthyridine-4,6(3H,7H)-dione, 5-(3-bromo-4-fluorophenyl)-5,10-dihydro-1H,3H-dithiopyrano[3,4-b:3,4-e]pyridine-4,6(7H,9H)-dione, 9-(3-bromo-4-fluorophenyl)-5,9-dihydro-3H-furo[3,4-b]thiopyrano[4,3-e]pyridine-1,8(4H,7H)-dione, 9-(3-bromo-4-fluorophenyl)-2,3,5,9-tetrahydropyrrolo[3,4-b]thiopyrano[4,3-e]pyridien-1,8(4H,7H)-dione, 10-(3-bromo-4-fluorophenyl)-3,4,6,7,8,10-hexahydropyrido[3,4-b][1,6]naphthyridine-1,9(2H,5H)-dione, 10-(3-bromo-4-fluorophenyl)-3,4,6,7,8,10-hexahydro-1H-pyrano[4,3-b][1,7]naphthyridine-1,9(5H)-dione, 10-(3-bromo-4-fluorophenyl)-3,4,6,10-tetrahydrodipyrano[3,4-b:3,4-e]pyridine-1,9(5H)8H)-dione, 10-(3-bromo-4-fluorophenyl)-3,4,6,10-tetrahydro-2H-thiopyrano[3,4-b][1,6]naphthyridine-1,9(5H,8H)-dione, 10-(3-bromo-4-fluorophenyl)-3,4,6,10-terrahydropyrano[4,3-b]thiopyrano[4,3-e]pyridine-1,9(5H,8H)-dione, 5(3-bromo-4-fluorophenyl)-7,7-dimethyl-2,3,5,8,9,10-hexahydrobenzo[b][1,7]naphthyridine-4,6(1H,7H)-dione, 9-(3-bromo-4-fluorophenyl)-2,3,5,9-tetrahydro-4H-thieno[3,2-b]thiopyrano[4,3-e]pyridine-8(7H)-one 1,1-dioxide, 10-(3-bromo-4-fluorophenyl)-3,4,6,10-tetrahydro-2H,5H-dithiopyrano[3,2-b:4,3-e]pyridine-9(8H)-one 1,1-dioxide, and 5-(3-bromo-4-fluorophenyl)-7,7-dimethyl-5,8,9,10-tetrahydro-1H-thiopyrano[3,4-b]quinoline-4,6(3H,7H)-dione or a pharmaceutically acceptable salt, ester, amide, or prodrug thereof.

More preferred compounds of formula I include, but are not limited to:

5-(3-bromo-4-fluorophenyl)-5,10-dihydro-1H,3H-dipyrano[3,4-b:4,3-e]pyridine-4,6(7H,9H)-dione, 5-(3bromo-4-fluorophenyl)-2,3,5,8,9,10-hexahydrobenzo[b][1,7]naphthyridine-4,6(1H,7H)-dione, 5-(3-bromo-4-fluorophenyl)-2,3,5,8,9,10-hexahydrobenzo[b][1,7]naphthyridine-4,6(1H,7H)-dione, 5-(3-bromo-4-fluorophenyl)-2,3,5,8,9,10-hexahydrobenzo[b][1,7]naphthyridine-4,6-(1H,7H)-dione, (−)-5-(3-bromo-4-fluorophenyl)-2,3,5,7,8,9-hexahydro-1H-cyclopenta[b][1,7]naphthyridine-4,6-dione, (+)-5-(3-bromo-4-flurorphenyl)-2,3,5,7,8,9-hexahydro-1H-cyclopent[b][1,7]naphthyridine-4,6-dione, (−)-5-(3-bromo-4-fluorophenyl)-2,3,5,8,9,10-hexahydrobenzo[b][1,7]naphthyridine-4,6(1H,7H)-dione, (+)-5-(3-bromo-4-fluorophenyl)-2,3,5,8,9,10-hexahydrobenzo[b][1,7]naphthyridine-4,6(1H,7H)-dione, 10(3-bromo-4-fluorophenyl)-3,4,6,7,8,10-hexahydro-2H-thiopyrano[3,2-b][1,7]naphthyridine-9(5H)-ine, 1,1-dioxide, 9-(3-bromo-4-fluorophenyl)-2,3,5,6,7,9-hexahydrothieno[3,2-b][1,7]naphthyridine-8(4H)-one 1,1-dioxide, 9-(3-bromo-4-fluorophenyl)-2,3,5,9-tetrahydro-4H-pyrano[3,4-b]thieno[2,3-e]pyridin-8(7H)-one 1,1-dioxide, (+)-9-(3-bromo-4-fluorophenyl)2,3,5,9-tetrahydro-4H-pyrano[3,4-b]thieno [2,3-e]pyridin-8(7H)-one 1,1-dioxide, (−)-9-(3-bromo-4fluorophenyl)-2,3,5,9-tetrahydro-4H-pyrano[3,4-b]thieno[2,3-e]pyridin-8(7H)-one 1,1-dioxide, 9-(3-cyanophenyl)-2,3,5,9-tetrahydro-4H-pyrano[3,4-b]thieno[2,3-e]pyridin-8(7H)-one 1,1-dioxide, (+) 9-(3-cyanophenyl)-2,3,5,9-tetrahydro-4H-pyrano[3,4-b]thieno[2,3-e]pyridin-8(7H)-one 1,1-dioxide, (−) 9-(3-cyanophenyl)-2,3,5,9-tetrahydro-4H-pyrano[3,4-b]thieno[2,3-e]pyridin-8(7H)-one 1,1-dioxide, 9-(4-chloro-3-nitrophenyl)-2,3,5,9-tetrahydro-4H-pyrano[3,4-b]thieno-[2,3-e]pyridin-8(7H)-one 1,1-dioxide, (+)-9-(4-chloro-3-nitrophenyl)-2,3,5,9-tetrahydro-4H-pyrano[3,4-b]thieno[2,3-e]pyridin-8(7H)-one 1,1-dioxide, (−)-9-(4-chloro-3-nitrophenyl)-2,3,5,9-tetrahydro-4H-pyrano-[3,4-b]thieno[2,3-e]pyridin-8(7H)-one 1,1-dioxide, 5-(3-bromo-4-fluorophenyl)-5,8,9,10-tetrahydro-1H-pyrano[3,4-b]quinoline-4,6(3H,7H)-dione, 10-(3-bromo-4-fluorophenyl)-3,4,6,10-tetrahydro-1H-pyrano[3,4-b]thiopyrano[2,3-e]pyridin-9(8H)-one 1,1-dioxide, 5-(3-bromo-4-fluorophenyl)-5,10-dihydro-1H,3H-pyrano[3,4-b]thiopyrano[4,3-e]pyridine-4,6(7H,9H)-dione, 5(3-bromo-4-fluorophenyl)-5,7,8,9-tetrahydrocyclopenta[b]pyrano[4,3-e]pyridine-4,6(1H,3H)-dione, 5-(3-bromo-4-fluorophenyl)-5,8,9,10-tetrahydro-1H-pyrano[3,4-b][1,7]naphthyridine-4,6(3H,7H)-dione, 9-(3-bromo-4-fluoroprophenyl)-5,9-dihydro-3H-furo[3,4-b]pyrano[4,3-e]pyridine-1,8(4H, 7H)-dione, 9-(3-bromo-4-fluorophenyl)-2-methyl-2,3,5,9-tetrahydropyrano[3,4b]pyrrolo[3,4-e]pyridine-1,8(4H,7H)-dione, 9-(3-bromo-4-fluorophenyl)-2,3,5,9-tetrahydropyrano[3,4-b]pyrrolo[3,4-e]pyridine-1,8(4H,7H)-dione, 5-(4-chloro-3-nitrophenyl)-5,10-dihydro-1H,3H-dipyrano[3,4-b:4,3-e]pyridine-4,6-(7H,9H)-dione, 5-(3-cyanophenyl)-5,10-dihydro-1H,3H-dipyrano[3,4-b:4,3e]pyridine-4,6(7H,9H)-dione, 5-(4-fluoro-3-iodophenyl)-5,10-dihydro-1H,3H-dipyrano[3,4-b:4,3-e]pyridine-4,6(7H,9H)-dione, 5-(5-bromo-2hydroxyphenyl)-5,10-dihydro-1H,3H-dipyrano[3,4-b:4,3-e]pyridine-4,6-(7H)9H)-dione, 5-[4-fluoro-3-(trifluoromethyl)phenyl]-5,10-dihydro-1H,3H-dipyrano[3,4-b:4,3-e]pyridine-4,6(7H,9H)-dione, 5-(3,4-dichlorophenyl)-5,10-dihydro-1H,3H-dipyrano[3,4-b :4,3-e]pyridine-4,6-(7H,9H)-dione, 5-2,1,3-benzoxadiazol-5-yl)-5,10-dihydro-1H,3H-dipyrano[3,4-b:4,3-e]pyridine-4,6(7H,9H)-dione, 5-(5-nitro-2-thienyl)-5,10-dihydro-1H,3H-dipyrano[3,4-b:4,3-e]pyridine-4,6-(7H,9H)-dione, 5-(5-nitro-3-thienyl)-5,10-dihydro-1H,3H-dipyrano[3,4-b:4,3-e]pyridine-4,6-(7H,9H)-dione, (+) 9-(4-fluoro-3-iodophenyl)-2,3,5,9-tetrahydro-4H-pyrano[3,4-b]thieno[2,3-e]pyridin-8(7H)-one 1,1-dioxide, (−) 9-(4-fluoro-3-iodophenyl)-2,3,5,9-tetrahydro-4H-pyrano[3,4-b]thieno[2,3-e]pyridin-8(7H)-one, 1,1-dioxide, (+) 5-(3-chloro-4-fluorophenyl)-2,3,5,7,8,9-hexahydro-1H-cyclopental[b][1,7]naphthyridine-4,6-dione, (−) 5-(3-chloro-4-fluorophenyl)-2,3,5,7,8,9-hexahydro-1H-cyclopenta[b][1,7]naphthyridine-4,6-dione, 9-(3-bromo-4-fluorophenyl)-5,6,7,9-tetrahydrofuro[3,4-b][1,7]naphthyridine-1,8(3H,4H)-dione, (+) 9-(3-bromo-4-fluorophenyl)-5,6,7,9-tetrahydrofuro[3,4-b][1,7]naphthyridine-1,8(3H,4H)-dione, (−) 9-(3-bromo-4-fluorophenyl)-5,6,7,9-tetrahydrofuro[3,4-b][1,7]naphthyridine-1,8(3H,4H)-dione, 5-(3-bromo-4-flurorphenyl)-7,7-dimethyl-5,8,9,10-tetrahydro-1H-pyrano[3,4-b]quinoline-4,6(3H,7H)-dione, (9R)-9-(3-bromo-4-fluorophenyl)-5,9-dihydro-3H-furo[3,4-b]pyrano[4,3-e]pyridine-1,8(4H,7H)-dione, (9S)-9-(3-bromo-4-fluorophenyl)-5,9-dihydro-3H-furo[3,4-b]pyrano[4,3-e]pyridine-1,8(4H,7H)-dione, 10-(3-bromo-4-fluorophenyl)-3,4,6,10-tetrahydro-2H-pyrano[3,4-b][1,6]naphthyridien-1,9(5H,8H)-dione, 10-(3,4-dichlorophenyl)-3,4,6,10-tetrahydro-2H-pyrano[3,4-b][1,6]naphthyridine-1.6,9 (5H,8H)-dione, 10-[4-chloro-3-(trifluromethyl)phenyl)]-3,4,6,10-tetrahydro-2H-pyrano[3,4-b][1,6]naphthyridine-1,9(5H,8H)-dione, 10-(4-chloro-3-nitrophenyl)-3,4,6,10-tetrahydro-2H-pyrano[3,4-b][1,6]naphthyridine-1,9(5H,8H)-dione, 10-(3,4-dibromophenyl)3,4,6,10-tetrahydro-2H-pyrano[3,4-b][1,6]naphthyridine-1,9(5H,8H)-dione, 10-(5-nitro-3-thienyl)-3,4,6,10-tetrahydro-2H-pyrano[3,4-b][1,6]naphthyridine-1,9(5H,8H)-dione, 5-(3-bromo-4-fluorophenyl)-5,8,9,10-tetrahydro-1H-thiopyrano[3,4-b]quinoline-4,6(3H,7H)-dione, 5-(3-bromo-4-fluorophenyl)-5,7,8,9-tetrahydrocyclopenta[b]thiopyrano[4,3-e]pyridine-4,6(1H,3H)-dione, and 10-(3-bromo-4-fluorophenyl)-3,4,6,10-tetrahydro-2H-pyrano[3,4-b][1,6]naphthyridine-1,9(5H,8H)-dione or a pharmaceutically acceptable salt, ester, amide, or prodrug thereof.

Preparation of Compounds of the Invention

The compounds and processes of the present invention will be better understood in connection with the following synthetic Schemes and methods which illustrate a means by which the compounds of the invention can be prepared.

The compounds of this invention can be prepared by a variety of synthetic routes. Representative procedures are shown in Schemes 1–45.

Scheme 1

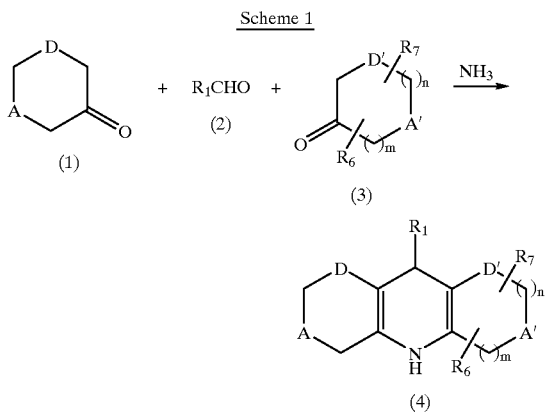

Dihydropyridines of general formula (4), wherein A, A', D, D', $R_1$, $R_6$, $R_7$, m and n are as defined in formula I, can be prepared as described in Scheme 1. Carbonyl compounds of general formula (1), aldehydes of general formula (2), and carbonyl compounds of general formula (3) can be combined in the presence of ammonia with heating in a solvent such as ethanol to provide dihydropyridines of general formula (4).

Scheme 2

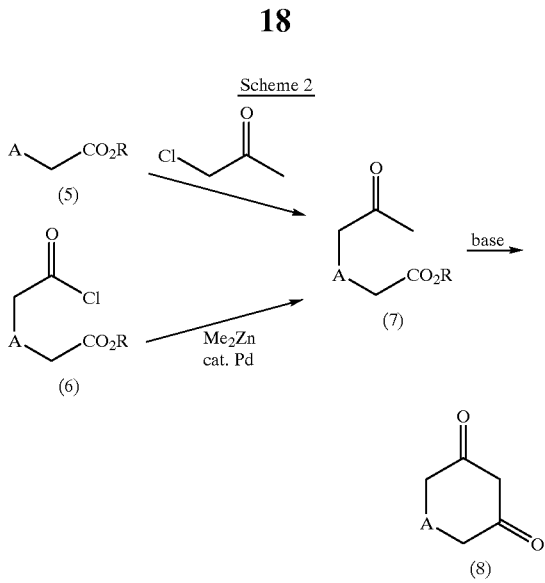

Dicarbonyl compounds of general formula (8), wherein A is as defined in formula I, can be prepared as described in Scheme 2. Esters of general formula (5), wherein A is selected from S or $NR_2$ and $R_2$ is as defined in formula I, can be alkylated with chloroacetone to provide ketoesters of general formula (7). Ketoethers of general formula (7) can cyclize in the presence of a base such as potassium tert-butoxide to provide dicarbonyl compounds of general formula (8). An alternative method of preparing ketoesters of general formula (7) can be used. Acid chlorides of general formula (6), wherein A is O, prepared as described in (Terasawa, J. Org. Chem. (1977), 42, 1163–1169) can be treated with dimethyl zinc in the presence of a palladium catalyst to provide ketoesters of general formula (7).

Scheme 3

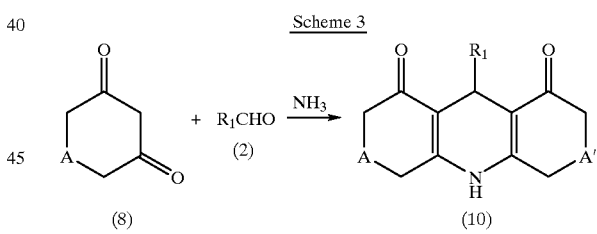

Symmetrical dihydropyridines of formula (10), wherein A=A' and A and $R_1$ are as defined in formula I, can be prepared as described in Scheme 3. Two equivalents of dicarbonyl compounds of general formula (8) can be treated with aldehydes of general formula (2) and one equivalent of ammonia with heating in a solvent such as ethanol to provide symmetrical dihydropyridiens of general formula (10).

Scheme 4

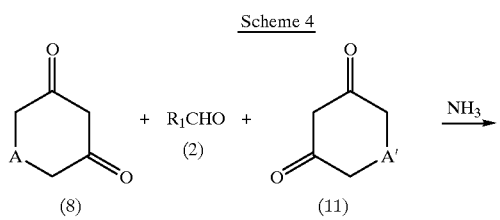

-continued

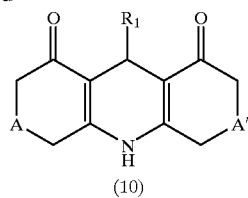

Dihydropyridines of general formula (10), wherein A, A', and $R_1$ are as defined in formula I, can be prepared as described in Scheme 4. Dicarbonyl compounds of general formula (8) can be treated with ammonia followed by addition of aldehydes of general formula (2) and dicarbonyl compounds of general formula (11) with heating in a solvent such as ethanol to provide dihyrdopyridines of general formula (10).

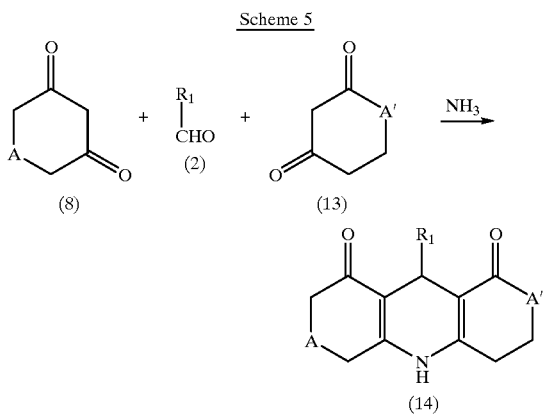

Dihydropyridines of general formula (14), wherein A, A', and $R_1$ are as defined in formula I, can be prepared as described in Scheme 5. One of the dicarbonyl components (8) or (13) can be treated with ammonia followed by addition of aldehydes of general formula (2) and the other dicarbonyl compound (8) or (13) with heating to provide dihydropyridines of general formula (14). Dicarbonyl compounds of general formula (13) can be prepared as described in (d'Angelo, Tett, Lett. (1991), 32, 3063–3066; Nakagawa, Heterocycles (1979), 13, 477–495).

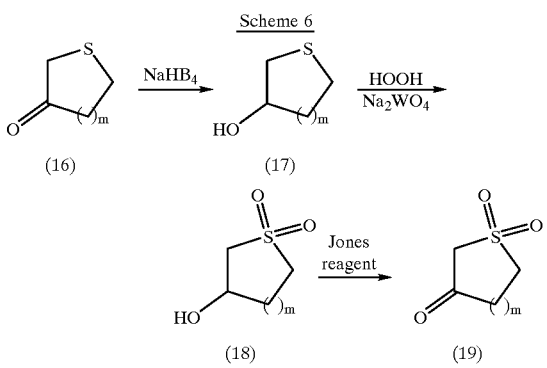

Ketosulfones of general formula (19), wherein m is 1 or 2, can be prepared as described in Scheme 6. Reduction of ketone (16) with sodium borohydride (or the like) in a solvent such as ethanol provides alcohol (17) which can be oxidized to the corresponding sulfone (18) using an oxidizing agent such as hydrogen peroxide catalyzed by sodium tungstate. Oxidation of (18) using Jones reagent or the like provides the desired keto sulfone (19).

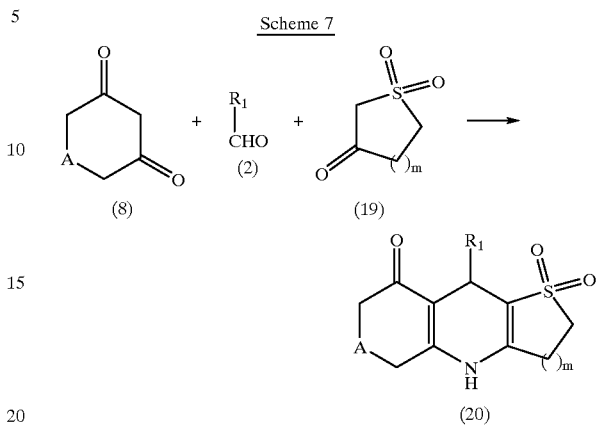

Dihydropyridines of general formula (20), wherein A and m are defined in formula I, can be prepared as described in Scheme 7. Dicarbonyl compounds of general formula (8) can be treated with ammonia, followed by addition of (2) and ketosulfone (19) with heating in a solvent such as ethanol to provide dihydropyridines of general formula (20). An additional heating step, with an acid such as HCl, may be required to drive the reaction to completion.

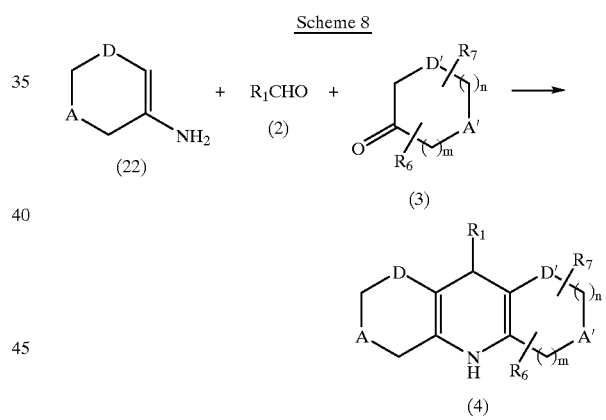

An alternate method of preparing dihydropyridines of general formula (4), wherein A, A', D, D', $R_1$, $R_6$, $R_7$, m and n are ad defined in formula I, can be used as described in Scheme 8. Enamines of general formula (22) can be treated with aldehydes (2) and carbonyl compounds (3) with heating in a solvent such as ethanol to provide dihydropyridines of general formula (4).

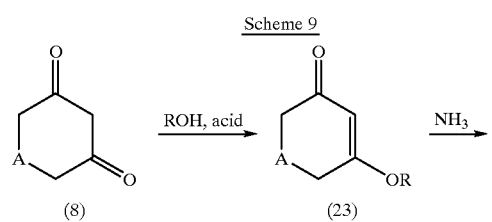

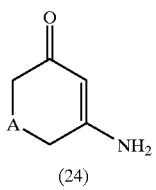

Enaminones of general formula (24), wherein A is as defined in formula I, can be prepared as described in Scheme 9. Dicarbonyl compounds (8) can be treated with an alcohol such as ethyl alcohol in the presence of an acid catalyst such as para-toluenesulfonic acid to provide vinyl ethers of general formula (23), wherein R is lower alkyl. Vinyl ethers of general formula (23) can be treated with ammonia in a solvent such as methanol to provide enaminones of general formula (24).

Scheme 10

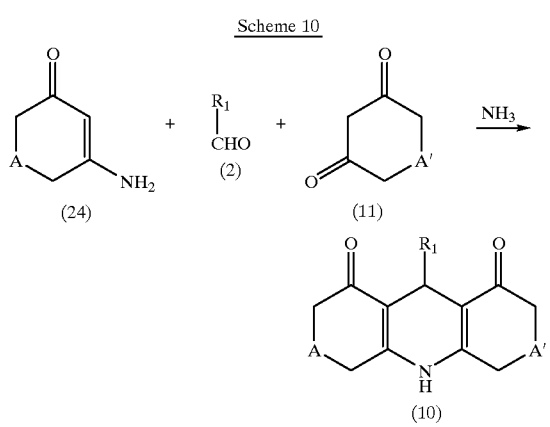

A alternate method of preparing dihydropyridines of general formula (10), wherein A, A', and $R_1$ are as defined in formula I, can be used as described in Scheme 10. Enaminones of general formula (24) can be treated with aldehydes (2) and dicarbonyls (11) with heating in a solvent such as ethanol to provide dihydropyridines of general formula (10).

Scheme 11

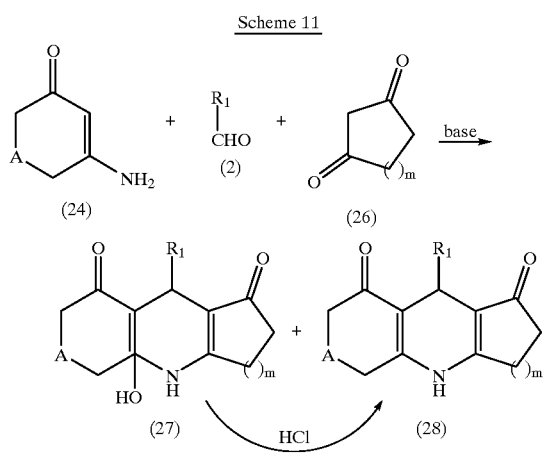

Dihydropyridines of general formula (28), wherein A, $R_1$ and m are as defined in formula I, can be prepared as described in Scheme 11. Enaminones of general formula (24) can be treated with aldehydes (2) and dicarbonyl compounds of general formula (26) with heating in a solvent such as ethanol in the presence of a base such as triethylamine to provide a mixture of hemiaminals of general formula (27) and dihydropyridines of general formula (28). Hemiaminals (27) can be treated with heat in the presence of an acid such as HCl in a solvent such as ethanol to provide dihydropyridines of general formula (28).

Scheme 12

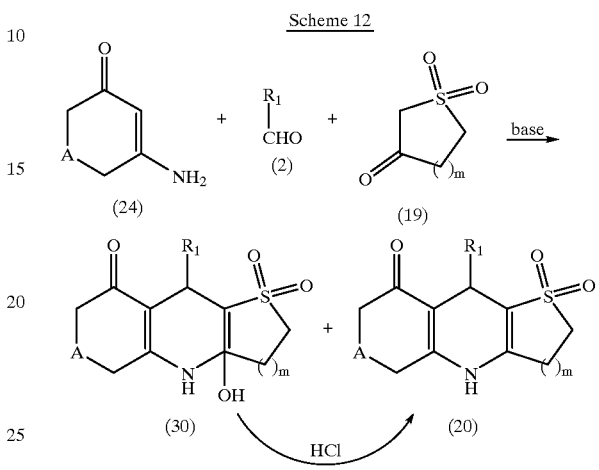

An alternate method of preparing dihydropyridines of general formula (20), wherein A, $R_1$, and m are as defined in formula I, can be used as described in Scheme 12. Enaminones of general formula (24) can be treated with aldehydes (2) and ketosulfones (19) with heating in a solvent such as ethanol in the presence of a base such as triethylamine to provide hemiaminals of general formula (30) and dihydropyridines of general formula (20). Hemiaminals (30) and dihydropyridines (20) can be heated with HCl in a solvent such as ethanol to provide dihydropyridines of general formula (20).

Scheme 13

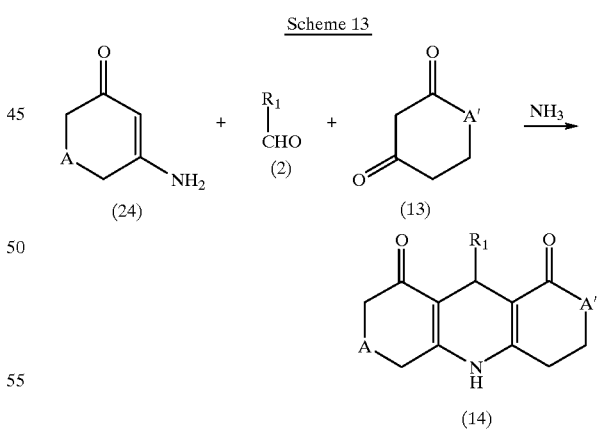

An alternate method of preparing dihydropyridines of general formula (14), wherein A, A', and $R_1$, are as defined in formula I, can be used as described in Scheme 13. Enaminones of general formula (24) can be treated with aldehydes (2) and dicarbonyls (13), from Scheme 5, with heating in a solvent such as ethanol in the presence of a base such as triethyl amine to provide dihydropyridines of general formula (14).

Scheme 14

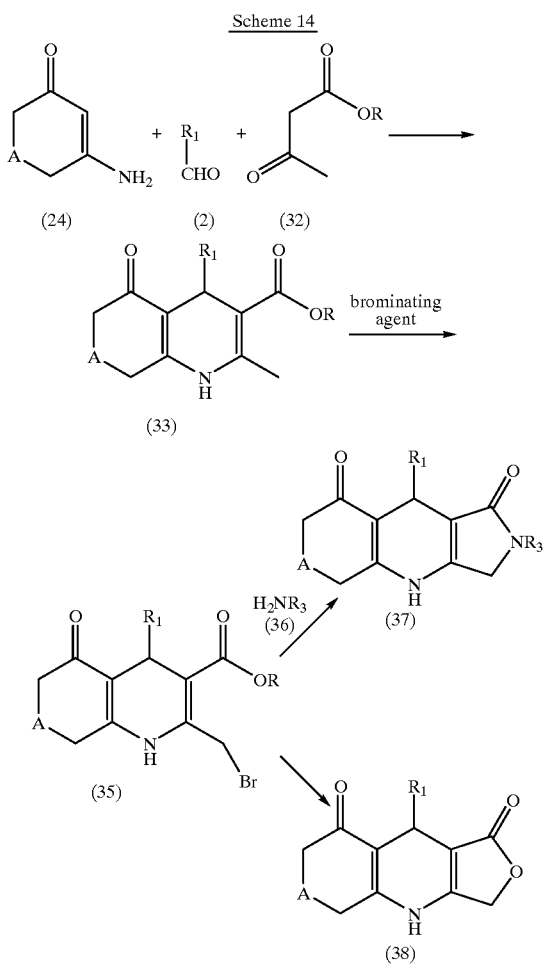

Dihydropyridines of general formula (37) and (38), wherein A, $R_1$, and $R_3$ are as defined in formula I, can be prepared as described in Scheme 14. Enaminones of general formula (24) can be treated with aldehydes (2) and acetoacetates of general formula (32), wherein R is lower alkyl, to provide dihydropyridines of general formula (33). Dihydropyridines of general formula (33) can be treated with brominating agents such as N-bromosuccinimide or pyridinium tribromide in a solvent such as methanol, ethanol, isopropanol, or chloroform to provide dihydropyridines of general formula (35). Dihydropyridines of general formula (35) can be treated with primary amines of general formula (36) or ammonia with heat in a solvent such as ethanol to provide dihydropyridines of general formula (37). Dihydropyridines of general formula (35) can be heated neat or in a solvent such as chloroform to provide dihydropyridines of general formula (38).

Scheme 15

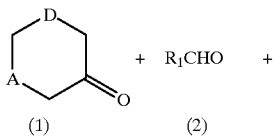

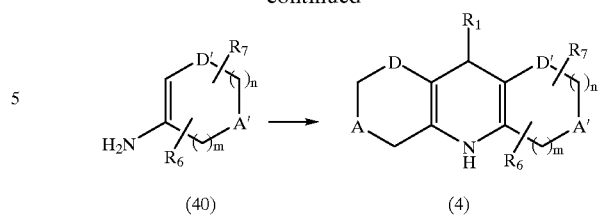

An alternate method of preparing dihydropyridines of general formula (4), wherein A, A', D, D', $R_1$, $R_6$, $R_7$, m and n are as defined in formula I, can be used as described in Scheme 15. Carbonyl compounds of general formula (1) can be treated with aldehydes (2) and enamines of general formula (40) with heating in a solvent such as ethanol to provide dihydropyridines of general formula (4).

Scheme 16

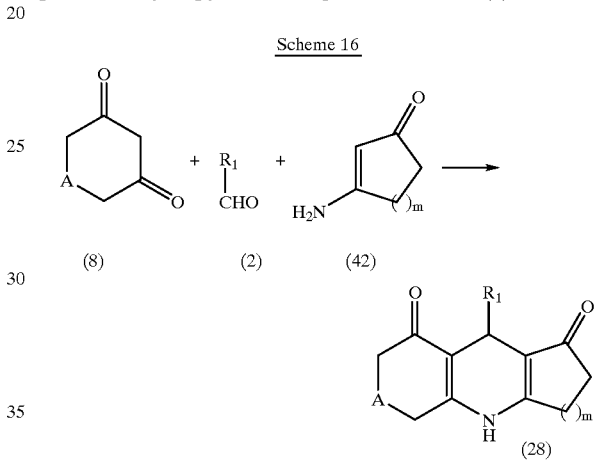

An alternate method of preparing dihydropyridines of general formula (28), wherein A, $R_1$ and m are as defined in formula I, can be used as described in Scheme 16. Dicarbonyl compounds of general formula (1) can be treated with aldehydes (2) and aminocycloalkenones of general formula (42) with heating in a solvent such as ethanol to provide dihydropyridines of general formula (28). Aminocycloalkenones of general formula (42) can be purchased commerically such as 3-amino-2-cyclohexene-1-one (Fluka) or prepared as described in (Kikani, B. Synthesis, (1991), 2, 176).

Scheme 17

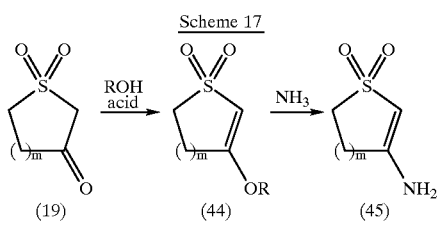

As shown in Scheme 17, enamines of general formula (45), wherein m is an integer from 1–2, can be prepared as describe in Scheme 9. Carbonyl compounds (19) can be converted to an intedmediate enol ether of general formula (44) and thence to enamines of general formula (45).

Scheme 18

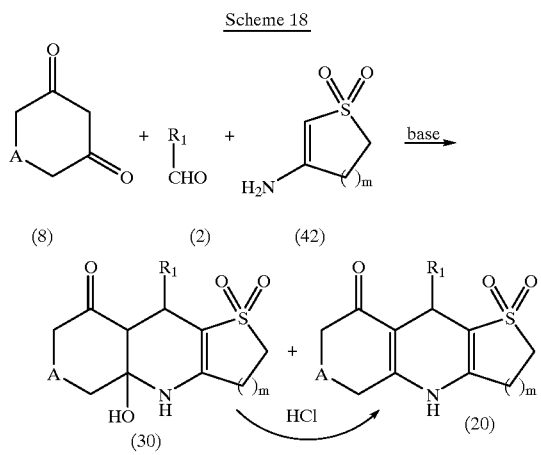

An alternate method of preparing dihydropyridines of general formula (20), wherein A, $R_1$ and m are as defined in formula I, can be used as described in Scheme 18. Diones of general formula (8) can be treated with aldehydes (2) and aminosulfones (45) with heating in a solvent such as ethanol in the presence of a base such as triethylamine to provide heminaminals of general formula (30) and dihydropyridines of general formula (20). The resulting mixture of heminaminals (30) and dihydropyridines (20) can be heated with HCl in a solvent such as ethanol to provide dihydropyridines of general formula (20).

Scheme 19

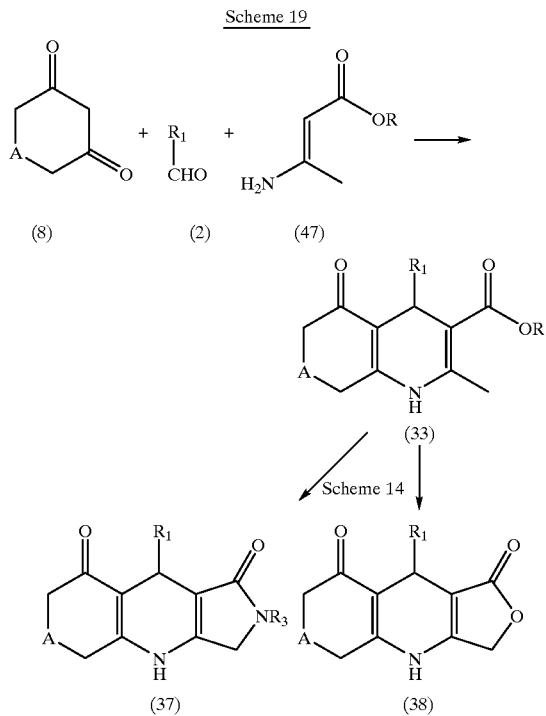

An alternate method of preparing dihydropyridines of general formula (37) and (38), wherein A, $R_1$ and $R_3$ are as defined in formula I, can be used as described in Scheme 19. Diones of general formula (8) can be treated with aldehydes (2) and aminocrotonates of general formula (47), wherein R is lower alkyl, to provide dihydropyridines of general formula (33) which can be processed as desribed in Scheme 14 to provide dihydropyridines of general formula (37) and (38).

Scheme 20

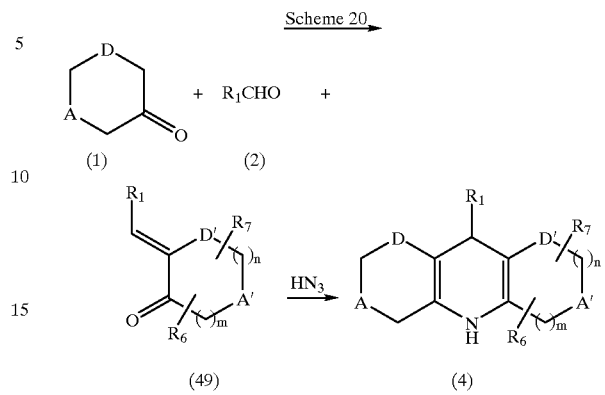

An alternate method of preparing dihydropyridines of general formula (4), wherein A, A', D, D', $R_1$, $R_6$, $R_7$, m and n are as defined in formula I, can be used as described in Scheme 20. Carbonyls of general formula (1) can be treated with α,β-unsaturated ketones of general formula (49) in the presence of ammonia with heating in a solvent such as ethanol to provide dihydropyridines of general formula (4).

Scheme 21

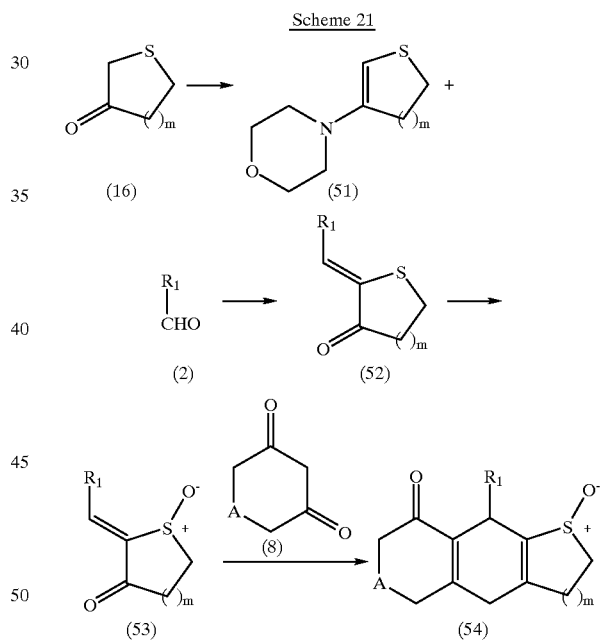

Dihydropyridines of general formula (54), wherein A, $R_1$, and m are as defined in formula I, can be prepared as described in Scheme 21. β-Keto sulfides (16) can be treated with secondary amines such as morpholine, pyrrolidine or piperidine to provide enamines (51) which can be condensed with aldehydes (2) in an appropriate organic solvent to provide sulfides of general formula (52). Sulfides of general formula (52) can be oxidized with an oxidant such as meta-chloroperoxybenzoic acid to sulfoxides of general formula (53). Sulfoxides of general formula (53) can be treated with dicarbonyls (8) and a source of ammonia such as ammonia, ammonium acetate or ammonium hydroxide with heating in a solvent such as ethyl alcohol or similar alcoholic solvent, acetonitrile or dimethylformamide to provide dihyrodopyridines of general formula (54).

Scheme 22

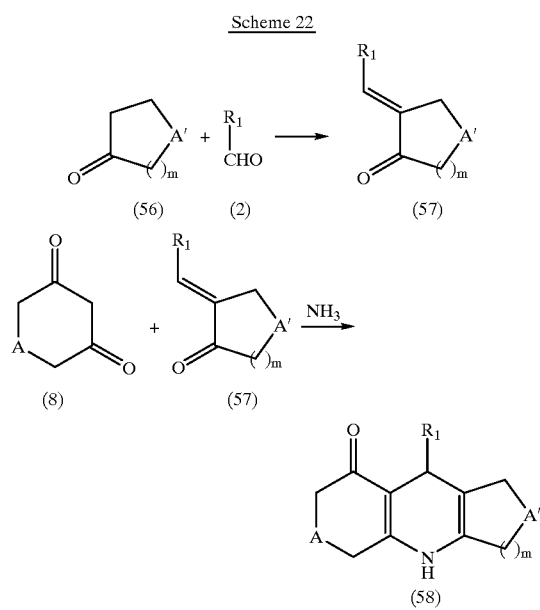

Dihydropyridines of general formula (58), wherein A, A', $R_1$, and m are as defined in formula I, can be prepared as described in Scheme 22. Carbonyl compounds (56) can be treated with aldehydes (2) using the Aldol reaction to provide ketones of general formula (57). The Aldol reaction and the conditions for this transformation are well known to those skilled in the art. Preferrably, ketones of general formula (57) can be prepared by conversion of (56) to an enamine of morpholine, pyrrolidine or piperidine followed by direct reaction with aldehydes (2). Ketones of general formula (57) can be treated with diones of general formula (8) and ammonia to provide dihydrophyridines of general formula (58).

Scheme 23

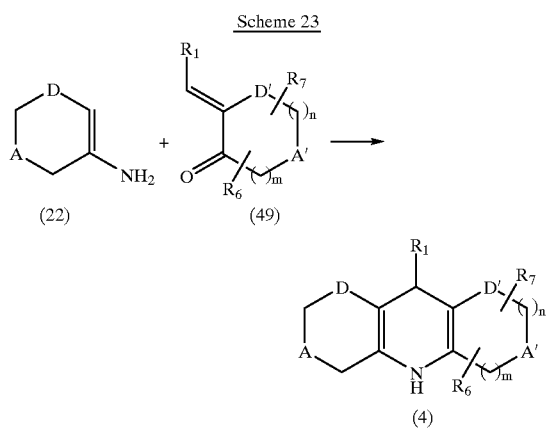

Alternate method of preparing dihydropyridines of general formula (4), wherein A, A', D, D', $R_1$, $R_6$, $R_7$, m, and n are as defined in formula I, can be used as described in Scheme 23. Enamines of general formula (22) can be treated with α,β-unsaturated ketones of general structure (49) with heating in a solvent such as ethanol to provide dihydropyridines of general formula (4).

Scheme 24

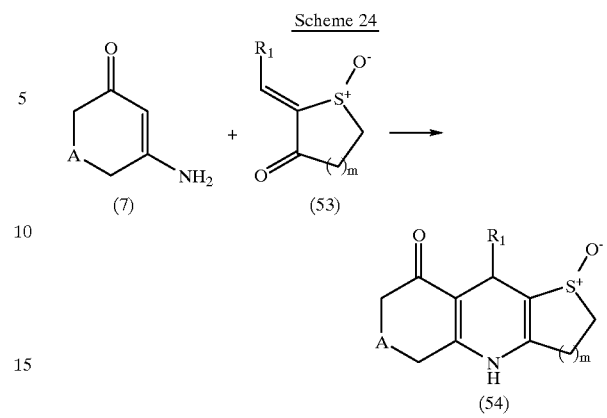

An alternate method for preparing dihydropyridines of general formula (54), wherein A, $R_1$, and m are as defined in formula I, can be used as described in Scheme 24. Enaminones of general formula (7) can be treated with α, β-unsaturated sulfoxides (53) with heating in a solvent such as ethyl alcohol or similar alcoholic solvent, acetonitrile or dimethylformamide to provide dihydropyridines of general formula (54).

Scheme 25

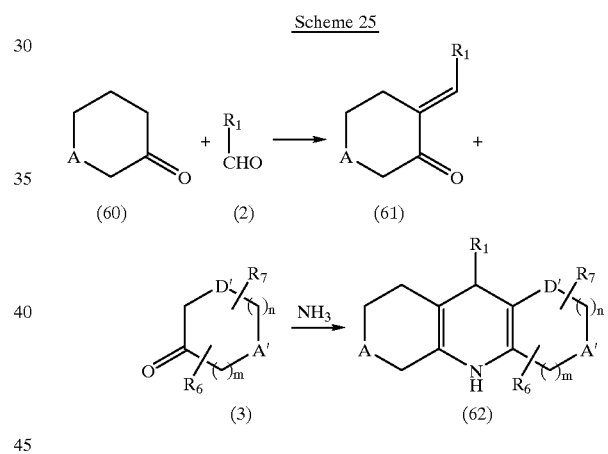

Dihydropyridines of general formula (62), wherein A, A', $R_1$, D', $R_6$, $R_7$, m, and n are as defined in formula I, can be prepared as described in Scheme 25. Carbonyls of general formula (60) can be treated with aldehydes (2) to provide α, β-unsaturated ketones of general formula (61) as described in (Eiden, F., Liebigs Ann. Chem., (1984), 11, 1759–1777). α,β-Unsaturated ketones of geneal formula (61) can be treated with carbonyls of general formula (3) in the presence of ammonia with heating in a solvent such as ethanol to provide dihydropyridiens of general formula (62).

Scheme 26

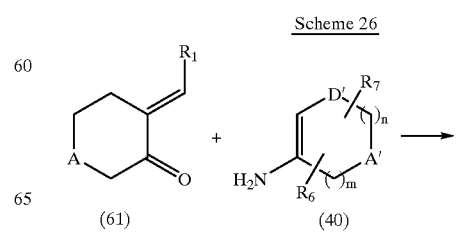

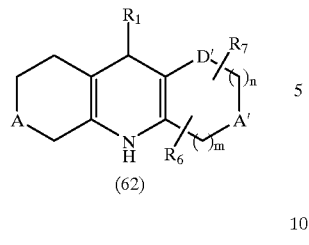
(62)

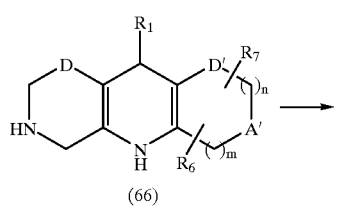
(66)

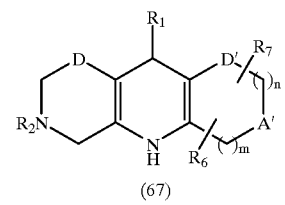
(67)

An alternate method of preparing dihydropyridines of general formula (62), wherein A, A', D', $R_1$, $R_6$, $R_7$, m, and n are as defined in formula I, can be used as described in Scheme 26. α, β-Unsaturated ketones of general formula (61) can be treated with enamines of general formula (40) with heating in a solvent such as ethanol to provide dihydropyridines of general formula (62).

Scheme 27

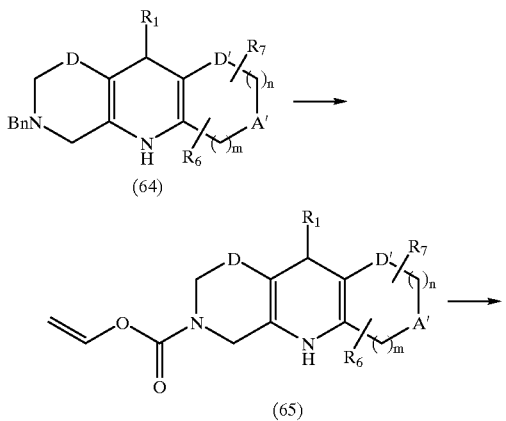

Dihydropyridines of general formula (67), wherein D, D', A', $R_1$, $R_2$, $R_6$, $R_7$, m, and n are as defined in formula I, can be prepared as described in Scheme 27. Dihydropyridines of general formula (64) prepared as described in previous Schemes can be treated with vinyl chloroformate to provide dihydropyridines of general formula (65). Dihydropyridines of general formula (65) can be treated with an acid such as hydrochloric acid in a protic solvent such as water or methanol with heating to provide dihydropyridines of general formula (66). Dihydropyridines of general formula (66) can be alkylated using standard chemistry known to those skilled in the art.

Scheme 28

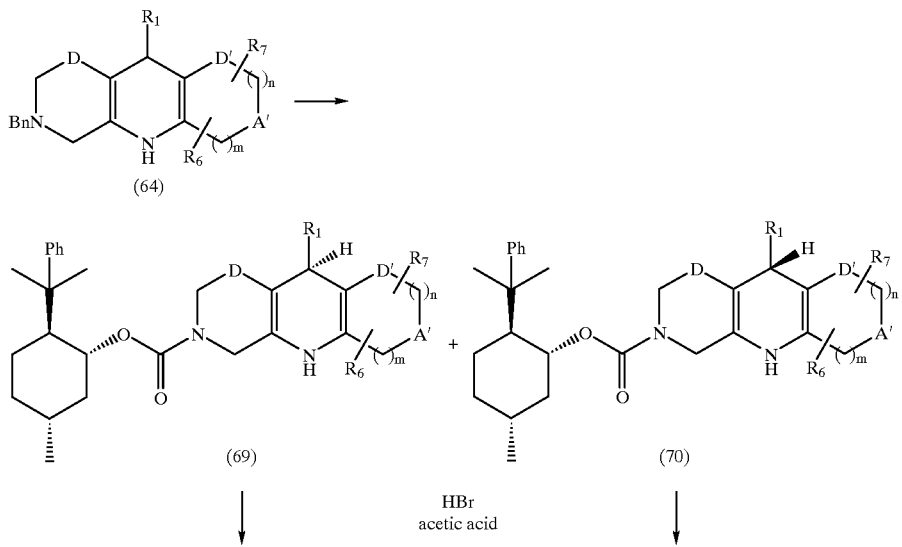

HBr
acetic acid

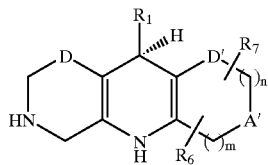

(72)

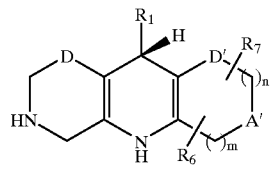

(71)

Dihydropyridines of general formula (71) and (72), wherein A', D, D', $R_1$, $R_6$, $R_7$, m, and n are as defined in formula I, can be prepared as described in Scheme 28. Dihydropyridines of general formula (68), prepared as described in previous Schemes in particular Schemes 11 and 16, can be debenzylated as described in Scheme 27 and then treated with (8)-phenylmenthol chloroformate prepared from (−) 8-phenylmenthol in a solvent such as tetrahydrofuran, methylene chloride, or chloroform or treated with (−) 8-phenylmenthol chloroformate directly to produce a mixture of diastereomeric carbamates of general formula (69) and (70). The diastereomers (69) and (70) can be separated by column chromatography over silica gel and then treated with HBr in acetic acid to produce the enantiomeric dihydropyridines of general formula (71) and (72).

Scheme 29

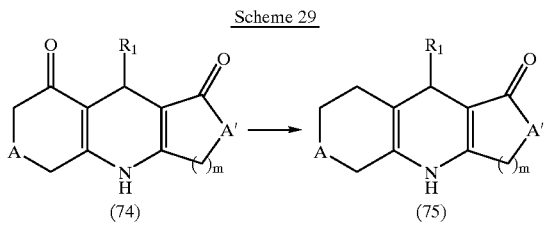

(74)         (75)

An alternate method of preparing dihydropyridines of general formula (75), wherein A, A', $R_1$, and m are as defined in formula I, can be accomplished as described in Scheme 29. Dihydropyridines of general formula (74), from previous Schemes, can be reduced to provide dihydropyridines of general formula (75). Preferably, this transformation can be accomplished by conversion of (74) to the iminoether with trimethyl or triethyloxonium tetrafluoroborate and reduction with sodium borohydride. Alternatively, the carbonyl can be converted to the thiocarbonyl using Lawesson's reagent. Desulfurization of the thiocarbonyl can be accomplished with Raney Nickel under a hydrogen atmosphere. Desulfurization can also be accomplished by conversion to the sulfonium species via addition of an alkyl halide such iodomethane and then reduction with sodium borohydride. The carbonyl may also be reduced to the methylene under conditions described in (Lakhvich, F. A., et. al., J. Org. Chem. USSR (Eng. Transl.) 25 (1989) 1493–1498).

Scheme 30

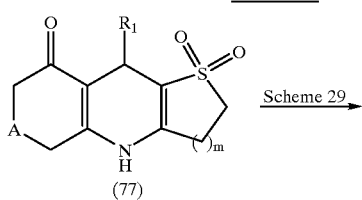

(77)

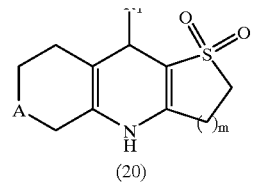

(20)

An alternate method of preparing dihydropyridines of general formula (20), wherein A, $R_1$, and m are as described in formula I, can be used as described in Scheme 30. Dihydropyridines of general formula (77), prepared as described in previous Schemes can be processed as described in Scheme 29 to provide dihydropyridines of general formula (20).

Many of the starting aryl and heteroaryl aldehydes necessary to carry out the methods described in the preceeding and following Schemes may be purchased from commercial sources or may be synthesized by known procedures found in the chemical literature. Appropriate literature references for the preparation of aryl and heteroaryl aldehydes may be found in the following section or in the Examples. For starting materials not previously described in the literature the following Schemes are intended to illustrate their preparation through a general method.

The preparation of aldehydes used to synthesize many preferred compounds of the invention may be found in the following literature references: Pearson, Org. Synth, Coll. Vol V (1973), 117; Nwaukwa, Tetrahedron Lett. (1982), 23, 3131; Badder, J. Indian Chem. Soc. (1976), 53, 1053; Khanna, J. Med. Chem. (1997), 40, 1634; Rinkes, Recl. Trav. Chim. Pays-Bas (1945), 64, 205; van der Lee, Recl. Trav. Chim. Pays-Bas (1926), 45, 687; Widman, Chem. Ber. (1882), 15, 167; Hodgson, J. Chem. Soc. (1927), 2425; Clark, J. Fluorine Chem. (1990), 50, 411; Hodgson, J. Chem. Soc. (1929), 1635; Duff, J. Chem. Soc. (1951), 1512; Crawford, J. Chem. Soc. (1956), 2155; Tanouchi, J. Med. Chem. (1981), 24, 1149; Bergmann, J. Am. Chem. Soc. (1959), 81, 5641; Other: Eistert, Chem. Ber. (1964), 97, 1470; Sekikawa, Bull. Chem. Soc. Jpn. (1959), 32, 551.

Scheme 31

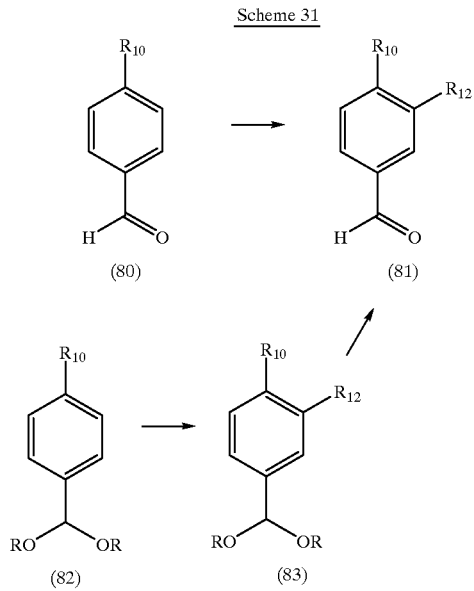

Meta, para-disubstituted aldehydes of general formula (81), wherein $R_{10}$ is selected from alkyl, haloalkyl, halo, haloalkoxy, alkoxy, alkylthio, —$NZ_1Z_2$, and —$C(O)NZ_1Z_2$, wherein $Z_1$ and $Z_2$ are independently selected from hydrogen, alkyl, alkylcarbonyl, aryl, arylalkyl, and formyl and $R_{12}$ is selected from nitro, halo, and alkylcarbonyl, can be prepared according to the method described in Scheme 31. A para substituted aldehyde of general formula (80) or the corresponding acetal protected aldehyde of general formula (82), wherein R is selected from alkyl or together with the oxygen atoms to which they are attached form a 5 or 6 membered ring wherein 1,3-dioxolanes are preferred, may be subjected to conditions of an electrophilic aromatic substitution reaction to provide aldehydes of general formula (81) or protected aldehydes of general formula (83). Preferred protecting groups for compounds of general formula (82) and (83) include dimethyl or diethyl acetals or the 1,3-dioxolanes. These protecting groups can be introduced at the beginning and removed at the end to provide substituted aldehydes of general formula (81using methods well known to those skilled in the art of organic chemistry.

Scheme 32

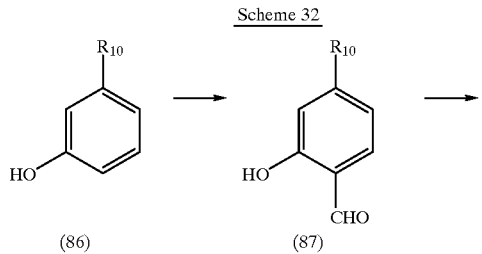

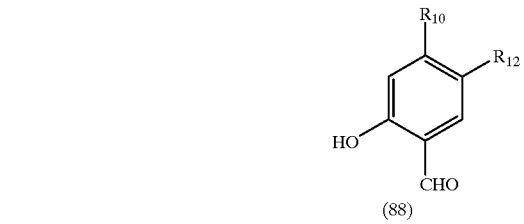

Aldehydes of general formula (88), wherein $R_{10}$ is selected from alkyl, haloalkyl, halo, haloalkoxy, alkoxy, alkylthio, —$NZ_1Z_2$, and —$C(O)NZ_1Z_2$, wherein $Z_1$ and $Z_2$ are independently selected from hydrogen, alkyl, alkylcarbonyl, aryl, arylalkyl, and formyl and $R_{12}$ is selected from nitro, halo, and alkylcarbonyl, can be prepared by the method described in Scheme 32. A meta substituted phenol (86) is converted to the para substituted salicylaldehyde (87) by reaction with a base such as sodium hydroxide and a reagent such as trichloromethane or tribromomethane, known as the Reimer-Tiemann reaction. An alternate set of reaction conditions involves reaction with magnesium methoxide and paraformaldehyde (Aldred, J. Chem. Soc. Perkin Trans. 1 (1994), 1823). The aldehyde (87) may be subjected to conditions of an electrophilic aromatic substitution reaction to provide meta, para disubstituted salicylaldehydes of general formula (88).

Scheme 33

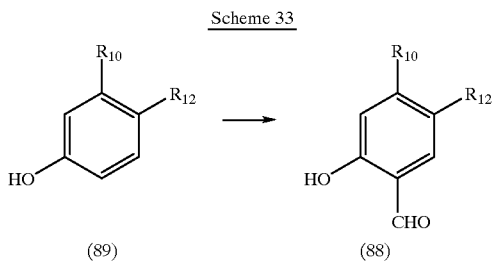

An alternative method of preparing meta, para disubstituted salicylaldehydes of general formula (88), wherein $R_{10}$ is selected from alkyl, haloalkyl, halo, haloalkoxy, alkoxy, alkylthio, —$NZ_1Z_2$, and —$C(O)NZ_1Z_2$, wherein $Z_1$ and $Z_2$ are independently selected from hydrogen, alkyl, alkylcarbonyl, aryl, arylalkyl,and formyl and $R_{12}$ is selected from nitro, halo, and alkylcarbonyl, can be used as described in Scheme 33. A meta, para disubstituted phenol of general formula (89) can be reacted with a base such as sodium hydroxide and a reagent such as trichloromethane or tribromomethane, known as the Reimer-Tiemann reaction, to provide disubstituted salicylaldehydes of general formula (88). An alternate set of reaction conditions involves reaction with magnesium methoxide and paraformaldehyde (Aldred, J. Chem. Soc. Perkin Trans. 1 (1994), 1823).

Scheme 34

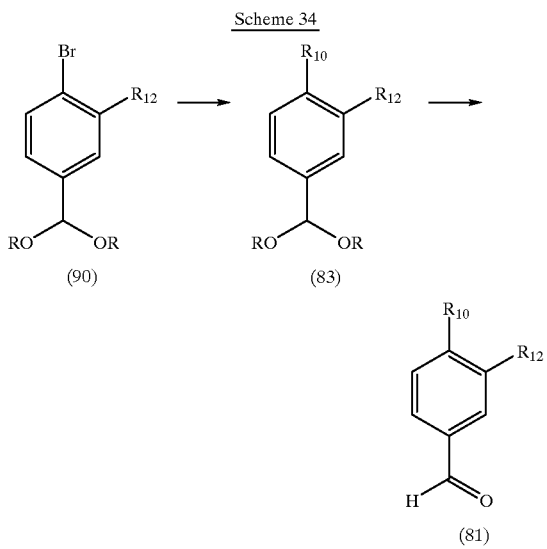

An alternative method of preparing benzaldehydes of general formula (81), wherein $R_{12}$ is selected from alkyl, haloalkyl, chlorine, fluorine, haloalkoxy, alkoxy, alkylthio, nitro, alkylcarbonyl, arylcarbonyl, —$NZ_1Z_2$, and —C(O)$NZ_1Z_2$, wherein $Z_1$ and $Z_2$ are independently selected from hydrogen, alkyl, alkylcarbonyl, aryl, arylalkyl, and formyl, and $R_{10}$ is selected from alkyl, hydroxyalkyl, alkylthio, alkylcarbonyl, and formyl, is described in Scheme 34. Protected benzaldehydes of general formula (90), wherein R is selected from alkyl or together with the oxygen atoms to which they are attached form a 5 or 6 membered ring wherein 1,3-dioxolanes are preferred, can be converted to the 3,4-disubstituted benzaldehyde of general formula (83) via conversion to an intermediate lithio or magnesio derivative, followed by reaction with an appropriate electrophile such as an aldehyde, dialkyldisulfide, a Weinreb amide, dimethylformamide, an alkyl halide or other electrophile followed by deprotection of the acetal to provide benzaldehydes of general formula (81).

Scheme 35

An alternative method of preparing benzaldehydes of general formula (81), wherein $R_{10}$ is selected from alkyl, haloalkyl, chlorine, fluorine, haloalkoxy, alkoxy, alkylthio, —$NZ_1Z_2$, and —C(O)$NZ_1Z_2$, wherein $Z_1$ and $Z_2$ are independently selected from hydrogen, alkyl, alkylcarbonyl, aryl, arylalkyl, and formyl, $R_{12}$ is selected from alkyl, hydroxyalkyl, alkylthio, alkylcarbonyl, arylcarbonyl, and formyl, can be used as described in Scheme 35. Protected benzaldehydes of general formula (92), wherein R is selected from alkyl or together with the oxygen atoms to which they are attached form a 5 or 6 membered ring wherein 1,3-dioxolanes are preferred can be processed as described in Scheme 34 to provide benzaldehydes of general formula (81).

Scheme 36

Benzaldehydes of general formula (95), wherein $R_{10}$ is selected from hydrogen, alkyl, alkylsulfonyl, aryl, heteroaryl, cyano, haloalkyl, halo, haloalkoxy, nitro, alkyoxy, alkylthio, —$NZ_1Z_2$, and —C(O)$NZ_1Z_2$, wherein $Z_1$ and $Z_2$ are independently selected from hydrogen, alkyl, alkylcarbonyl, aryl, arylalkyl, and formyl, and $R_{13}$ is selected from alkyl, arylakyl, and haloalkyl wherein preferred haloalkyl groups are selected from difluoromethyl, 2,2,2-trifluoroethyl and bromodifluoromethyl, can be prepared as described in Scheme 36. 3-Hydroxybenzaldehyde of general formula (94) can be treated with suitable alkylating reagents such as benzylbromide, iodomethane, 2-iodo-1,1,1-tribluoroethane, chlorodifluoromethane, or dibromodifluoromethane in the presence of base such as potassium carbonate, potassium tert-butoxide or sodium tert-butoxide, to provide benzaldehydes of general formula (95). The synthesis of useful 3-hydroxybenzaldehydes of general formula (94) may be found in the following literature references: J. Chem. Soc. (1923), 2820; J. Med. Chem. (1986), 29, 1982; Monatsh. Chem. (1963), 94, 1262; Justus Liebigs Ann. Chem. (1897), 294, 381; J. Chem. Soc. Perkin Trans. 1 (1990), 315; Tetrahedron Lett. (1990), 5495; J. Chem. Soc. Perkin Trans. 1 (1981), 2677.

Scheme 37

Benzaldehydes of general formula (98), wherein $R_{12}$ is selected from hydrogen, alkyl, alkylsulfonyl, aryl, heteroaryl, cyano, haloalkyl, halo, haloalkoxy, nitro, alkoxy, alkylthio, —$NZ_1Z_2$, and —C(O)$NZ_1Z_2$, wherein $Z_1$ and $Z_2$ are independently selected from hydrogen, alkyl, alkylcarbonyl, aryl, arylalkyl, and formyl, and $R_{13}$ is selected from alkyl, arylalkyl, and haloalkyl wherein preferred haloalkyl groups are selected from difluoromethyl, 2,2,2-trifluoroethyl, and bromodifluoromethyl, can be prepared as described in Scheme 37. 4-Hydroxybenzaldehydes of general formula (97) can be treated with suitable alkylating reagents such as benzylbromide, iodomethane, 2-iodo-1,1,1-trifluoroethane, chlorodifluoromethane, or dibromodifluoromethane, in the presence of base such as potassium carbonate, potassium tert-butoxide or sodium tert-butoxide to provide benzaldehydes of general formula (98). The synthesis of useful 4-hydroxybenzaldehydes of general formula (97) may be found in the following literature references: Angyal, J. Chem. Soc. (1950), 2141; Ginsburg, J. Am. Chem. Soc. (1951), 73, 702; Claisen, Justus Liebigs Ann. Chem. (1913), 401, 107; Nago, Tetrahedron Lett. (1980), 21, 4931; Ferguson, J. Am. Chem. Soc. (1950), 72, 4324; Barnes, J. Chem. Soc. (1950), 2824; Villagomez-Ibarra, Tetrahedron (1995), 51, 9285; Komiyama, J. Am. Chem. Soc. (1983), 105, 2018; DE 87255; Hodgson, J. Chem. Soc. (1929), 469; Hodgson, J. Chem. Soc. (1929), 1641.

Scheme 38

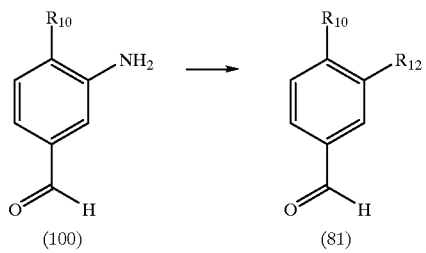

An alternate method for introduction of substituents at the 3-position of benzaldehydes of general formula (81), wherein $R_{10}$ is selected from hydrogen, alkyl, alkylsulfonyl, aryl, heteroaryl, cyano, haloalkyl, halo, haloalkoxy, nitro, alkoxy, alkylthio, and —C(O)NZ$_1$Z$_2$, wherein $Z_1$ and $Z_2$ are independently selected from hydrogen, alkyl, alkylcarbonyl, aryl, arylalkyl, and formyl can be used as described in Scheme 38. This method, also known as the Sandmeyer reaction, involves converting 3-amino benzaldehydes of general formula (100) to an intermediate diazonium salt with sodium nitrite. The diazonium salts can be treated with a bromine or iodine source to provide the bromide or iodide. The Sandmeyer reaction and conditions for effecting the transformation are well known to those skilled in the art of organic chemistry. The types of $R_{12}$ substituents that may be introduced in this fashion include cyano, hydroxy, or halo. In order to successfully carry out this transformation it may in certain circumstances be advantageous to perform the Sandmeyer reaction on a protected aldehyde. The resulting iodide or bromide can then be treated with unsaturated halides, boronic acids or tin reagents in the presence of a palladium catalyst such as tetrakis(triphenylphosphine) palladium (0) to provide benzaldehydes of general formula (81). The diazonium salts can also be treated directly with unsaturated halides, boronic acids or tin reagents in the presence of a palladium catalyst such as tetrakis (triphenylphosphine)palladium (0) to provide benzaldehydes of general formula (81).

Scheme 39

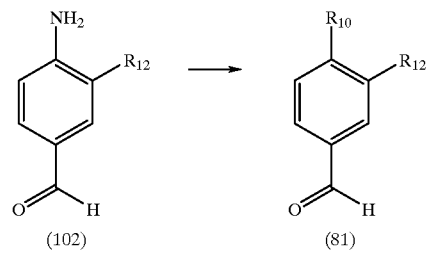

An alternate method for introduction of substituents at the 4-position of benzaldehydes of general formula (81), wherein $R_{12}$ is selected from hydrogen, alkyl, alkylsulfonyl, aryl, heteroaryl, cyano, haloalkyl, halo, haloalkoxy, nitro, alkoxy, alkylthio, and —C(O)NZ$_1$Z$_2$, wherein $Z_1$ and $Z_2$ are independently selected from hydrogen, alkyl, alkylcarbonyl, aryl, arylalkyl, and formyl, can be used as described in Scheme 39. This method, also known as the Sandmeyer reaction, involves converting 4-amino benzaldehydes of general formula (102) to an intermediate diazonium salt with sodium nitrite and then treating the diazonium salts in a similar manner as that described in Scheme 38. The types of $R_{10}$ substituents that may be introduced in this fashion include cyano, hydroxy, or halo. The Sandmeyer reaction and conditions for effecting the transformation are well known to those skilled in the art of organic chemistry. In order to successfully carry out this transformation it may in certain circumstances be advantageous to perform the Sandmeyer reaction on a protected aldehyde.

Scheme 40

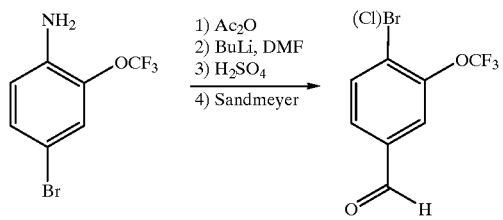

4-Bromo-3-(trifluoromethoxy)benzaldehyde or 4-chloro-3-(trifluoromethoxy)benzaldehyde (trifluoromethoxy) benzaldehyde can be prepared as described in Scheme 40. The commercially available 4-bromo-2-(trifluoromethoxy) aniline can be protected on the amino group with a suitable N-protecting group well known to those skilled in the art of organic chemistry such as acetyl or tert-butoxycarbonyl. The bromine can then be converted to the lithio or magnesio derivative and reacted directly with dimethylformamide to provide the 4-aminoprotected-3-(trifluoromethoxy) benzaldehyde derivative. Removal of the N-protecting group followed by conversion of the amine to a bromide or chloride via the Sandmeyer method of Scheme 38 followed by hydrolysis of the dioxolane provides 4-bromo-3-(trifluoromethoxy)benzaldehyde or 4-chloro-3-(trifluoromethoxy)benzaldehyde.

Scheme 41

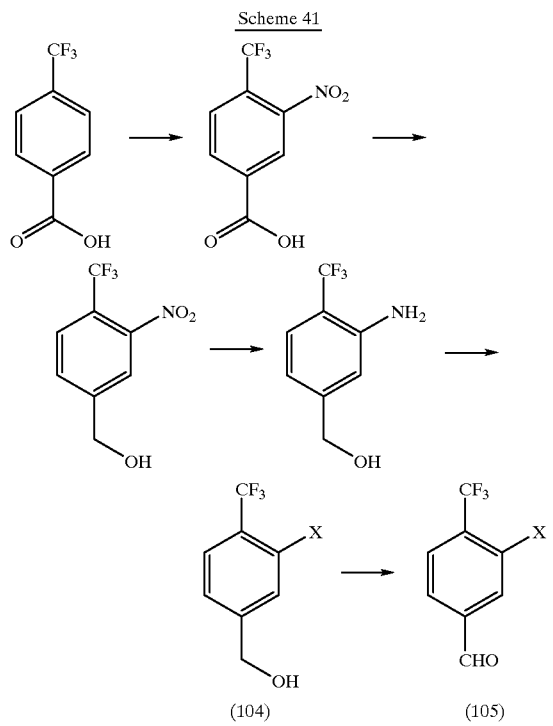

Scheme 42

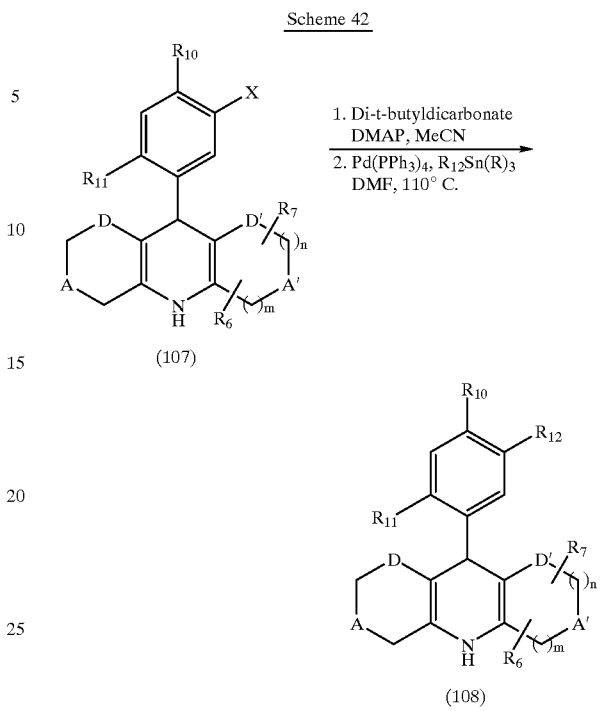

4-Trifluoromethylbenzaldehydes of general formula (105), wherein X is selected from cyano, nitro, and halo may be prepared according to the method of Scheme 41. 4-Trifluoromethylbenzoic acid is first nitrated, using suitable conditions well known in the literature such as nitric acid with sulfuric acid, and the carboxylic acid group reduced with borane to provide 3-nitro-4-trifluoromethylbenzyl alcohol. From this benzyl alcohol may be obtained the 3-nitro-4-trifluoromethylbenzaldehyde by oxidation with typical reagents such as manganese dioxide. The nitro benzylic alcohol can be reduced to the aniline using any of a number of different conditions for effecting this transformation among which a preferred method is hydrogenation over a palladium catalyst. The aniline can be converted to either a halo or cyano substituent using the Sandmeyer reaction described in Scheme 38. Benzyl alcohols of general formula (104) can be oxidized using conditions well known to those skilled in the art such as manganese dioxide or Swern conditions to provide benzaldehydes of general formula (105).

For certain aromatic ring substitutions of $R_1$ for compounds of the present invention it is preferable to effect transformations of the aromatic ring substitutions after the aldehyde has been incorporated into the core structure of the present invention. As such, compounds of the present invention may be further transformed to other distinct compounds of the present invention. These transformations involve Stille, Suzuki and Heck coupling reactions all of which are well known to those skilled in the art of organic chemistry. Shown below are some representative methods of such transformations of compounds of the present invention to other compounds of the present invention.

Dihydropyridines of general formula (108), wherein A, A', D, D', $R_6$, $R_7$, n and m are as defined in formula I, $R_{10}$ is selected from hydrogen, alkyl, alkylcarbonyl, alkylsulfonyl, aryl, heteroaryl, cyano, haloalkyl, chlorine, fluorine, haloalkoxy, nitro, alkoxy, and alkylthio, and —C(O)NZ$_1$Z$_2$, wherein $Z_1$ and $Z_2$ are independently selected from hydrogen, alkyl, alkylcarbonyl, aryl, arylalkyl, and formyl, $R_{11}$ is selected from hydrogen, hydroxy, alkoxy, haloalkoxy, and arylalkoxy, $R_{12}$ is selected from alkyl, vinyl, aryl, heteroaryl, cyano and the like, can be prepared as described in Scheme 42. Compounds of general formula (107), wherein X is selected from bromine, iodine, and triflate, are protected with a tert-butoxycarbonyl (Boc) group using standard procedures. The aromatic bromide, iodide, or triflate can be treated with a suitable tin, boronic acid, or unsaturated halide reagent in the presence of a palladium catalyst with heating in a solvent such as dimethylformamide to effect a coupling reaction that provides dihydropyridines of general formula (108). The conditions for this transformation also effect the removal of the Boc protecting group.

Scheme 43

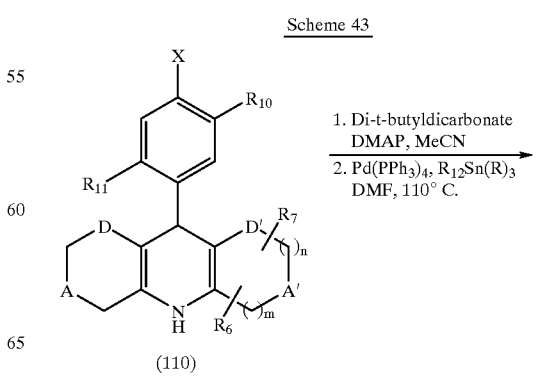

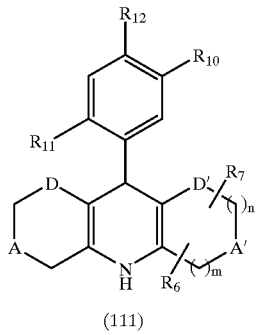

(111)

Dihydropyridines of general formula (111), wherein A, A', D, D', $R_6$, $R_7$, m, and n are as defined in formula I, $R_{10}$ is selected from hydrogen, alkyl, alkylcarbonyl, alkylsulfonyl, aryl, heteroaryl, cyano, haloalkyl, chlorine, fluorine, haloalkoxy, nitro, alkoxy, alkylthio, and —C(O)NZ$_1$Z$_2$, wherein $Z_1$ and $Z_2$ are independently selected from hydrogen, alkyl, alkylcarbonyl, aryl, arylalkyl, and formyl, $R_{11}$ is selected from hydrogen, hydroxy, alkoxy, haloalkoxy, and arylalkoxy, $R_{12}$ is selected from alkyl, vinyl, aryl, heteroaryl, cyano and the like, can be prepared as described in Scheme 43. Dihydropyridines of general formula (110), wherein X is selected from bromine, iodine, and triflate, can be protected with a tert-butoxycarbonyl (Boc) group using standard procedures. The aromatic bromide, iodide, or triflate can be reacted with a suitable tin, boronic acid, or unsaturated halide reagent in the presence of a palladium catalyst with heating in a solvent such as dimethylformamide to effect a coupling reaction that provides dihydropyridines of general formula (111). The conditions for this transformation also effect the removal of the Boc protecting group.

Scheme 44

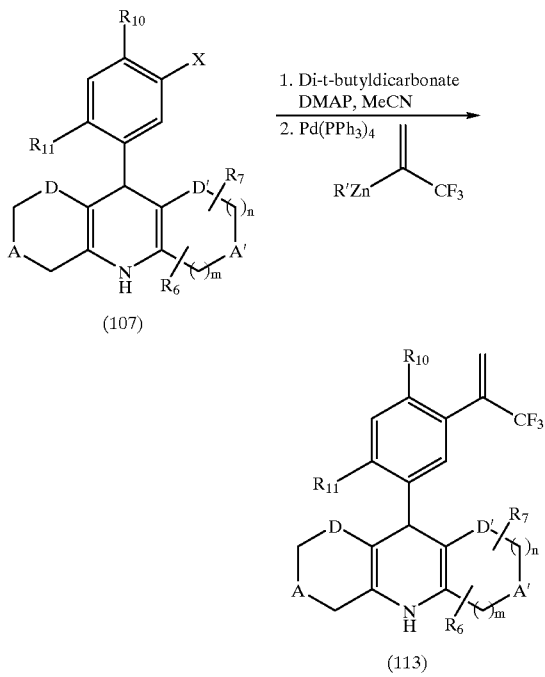

Dihydropyridines of general formula (113), wherein A, A', D, D', $R_6$, $R_7$, m, and n are as defined in formula I, $R_{10}$ is selected from hydrogen, alkyl, alkylcarbonyl, alkylsulfonyl, aryl, heteroaryl, cyano, haloalkyl, chlorine, fluorine, haloalkoxy, nitro, alkoxy, alkylthio, and —C(O)NZ$_1$Z$_2$, wherein $Z_1$ and $Z_2$ are independently selected from hydrogen, alkyl, alkylcarbonyl, aryl, arylalkyl, and formyl, and $R_{11}$ is selected from hydrogen, hydroxy, alkoxy, haloalkoxy, and arylalkoxy, can be prepared as described in Scheme 44. Dihydropyridines of general formula (107), wherein X is selected from bromine, iodine, and triflate can be protected with a tert-butoxycarbonyl (Boc) group using standard procedures. The aromatic bromide, iodide, or triflate can be treated with a suitable halozinc reagent in the presence of a palladium catalyst with heating in a solvent such as dimethylformamide to effect a coupling reaction that provides dihydropyridines of general formula (113). The conditions for this transformation also effect the removal of the Boc protecting group. The types of meta substituents that may be introduced in this fashion include trihalopropenyl and more specifically the trifluoropropenyl group.

Scheme 45

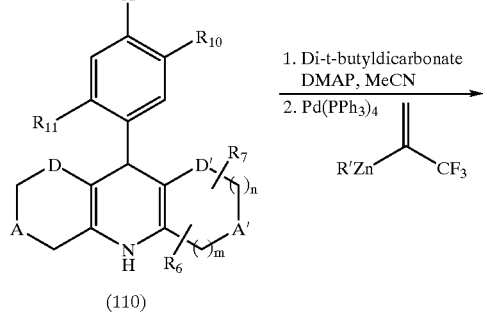

(110)

(116)

Dihydropyridines of general formula (116), wherein A, A', D, D', $R_6$, $R_7$, m and n are as defined in formula I, $R_{10}$ is selected from hydrogen, alkyl, alkylcarbonyl, alkylsulfonyl, aryl, heteroaryl, cyano, haloalkyl, chlorine, fluorine, haloalkoxy, nitro, alkoxy, alkylthio, —C(O)NZ$_1$Z$_2$, wherein $Z_1$ and $Z_2$ are independently selected from hydrogen, alkyl, alkylcarbonyl, aryl, arylalkyl, and formyl, $R_{11}$ is selected from hydrogen, hydroxy, alkoxy, haloalkoxy, and arylalkoxy, can be prepared as described in Scheme 45. Dihydropyridines of general formula (110), wherein X is selected from bromine, iodine, and triflate can be protected with a tert-butoxycarbonyl (Boc) group using standard procedures. The aromatic bromide, iodide, or triflate can be treated with a suitable halozinc reagent in the presence of a palladium catalyst with heating in a solvent such as dimethylformamide to effect a coupling reaction that provides dihydropyridines of general formula (116). The conditions for this transformation also effect the removal of the Boc protecting group. The types of para substituents that may be introduced in this fashion include trihalopropenyl and more specifically the trifluoropropenyl group.

In addition to the use of the method illustrated in Scheme 28, individual enantiomers of compounds of the present invention may also be separated by chiral chromatography.

The following methods are intended as an illustration of and not a limitation upon the scope of the invention as defined in the appended claims. Further, all citations herein are incorporated by reference.

EXAMPLE 1

5-(3-bromo-4-fluorophenyl)-5,10-dihydro-1H,3H-dipyrano[3,4-b:4,3-e]pyridine-4,6(7H,9H)-dione A solution of tetrahydropyran-3,5-dione (Terasawa, J. Org. Chem. (1977), 42, 1163–1169) (1.2 g, 10.5 mmol), 3-bromo-4-fluorobenzaldehyde (1.1 g, 5.4 mmol) and 2.0M ammonia in ethyl alcohol (8 mL, 16 mmol) was heated in a sealed tube to 80° C. for 36 hours and then allowed to cool to ambient temperature. The insolubles were filtered off and the filtrate evaporated to dryness. The residue was purified by flash chromatography over silica gel (5% methanol/methylene chloride) to provide an orange foam that was triturated with ether and ethyl acetate to provide the title compound (111 mg) as an orange solid.
mp>250° C.
MS (APCI(+))m/z 392 (M-H);
$^1$H NMR (DMSO-d$_6$) δ4.06 (s, 4H), 4.41–4.60 (AB qu, 4H), 4.94 (s, 1H), 7.19–7.32 (m, 2H), 7.42 (dd, 1H), 10.12 (br s, 1H);
Anal. Calcd for C$_{17}$H$_{13}$BrFNO$_4$0.5 H$_2$O:C, 50.64; H, 3.49; N, 3.47. Found: C, 50.66; H, 3.56; N, 3.90.

EXAMPLE 2

5-(3-bromo-4-fluorophenyl)-2,3,5,8,9,10-hexahydrobenzo[b][1,7]naphthyridine-4,6(1H,7H)-dione hydrochloride

EXAMPLE 2A 2-benzyl-5-(3-bromo-4-fluorophenyl)-2,3,5,8,9,10-hexahydrobenzo[b][1,7]naphthyridine-4,6(1H,7H)-dione hydrochloride A solution of 3-amino-2-cyclohexen-1-one (0.55 g, 5.0 mmol), 3-bromo-4-fluorobenzaldehyde (1.01 g, 5.0 mmol) and N-benzylpiperidine-3,5-dione (Ziegler, J. Amer. Chem. Soc. (1973), 95, 7458–7464) (1.01 g, 5.0 mmol) was heated for 3 days in ethyl alcohol (10 mL) in a sealed tube and then allowed to cool to ambient temperature. The solvent was evaporated and the residue was purified by flash chromatography over silica gel (5% ethanol/methylene chloride) to provide the title compound (0.84 g) which was converted to the HCl salt.
mp 240–241° C.;
MS (DCI/NH$_3$)m/z481(M+H)$^+$;
$^1$H NMR (CDCl$_3$)(free base) δ2.0(m, 2H), 2.67 (m, 2H), 2.48 (m,2H), 3.05–3.48 (m, 4H), 3.7 (M, 2H), 5.1 (s, 1H), 6.05 (bs, 1H), 6.99 (t, 1H), 7.32 (m, 6H), 7.41 (dd, 1H);
Anal. Calcd for C$_{25}$H$_{22}$BrFN$_2$O$_2$HCl:C, 57.99; H, 4.48; N, 5.41. Found: C, 57.87; H, 4.46;
N, 5.35.

EXAMPLE 2B vinyl 5-(3-bromo-4-fluorophenyl)-4,6-dioxo-3,4,5,6,7,8,9,10-octahydrobenzo[b][1,7]naphthyridine-2(1H)-carboxylate A solution of the free base of the produce from Example 2A (0.40 g, 0.83 mmol) in methylene chloride (50 mL) was treated with vinyl chloroformate (0.085 mL) and allowed to stir at ambient temperature overnight. The solvent was evaporated and the residue was purified by flash chromatography over silica gel (5:95:1 ethanol/methylene chloride/saturated ammonium hydroxide) to provide the title compound (0.25 g).
MS (ESI(+))m/z461 (M+H)$^+$;
$^1$H NMR (CDCl$_3$) δ2.08(m, 2H), 2.4(m, 2H), 2.55 (m, 2H), 3.9 (d, 1H), 4.15 (d, 1H), 4.43 (d,1H), 4.57 (d, 1H), 4.75 (d, 1H), 4.85 (d, 1H), 5.12 (s, 1H), 6.9(t, 1H), 7.14 (m, 1H), 7.3 (m, 1H), 7.48 (m, 1H).

EXAMPLE 2C 5-(3-bromo-4-fluorophenyl)-2,3,5,8,9,10-hexahydrobenzo[b][1,7]naphthyridine-4,6-(1H,7H)-dione hydrochloride A solution of the product from Example 2B (0.25 g) in ethyl alcohol (20 mL) was treated with 6M HCl (20 mL) and heated to reflux for 1.5 hours. The ethyl alcohol was evaporated and the aqueous portion basified with 1N sodium hydroxide. The basified solution was extracted with methylene chloride (3x). The combined methylene chloride extractions were concentrated and the residue was purified by flash chromatography over silica gel (10:90:1 ethanol/methylene chloride/saturated ammonium hydroxide) to provide the title compound (0.10 g) which was converted to the hydrochloride salt.
mp 220–222° C.;
MS (ESI(+))m/z 391 (M+H)$^+$;
MS (ESI(-))m/z 389 (M-H)$^-$;
$^1$H NMR (DMSO-d$_6$) (free base) δ1.72–2.0 (m, 2H), 2.21 (t, 2H), 2.51 (m, 2H), 3.17 (s, 2H), 3.58 (m, 2H), 4.89 (s, 1H), 7.19 (m, 2H), 7.4 (m, 1H), 9.6 (s, 1H);
Anal. Calcd for C$_{18}$H$_{15}$N$_2$FBrO$_2$HCl:C, 50.67; H, 3.78; N, 6.51. Found: C, 50.73;H, 4.34;
N, 6.18.

EXAMPLE 3

5-(3-bromo-4-fluorophenyl)-2-methyl-2,3,5,8,9,10-hexahydrobenzo[b][1,7]naphthyridine-4,6(1H,7H)-dione hydrochloride A solution of the product from Example 2C (0.10 g) in methyl alcohol (4 mL) was treated with 37% aqueous formaldehyde (0.4 mL), sodium cyanoborohydride (23 mg) and glacial acetic acid (added dropwise to bring the pH to 5) and allowed to stir overnight at ambient temperature. The reaction mixture was concentrated and the residue partitioned between aqueous sodium bicarbonate and methylene chloride. The methylene chloride layer was dried with sodium sulfate, filtered, and the solvent evaporated to provide the free base of the title compound (70 mg). The free base was converted to the hydrochloride salt and crystallized from ethanol/ether.
mp 248–250° C.;
MS (APCI(+))m/z 405 (M+H)$^+$;
$^1$H NMR (DMSO-d$_6$) (free base) δ1.78–2.0 (m, 2H), 2.22 (m, 2H), 2.29 (s, 3H), 3.1 (m, 2H), 3.5 (m, 2H), 4.83 (s, 1H), 7.15 (m, 1H), 7.2 (t, 1H), 7.37 (dd, 1H), 9.72 (s, 1H);
Anal. Calcd for C$_{19}$H$_{17}$N$_2$FBrO$_2$HCl:C, 51.78; H, 4.11; N, 6.35 Found: C, 51.73; H, 4.40;
N, 621.

EXAMPLE 4

5-(3-bromo-4-fluorophenyl)-2,3,5,8,9,10-hexahydropyrido[3,4-b][1,7]naphthyridine-4,6(1H,7H)-dione dihydrochloride

EXAMPLE 4A 2,8-dibenzyl-5-(3-bromo-4-fluorophenyl)-2,3,5,8,9,10-hexahydropyrido[3,4-b][1,7]naphthyridine-4,6(1H,7H)-dione A solution of N-benzylpiperidine-3,5-dione (Ziegler, J. Amer. Chem. Soc. (1973), 95, 7458–7464) (2.2 g, 10 mmol), 3-bromo-4-fluorobenzaldehyde (1.02 g, 5.0 mmol) and 2.0 M ammonia in ethyl alcohol (2.5 mL) was heated in ethyl alcohol (10 mL) at 70° C. for 3 days. The reaction mixture was allowed to cool to ambient temperature and was concentrated. The residue was purified by chromatography over silica gel (5% ethanol/methylene chloride) to provide the title compound (0.62 g).
MS (ESI(−)) m/z 570 (M−H)$^-$;
$^1$H NMR (DMSO-d$_6$) δ2.97 (d, 2H), 3.16 (m, 2H), 3.42 (m, 3H), 3.61 (g, 4H), 4.82 (s, 1H), 7.13–7.42 (m, 13H), 9.32 (s, 1H).

EXAMPLE 4B divinyl 5-(3-bromo-4-fluorophenyl)-4,6-dioxo-4,5,6, 7,9,10-hexahydropyrido[3,4-b][1,7]naphthyridine-2, 8(1H,3H)-dicarboxylate A solution of the product from Example 4A (0.5 g, 0.87 mmol) in methylene chloride (5 mL) was treated with vinyl chloroformate, (0.16 mL, 1.9 mmol) and allowed to stir at ambient temperature overnight. The solvent was evaporated and the residue purified by flash chromatography over silica gel (8:2 ethylacetate/hexane) to provide the title compound (0.30 g).
MS (ESI(+)) m/z 532 (M+H)$^+$;
$^1$H NMR (DMSO-d$_6$) δ3.95 (d, 2H), 4.2 (d, 2H), 4.46 (d, 2H), 4.65 (d, 2H), 4.77–4.94 (m, 4H), 5.15 (s, 1H), 7.0 (t, 1H), 7.1 (d, 1H), 7.14 (d, 1H), 7.32 (m, 1H), 7.4 (m, 1H).

EXAMPLE 4C 5-(3-bromo-4-fluorophenyl)-2,3,5,8,9,10-hexahydropyrido[3,4-b][1,7]naphthyridine-4,6(1H, 7H)-dione dihydrochloride A solution of the product from Example 4B (0.22 g, 0.41 mmol) in ethyl alcohol (5 mL) was treated with concentrated hydrochloric acid (0.10 mL) refluxed for 3 hours, allowed to cool to ambient temperature and treated with ether. The resulting solid precipitate was collected and dried to provide the title compound (0.12 g).
MS (ESI(−)) m/z 391 (M−H)$^-$;
$^1$H NMR (DMSO-d$_6$) δ3:78 (q, 4H), 4.22 (q, 4H), 4.95 (S, 1H), 7.22 (t, 1H), 7.32 (m, 1H), 7.48 (dd, 1H), 11.48 (s, 1H);
Anal. Calcd for $C_{17}H_{15}N_3O_2FBR2HCl$:C, 43,90; H, 3.68; N, 9.03. Found:C,44.45; H, 3.86;N,8.75.

EXAMPLE 5

(−)-5-(3-bromo-4-fluorophenyl)-2,3,5,7,8,9-hexahydro-1H-cyclopenta[b][1,7]naphthyridine-4,6-dione hydrochloride

EXAMPLE 5A 2-benzyl-5-(3-bromo-4-fluorophenyl)-2,3,5,7,8,9-hexahydro-1H-cyclopenta[b][1,7]naphthyridine-4,6-dione A solution of 3-amino-2-cyclopenten-1-one (Kikani, B. B., Synthesis, (1991), 2, 176) (0.97 g, 10 mmol), 3-bromo-4-fluorobenzaldehyde (2.0 g, 10 mmol) and N-benzylpiperidine-3,5-dione (Ziegler, J. Amer. Chem. Soc. (1973), 95, 7458–7464) (2.2 g, 10 mmol) in ethyl alcohol (10 mL) was heated to reflux for 72 hours and then allowed to cool to ambient temperature. The solvent was evaporated and the residue was purified by flash chromatography over silica gel (5% ethanol/methylene chloride) to provide the title compound (3.0 g).
MS (ESI(−)) m/z 465 (M−H)$^-$;
$^1$H NMR (DMSO-d$_6$) δ2.28 (m, 2H), 2.5–2.7 (m, 2H), 3.07 (AB qu, 2H), 3.4 (m, 2H), 3.65 (s, 2H), 4.65 (s, 1H), 7.15–7.45 (m, 8H), 10.25, (s, 1H).

EXAMPLE 5B (1R,2S,5R)-5-methyl-2-(1-methyl-1-phenylethyl) cyclohexyl 5-(3-bromo-4-fluorophenyl)-4,6-dioxo-1, 3,4,5,6,7,8,9-octahydro-2H-cyclopenta[b][1,7] naphthyridine-2-carboxylate A solution of the product from Example 5A (1.9 g, 4.0 mmol) in THF (30 mL) was treated with 8-phenylmenthol chloroformate prepared from (−)-8-phenylmenthol as described in (Yamamoto, Y., J. Amer. Chem. Soc. (1992), 114, 121–125) (1.45 g, 4.92 mmol) in THF (10 mL), stirred for 3 days at ambient temperature and partitioned between aqueous sodium bicarbonate and methylene chloride. The organic layer as separated, dried with sodium sulfate, filtered and concentrated to provide a mixture of diasteromeric carbamates. The diastereomeric mixture was subjected to column chromatography over silica gel (20% hexanes/ethyl acetate) to provide the title compound (0.32 g) as the less polar diastereomer and mixed fractions containing both diastereomers (0.9 g).
MS (ESI(−)) m/z 635 (M−H)$^-$;
$^1$H NMR (DMSO-d$_6$) δ0.8 (m, 4H), 1.1 (s, 3H), 1.118 (m, 2H), 1.22 (s, 3H), 1.6 (m, 2H), 1.8 (m, 1H), 2.02 (m, 2H), 2.3 (m, 2H), 2.6 (m, 1H), 2.75 (m, 1H), 3.02 (d, 1H), 3.62 (d, 1H), 3.9 (d, 1H), 4.58 (d, 2H), 4.68 (s, 1H), 7.02–7.38 (m, 8H).

EXAMPLE 5C (1R,2S,5R)-5-methyl-2-(1-methyl-1-phenylethyl) cyclohexyl 5-(3-bromo-4-fluorophenyl)-4,6-dioxo-1, 3,4,5,6,7,8,9-octahydro-2H-cyclopenta[b][1,7] naphthyridine-2-carboxylate The diastereomeric mixture from Example 5B was crystallized from ethyl alcohol to provide the title compound (0.45 g) as the more polar diastereomer.
MS (ESI(−)) m/z 635 (M−H)$^-$;
$^1$H NMR (DMSO-d$_6$) δ0.82 (d, 3H), 1.02 (s, 3H), 1.18 (s, 3H), 1.18 (m, 2H), 1.58 (m, 2H), 1.68 (s, 1H), 1.98 (m, 2H), 2.3 (m, 2H), 2.61 (m, 1H), 2.75 (m, 1H), 3.2 (m, 1H), 3.6 (m, 2H), 4.0 (m, 1H), 4.52 (m, 2H), 4.55 (s, 1H), 6.45 (m, 1H), 6.82 (m, 2H), 7.1 (m, 2H), 7.25 (m, 2H), 7.41 (m, 1H).

EXAMPLE 5D (−)-5-(3-bromo-4-fluorophenyl)-2,3,5,7,8,9-hexahydro-1H-cyclopenta[b][1,7]naphthyridine-4,6-dione hydrochloride A solution of the product from Example 5B (0.32 g, 0.52 mmol) was treated with 48% hydrogen bromide in acetic acid (4 mL), heated to 50° C. for 48, allowed to cool to ambient temperature, neutralized with concentrated ammonium hydroxide, and extracted with methylene chloride (3×). The combined organic layers were dried with sodium sulfate, filtered, and concentrated. The residue was purified by flash chromatography over silica gel (10% ethanol/ammonia saturated methylene chloride) to provide the title compound (0.10 g) as the free base which converted to the hydrochloride salt.

[α]²⁰_D −125.88° (DMSO);

MS (ESI(−)) m/z 375 (M−H)⁻;

¹H NMR (DMSO-d₆) (free base) δ 2.28 (t, 2H), 2.53–2.76 (m, 2H), 3.18 (s, 2H), 3.62 (d, 2H), 4.67 (s, 1H), 7.22 (d, 2H), 7.45 (d, 1H), 10.1 (s, 1H);

Anal. Calcd for C₁₇H₁₃N₂FBrO₂.HCl.0.5 H₂O: C, 48.43; H, 4.08; N, 6.28. Found: C, 48.42; H, 3.59; N, 6.64.

EXAMPLE 6

(+)-5-(3-bromo-4-fluorophenyl)-2,3,5,7,8,9-hexahydro-1H-cyclopenta[b][1,7]naphthyridine-4,6-dione hydrochloride A solution of the product from Example 5C (0.25 g, 0.41 mmol) in acetic acid (3 mL) was treated with 48% hydrogen bromide and was heated for 3 days at 50° C. The reaction mixture was allowed to cool to ambient temperature, neutralized with concentrated ammonium hydroxide, and extracted with methylene chloride. The combined organic phases were dried with sodium sulfate, filtered concentrated. The residue was purified by flash chromatography over silica gel (10% ethanol/ammonia saturated methylene chloride) to provide the title compound (0.070 g) as a free base which was converted to the hydrochloride salt.

[α]²⁰_D +117.64° (DMSO);

MS (ESI(−)) m/z 375 (M−H)⁻;

¹H NMR (DMSO-d₆) (free base) δ 2.28 (t, 2H), 2.52–2.65 (m, 2H), 3.18 (s, 2H), 3.52 (d, 2H), 4.68 (s, 1H), 7.2 (m, 2H), 7.43 (d, 1H), 10.1 (s, 1H);

Anal. Calcd for C₁₇H₁₃N₂FBrO₂.HCl.0.5H₂O: C, 48.43; H, 4.08; N, 6.28. Found: C, 48.83; H, 3.97; N, 6.32.

EXAMPLE 7

(−)-5-(3-bromo-4-fluorophenyl)-2,3,5,8,9,10-hexahydrobenzo-[b][1,7]naphthyridine-4,6(1H, 7H)-dione hydrochloride

EXAMPLE 7A

(1R,2S,5R)-5-methyl-2-(1-methyl-1-phenylethyl)cyclohexyl 5-(3-bromo-4-fluorophenyl)-4,6-dioxo-3,4,5,6,7,8,9,10-octahydrobenzo[b][1,7]naphthyridine-2(1H)-carboxylate The product from Example 2A (1.23 g, 2.5 mmol) was treated according to the method described for Example 5B. The diastereomeric mixture was subjected to column chromatography over silica gel (4:1 ethyl acetate/hexanes) to provide both the title compound as the less polar diastereomer (0.32 g) and the more polar diastereomer (0.30 g).

MS (ESI(−)) m/z 649 (M−H)⁻;

¹H NMR (CDCl₃) δ 0.88 (d, 3H), 0.9 (m, 1H), 1.13 (m, 1H), 1.19 (s, 3H), 1.28 (m, 2H), 1.32 (s, 3H), 1.72 (m, 2H), 1.88 (m, 1H), 2.05 (m, 3H); 2.38 (m, 2H), 2.51 (m, 2H), 2.72 (d, 1H), 3.56 (d, 1H), 3.82 (d, 1H), 4.71 (m, 2H), 5.07 (s, 1H), 6.92 (t, 1H), 7.12 (m, 1H), 7.28 (m, 6H).

EXAMPLE 7B

(1R,2S,5R)-5-methyl-2-(1-methyl-1-phenylethyl)cyclohexyl 5-(3-bromo-4-fluorophenyl)-4,6-dioxo-3,4,5,6,7,8,9,10-octahydrobenzo[b][1,7]naphthyridine-2(1H)-carboxylate The more polar diastereomer from Example 7A (0.30 g) was crystallized from methylene chloride/ether to provide the title compound (0.24 g).

MS (ESI(−)) m/z 649 (M−H)⁻;

¹H NMR (CDCl₃) δ 0.88 (d, 3H), 0.92 (m, 1H), 1.13 (s, 3H), 1.18–1.32 (m, 6H), 1.73 (m, 2H), 1.92 (m, 1H), 2.05 (m, 3H), 2.38 (m, 2H); 2.53 (m, 2H), 2.81 (d, 1H), 3.2 (d, 1H), 3.9 (d, 1H), 4.56 (d, 1H), 4.75 (m, 1H), 5.1 (s, 1H), 6.41 (t, 1H), 6.8 (m, 2H), 7.05 (m, 1H), 7.12 (d, 1H), 7.31 (m, 1H), 7.4 (m, 1H), 7.5 (d, 1H).

EXAMPLE 7C

(−)-5-(3-bromo-4-fluorophenyl)-2,3,5,8,9,10-hexahydrobenzo[b][1,7]naphthyridine-4,6-(1H,7H)-dione hydrochloride The product from Example 7A (0.32 g) was treated according to the method described for Example 5D to provide the title compound (0.125 g) as the free base which was then converted to the hydrochloride salt.

[α]²⁰_D −10° (CH₃CN);

MS (ESI(−)) m/z 389 (M−H)⁻;

¹H NMR (DMSO-d₆) (free base) δ 1.72–1.99 (m, 2H), 2.22 (t, 2H), 2.98 (m, 1H), 3.15 (s, 2H), 3.4 (m, 2H), 3.57 (s, 2H), 4.88 (s, 1H), 7.18 (m, 2H), 7.4 (d, 1H);

Anal. Calcd for C₁₈H₁₅BrFN₂O₂.HCl: C, 50.67; H, 3.78; N, 6.57. Found: C, 50.18; H, 4.22; N, 6.16.

EXAMPLE 8

(+)-5-(3-bromo-4-fluorophenyl)-2,3,5,8,9,10-hexahydrobenzo[b][1,7]naphthyridine-4,6(1H,7H)-dione hydrochloride The product from Example 7B (0.24 g) was treated according to the method described for Example 5D to provide the title compound (0.070 g) as the free base which was converted to the hydrochloride salt.

[α]²⁰_D +9.52° (CH₃CN);

MS (ESI(−)) m/z 389 (M−H)⁻;

¹H NMR (DMSO-d₆) δ 1.75–1.98 (m, 2H), 2.25 (t, 2H), 2.95 (s, 1H), 3.15 (s, 2H), 3.45 (m, 2H), 3.57 (s, 2H), 4.89 (s, 1H), 7.17 (m, 2H), 7.39 (d, 1H), 9.6 (s, 1H);

Anal. Calcd for C₁₈H₁₆BrFN₂O₂.HCl: C, 50.67; H, 3.78; N, 6.57. Found: C, 50.54; H, 4.05; N, 6.32.

EXAMPLE 9

10-(3-bromo-4-fluorophenyl)-3,4,6,7,8,10-hexahydro-2H-thiopyrano[3,2-b][1,7]naphthyridin-9(5H)-one 1,1-dioxide hydrochloride

EXAMPLE 9A

7-benzyl-10-(3-bromo-4-fluorophenyl)-3,4,6,7,8,10-hexahydro-2H-thiopyrano[3,2-b][1,7]naphthyridin-9(5H)-one 1,1-dioxide A solution of N-benzylpiperidine-3,5-dione (Ziegler, J. Amer. Chem. Soc. (1973), 95, 7458–7464) (0.55 g, 2.5 mmol) in ethyl alcohol (5 mL) was treated with 2.0M ammonia in ethyl alcohol (1.25 mL, 2.5 mmol), stirred for 30 minutes in a sealed tube, treated with tetrahydrothiopyran-3-one-1,1-dioxide (0.36 g, 2.5 mmol), treated with 3-bromo-4-fluorobenzaldehyde (0.51 g, 2.5 mmol), stirred at 75° for 48 hours, cooled and concentrated. The residue was purified by flash chromatography over silica gel (5% ethanol/methylene chloride) to provide the title compound (0.50 g).

MS (ESI(−)) m/z 517 (M−H)⁻;

$^1$H NMR (DMSO-d$_6$) δ 2.18 (m, 2H), 2.42 (m, 2H), 2.95 (m, 2H), 3.15 (m, 4H), 3.42 (m, 2H), 3.6 (q, 2H), 5.0 (s, 1H), 7.18–7.5 (m, 8H), 9.5 (s, 1H).

EXAMPLE 9B vinyl 10-(3-bromo-4-fluorophenyl)-9-oxo-3,4,6,8,9, 10-hexahydro-2H-thiopyrano[3,2-b][1,7] naphthyridine-7(5H)-carboxylate 1,1-dioxide A solution of the product from Example 9A 0.48 g, 0.92 mmol) in THF (5 mL) was treated with vinyl chloroformate (0.10 mL, 0.94 mmol) and stirred at ambient temperature overnight. The solvent was evaporated and the residue was purified by flash chromatography over silica gel (ethyl acetate and then 10% ethanol/methylene chloride) to provide the title compound (0.25 g).

MS (ESI(–)) m/z 497 (M–H)$^-$;

$^1$H NMR (DMSO-d$_6$) δ 2.21 (m, 2H), 2.68 (m, 2H), 3.18 (m, 2H), 3.28 (m, 2H), 3.5 (m, 1H), 3.75 (q, 2H), 4.11 (s, 2H), 5.08 (s, 1H), 7.28 (m, 2H), 7.41 (d, 1H), 9.5 (br s, 1H).

EXAMPLE 9C 10-(3-bromo-4-fluorophenyl)-3,4,6,7,8,10-hexahydro-2H-thiopyrano[3,2-b][1,7]naphthyridin-9 (5H)-one 1,1-dioxide hydrochloride A solution of the product from Example 9B (0.25 g) in ethyl alcohol was treated with 6N HCl (1 mL), refluxed for 2 hours, cooled to ambient temperature and concentrated. The residue was purified by flash chromatography over silica gel (15% ethanol/ammonia saturated methylene chloride) to provide the title compound (0.09 g) as the free base which was converted to the hydrochloride salt.

MS (ESI(–)) m/z 425 (M–H)$^-$;

$^1$H NMR (DMSO-d$_6$) (free base) δ 2.2 (m, 2H), 2.6 (m, 2H), 3.15 (s, 2H), 3.22 (m, 2H), 3.52 (d, 2H), 5.02 (s, 1H), 7.22 (m, 2H), 7.4 (m, 1H), 9.5 (br s, 1H);

Anal. Calcd for C$_{17}$H$_{16}$N$_2$FBrSO$_3$·HCl·0.5 C$_2$H$_5$OH: C, 44.41; H, 4.14; N, 5.75; Cl, 7.28. Found: C, 44.80; H, 4.16; N, 5.68; Cl, 7.40.

EXAMPLE 10

9-(3-Bromo-4-fluorophenyl)-2,3,5,6,7,9-hexahydrothieno[3,2-b][1,7]naphthyridin-8(4H)-one, 1,1-dioxide hydrochloride

EXAMPLE 10A

Tetrahydrothiophene-3-ol

A solution of tetrahydrothiophene-3-one (10.2 g, 100 mmol) in ethanol (100 mL) was treated slowly with sodium borohydride (4.3 g, 114 mmol), stirred for 1 hour at ambient temperature, concentrated to a volume of approximately 50 mL, treated with water (400 mL) and extracted with methylene chloride (3×). The combined methylene chloride layers were washed with 1N HCl, dried (MgSO$_4$), filtered, and concentrated to provide 9.0 g of the title compound as a clear oil which was carried onto the next step without purification.

EXAMPLE 10B

Tetrahydrothiophene-3-ol-1,1-dioxide

A mixture of Example 10A (10.0 g, 96.0 mmol), sodium tungstate dihydrate (0.315 g, 0.96 mmol) and acetic acid (7.5 mL, 130 mmol) in water (42 mL) at 0° C. was treated with 30% hydrogen peroxide (31.6 g, 280 mmol) dropwise over 1 hour stirred for 30 minutes at 0° C., stirred at ambient temperature for 45 minutes, transferred to a 100 mm×190 mm crystallizing dish and concentrated by heating on a steam bath to provide the title compound as an oil which was carried on to the next step without purification.

EXAMPLE 10C

Tetrahydrothiophene-3-one-1,1-dioxide

A mechanically stirred solution of the crude product from Example 10B in acetone (300 mL) was treated with Jones reagent (2.7M, 30 mL total) in portions over 2 hours until the brown color persisted, stirred for 1 hour, treated slowly with isopropyl alcohol (7.5 mL), stirred for 15 minutes, diluted with acetone (400 mL) and filtered through celite to remove the chromium salts. The filtrate was concentrated and purified by chromatography on silica gel (1:1 hexane:ethyl acetate) to provide 5.88 g of the title compound.

$^1$H NMR (CDCl$_3$) δ 3.08 (t, 2H), 3.58 (t, 2H), 3.70 (s, 2H).

EXAMPLE 10D 6-benzyl-9-(3-bromo-4-fluorophenyl)-2,3,5,6,7,9-hexahydrothieno[3,2-b][1,7]naphthyridin-8(4H)-one, 1,1-dioxide A solution of N-benzylpiperidine-3,5-dione (Ziegler, J. Amer. Chem. Soc. (1973), 95, 7458–7464) (0.55 g, 2.5 mmol) in ethyl alcohol (5 mL) was treated with 2.0M ammonia in ethyl alcohol (1.25 mL, 2.5 mmol), stirred for 4 hours in a sealed tube, treated with the product from Example 10C (0.33 g, 2.5 mmol), treated with 3-bromo-4-fluorobenzaldehyde (0.51 g, 2.5 mmol), stirred at 75° C. for 48 hours, cooled and concentrated. The residue was purified by flash chromatography over silica gel (5–10% ethanol/methylene chloride) to provide the title compound (0.28 g).]

MS (ESI(–)) m/z 501 (M–H)$^-$;

$^1$H NMR (DMSO-d$_6$) δ 2.8 (m, 1H), 3.0 (m, 2H), 3.08–3.3 (m, 2H), 3.42 (m, 3H), 3.62 (m, 2H), 4.85 (s, 1H), 7.2–7.48 (m, 8H), 9.98 (s, 1H).

EXAMPLE 10E vinyl 9-(3-bromo-4-fluorophenyl)-8-oxo-2,3,5,7,8,9-hexahydrothieno[3,2-b][1,7]naphthyridine-6(4H)-carboxylate 1,1-dioxide A solution of the product from Example 10D 0.22 g, 0.43 mmol) in methylene chloride (5 mL) was treated with vinyl chloroformate (0.10 mL, 0.94 mmol), stirred at ambient temperature overnight, diluted with methylene chloride and washed with aqueous sodium bicarbonate. The methylene chloride layer was separated, dried with sodium sulfate, filtered, and concentrated to provide the title compound (0.28 g).

MS (ESI(–)) m/z 497 (M–H)$^-$;

$^1$H NMR (DMSO-d$_6$) δ 2.88 (m, 2H), 3.1 (m, 3H), 3.5 (m, 1H), 3.75 (q, 2H), 4.12 (s, 2H), 4.9 (s, 1H), 7.29 (m, 2H), 7.48 (d, 1H), 10.1 (s, 1H).

EXAMPLE 10F 9-(3-Bromo-4-fluorophenyl)-2,3,5,6,7,9-hexahydrothieno[3,2-b][1,7]naphthyridin-8(4H)-one, 1,1-dioxide hydrochloride The product from Example 10E in ethyl alcohol (5 mL) was treated with 6N HCl (1 mL), refluxed for 3 hours, cooled to ambient temperature and concentrated. The residue was purified by flash chromatography over silica gel (10% ethanol/ammonia saturated methylene chloride) to provide the title compound (0.070 g) which was converted to the hydrochloride salt.

MS (ESI(−)) m/z 411 (M−H)⁻;

$^1$H NMR (DMSO-d$_6$) δ 2.75 (m, 2H), 3.02 (m, 1H), 3.15 (s, 2H), 3.58 (m, 3H), 4.87 (s, 1H), 7.25 (d, 2H), 7.43 (d, 1H), 9.9 (s, 1H);

Anal. Calcd for $C_{16}H_{14}BrFN_2SO_3 \cdot HCl \cdot 0.5C_2H_5OH$: C, 43.19; H, 3.84; N, 5.93; Cl, 7.50. Found: C, 43.69; H, 3.85; N, 5.83; Cl, 7.66.

EXAMPLE 11

9-(3-bromo-4-fluorophenyl)-2,3,5,9-tetrahydro-4H-pyrano[3,4-b]thieno[2,3-e]pyridin-8(7H)-one 1,1-dioxide

EXAMPLE 11A methyl (2-oxopropoxy)acetate

A solution of 2M dimethyl zinc in toluene (21 mL, 42 mmol) was cooled to 0° C. under nitrogen, treated with trans-benzyl(chloro)bis(triphenylphosphine)palladium(II) (0.57 g, 76 mmol), treated with methyl 2-(chloroformylmethoxy)acetate (12.6 g, 76 mmol) dropwise over 0.5 hours, stirred for 0.5 hours at 0° C., stirred for 16 hours at ambient temperature, treated with 1M HCl (40 mL) and then brine (20 mL). The organic layer was dried (MgSO$_4$), filtered and concentrated. The residue was purified by flash chromatography over silica gel (1:2 ethyl acetate/hexanes) to provide the title compound (5.2 g).

EXAMPLE 11B 2H-pyran-3,5(4H,6H)-dione

A solution of the product from Example 11A (5.0 g, 34 mmol) in diethyl ether (40 mL) was added dropwise over 2.5 hours to a 0° solution of 1M potassium tert-butoxide (in tert-butanol, 34 mL) in diethyl ether (270 mL). The mixture was treated with 1M HCl (120 mL) followed by ethyl acetate (250 mL) and brine (50 mL). The layers were separated and the aqueous layer was extracted with ethyl acetate (twice, 250 mL). The combined organic layers were washed with brine (2×, 60 mL), dried (MgSO$_4$), filtered and concentrated (keeping the temperature below 40° C.) to provide the title compound (Terasawa, J. Org. Chem. (1977), 42, 1163–1169) in approximately 30% purity which can be further purified by chromatography on silica gel using 200:1:1:100 ethyl acetate:formic acid:water:hexane to provide the title compound.

EXAMPLE 11C 5H-amino-2H-pyran-3(6H)-one

The 30% pure product of Example 11B was treated with benzene (60 mL), then ethanol (20 mL), then para-toluenesulfonic acid (100 mg), and then heated to reflux for 6 hours and concentrated. The obtained product, 5-ethoxy-2H-pyran-3(6H)-one, was treated with 2M ammonia in methanol (100 mL), stirred for 16 hours and concentrated. The residue was purified by flash chromatography over silica gel (5% and then 10% methanol/methylene chloride) to provide the title compound (1.3 g).

MS (DCI/NH$_3$) m/z 114 (M+H)⁺, 131 (M+NH$_4$)⁺;

$^1$H NMR (DMSO-d$_6$) δ 3.80 (s, 2H), 4.19 (s, 2H), 5.01 (s, 1H), 7.01 (bs, 2H).

EXAMPLE 11D 9-(3-bromo-4-fluorophenyl)-2,3,5,9-tetrahydro-4H-pyrano[3,4-b]thieno[2,3-e]pyridin-8(7H)-one 1,1-dioxide A mixture of the product from Example 11C (1.5 g, 13 mmol), 3-bromo-4-fluorobenzaldehyde (3.2 g, 16 mmol), tetrahydrothiophene-3-oxo-1,1-dioxide prepared as described in (J. Heterocycl. Chem., v. 27 pp. 1453 (1990)) (1.8 g, 13 mmol) and triethylamine (0.93 mL, 6.6 mmol) in ethanol (20 mL) was stirred in a sealed tube at 80° C. for 60 hours, cooled and concentrated to dryness. The residue was treated with ethanol (50 mL), then 1 M HCl (in diethyl ether, 5 mL), and heated to reflux for 5 minutes and kept at ambient temperature for 3 hours. The resulting solid was collected by filtration, washed with ethanol and dried under vacuum for 16 hours to provide the title compound (3.2 g) mp>260° C.;

MS (ESI(+)) m/z 414 (M+H)⁺, 431 (M+NH$_4$)⁺;

MS (ESI(−)) m/z 412 (M−H)⁻;

$^1$H NMR (DMSO-d$_6$) δ 2.85 (m, 1H), 3.08 (m, 1H), 3.33–3.42 (m, 2H), 4.03 (s, 2H), 4.49 (AB q, 2H), 4.90 (s, 1H), 7.27 (m, 2H), 7.45 (dd, 1H), 10.14 (s, 1H);

Anal. Calcd for $C_{16}H_{13}NO_4SFBr$: C, 46.39; H, 3.16; N, 3.38. Found: C, 46.25; H, 3.24; N, 3.26.

EXAMPLE 12

(−)-9-(3-bromo-4-fluorophenyl)-2,3,5,9-tetrahydro-4H-pyrano[3,4-b]thieno[2,3-e]pyridin-8(7H)-one 1,1-dioxide

EXAMPLE 12A (1R,2S,5R)-5-methyl-2-(1-methyl-1-phenylethyl) cyclohexyl 9-(3-bromo-4-fluorophenyl)-8-oxo-2,3,5,7,8,9-hexahydro-4H-pyrano[3,4-b]thieno[2,3-e] pyridine-4-carboxylate 1,1-dioxide To a suspension of the product from Example 11D (1.58 g, 3.7 mmol) in THF (40 mL) at 0° C. under a nitrogen atmosphere was added a 1M solution of potassium tert-butoxide in THF (4.1 mL) dropwise over 5 minutes. The mixture was stirred at ambient temperature for 30 minutes, cooled to 0° C., treated with a solution of 8-phenylmenthol chloroformate prepared from (−)-8-phenylmenthol as described in (Yamamoto, Y., J. Amer. Chem. Soc. (1992), 114, 121–125) (1.31 g, 4.4 mmol) in THF (20 mL) over 5 minutes, stirred at ambient temperature for 16 hours, diluted with methylene chloride (150 mL) and washed with aqueous sodium bicarbonate (30 mL). The layers were separated and the aqueous layer was extracted with methylene chloride (50 mL). The combined organic layers were dried (MgSO$_4$), filtered and concentrated. The residue was purified by flash chromatography over silica gel (3:2:1 chloroform/hexanes/diethyl ether) to provide 0.98 g of the less polar diasteriomer.

MS (ESI(+)) m/z 672 (M+H)⁺, 689 (M+NH$_4$)⁺;

MS (ESI(−)) m/z 670 (M−H)⁻.

EXAMPLE 12B (1R,2S,5R)-5-methyl-2-(1-methyl-1-phenylethyl) cyclohexyl 9-(3-bromo-4-fluorophenyl)-8-oxo-2,3,5,7,8,9-hexahydro-4H-pyrano[3,4-b]thieno[2,3-e] pyridine-4-carboxylate 1,1-dioxide The impure more polar diasteriomer from Example 12A was rechromatographed on silica gel gel (3:2:1 chloroform/hexanes/diethyl ether) to provide 1.0 g of pure more polar diasteriomer.

MS (ESI(+)) m/z 672 (M+H)$^+$, 689 (M+NH$_4$)$^+$;
MS (ESI(−)) m/z 670 (M−H)$^−$.

EXAMPLE 12C (+)-9-(3-bromo-4-fluorophenyl)-2,3,5,9-tetrahydro-4H-pyrano[3,4-b]thieno[2,3-e]pyridin-8(7H)-one 1,1-dioxide A solution of Example 12A (0.98 g, 1.4 mmol) in methanol/methylene chloride (40 mL/10 mL) was degassed with nitrogen, treated with of 25% sodium methoxide in methanol (30 drops), stirred for 16 hours, filtered through a 45 mm syringe filter and concentrated to a volume of 5 mL of methanol. The solid which had precipitated was collected by filtration, washed with methanol and dried under vacuum for 16 hours to provide the title compound (0.36 g).

$[\alpha]^{20}{}_D$+117° (DMSO, c 0.925);
MS (ESI(+)) m/z 414 (M+H)$^+$, 431 (M+NH$_4$)$^+$;
MS (ESI(−)) m/z 412 (M−H)$^−$;
$^1$H NMR (DMSO-d$_6$) δ 2.85 (m, 1H), 3.08 (m, 1H), 3.33–3.42 (m, 2H), 4.03 (s, 2H), 4.49 (AB q, 2H), 4.90 (s, 1H), 7.27 (m, 2H), 7.45 (dd, 1H), 10.14 (s, 1H);
Anal. Calcd for C$_{16}$H$_{13}$NO$_4$SFBr: C, 46.39; H, 3.16; N, 3.38. Found: C, 46.07; H, 3.02; N, 3.19.

EXAMPLE 13

(−)-9-(3-bromo-4-fluorophenyl)-2,3,5,9-tetrahydro-4H-pyrano[3,4-b]thieno[2,3-e]pyridin-8(7H)-one 1,1-dioxide A solution of Example 12B (1.0 g, 15 mmol) was processed as described in Example 12C to provide the title compound (0.40 g).

$[\alpha]^{20}{}_D$−117° (DMSO, c 1.01);
MS (ESI(+)) m/z 414 (M+H)$^+$, 431 (M+NH$_4$)$^+$;
MS (ESI(−)) m/z 412 (M−H)$^−$;
$^1$H NMR (DMSO-d$_6$) δ 2.85 (m, 1H), 3.08 (m, 1H), 3.33–3.42 (m, 2H), 4.03 (s, 2H), 4.49 (AB q, 2H), 4.90 (s, 1H), 7.27 (m, 2H), 7.45 (dd, 1H), 10.14 (s, 1H);
Anal. Calcd for C$_{16}$H$_{13}$NO$_4$SFBr: C, 46.39; H, 3.16; N, 3.38. Found: C, 46.12; H, 3.23; N, 3.34.

EXAMPLE 14

9-(3-cyanophenyl)-2,3,5,9-tetrahydro-4H-pyrano[3,4-b]thieno[2,3-e]pyridin-8(7H)-one 1,1-dioxide A mixture of the product from Example 11C (0.74 g, 6.5 mmol), 3-cyanobenzaldehyde (1.0 g, 7.8 mmol), tetrahydrothiophene-3-oxo-1,1-dioxide (0.87 g, 6.5 mmol) and triethylamine (0.45 mL, 3.2 mmol) in ethanol (20 mL) was stirred in a sealed tube for 60 hours, cooled and the solid collected by filtration and washed with ethanol. The solid was treated with ethanol (30 mL) and 1M HCl (in diethyl ether, 4 mL), heated to reflux for 15 minutes and kept at ambient temperature for 16 hours. The title compound (1.4 g) was collected by filtration, washed with ethanol and dried under vacuum for 16 hours.

MS (ESI(+)) m/z 360 (M+NH$_4$)$^+$;
MS (ESI(−)) m/z 341 (M−H)$^−$;
$^1$H NMR (DMSO-d$_6$) δ 2.86 (m, 1H), 3.09 (m, 1H), 3.38 (m, 2H), 4.02 (s, 2H), 4.49 (AB q, 2H), 4.97 (s, 1H), 7.49 (t, 1H), 7.56–7.68 (m, 3H), 10.14 (s, 1H);
Anal. Calcd for C$_{17}$H$_{14}$N$_2$O$_4$S.0.25 EtOH: C, 59.4; H, 4.41; N, 7.92. Found: C, 59.19; H, 4.40; N, 7.88.

EXAMPLE 15

(+) 9-(3-cyanophenyl)-2,3,5,9-tetrahydro-4H-pyrano[3,4-b]thieno[2,3-e]pyridin-8(7H)-one 1,1-dioxide

EXAMPLE 12A (1S,2R,5S)-5-methyl-2-(1-methyl-1-phenylethyl)cyclohexyl 9-(3-cyanophenyl)-8-8-oxo-2,3,5,7,8,9-hexahydro-4H-pyrano[3,4-b]thieno[2,3-e]pyridine-4-carboxylate 1,1-dioxide The product from Example 14 (1.3 g, 3.8 mmol) was processed as in Example 12A and 12B to provide 0.50 g of the less polar diasteriomer and 0.50 g of the more polar diasteriomer.

(less polar diasteromer)
MS (ESI(+)) m/z 618 (M+NH$_4$)$^+$;
MS (ESI(−)) m/z 599 (M−H)$^−$;
(more polar diasteromer)
MS (ESI(+)) m/z 618 (M+NH$_4$)$^+$;
MS (ESI(−)) m/z 599 (M−H)$^−$.

EXAMPLE 15B (+) 9-(3-cyanophenyl)-2,3,5,9-tetrahydro-4H-pyrano[3,4-b]thieno[2,3-e]pyridin-8(7H)-one 1,1-dioxide A suspension of the less polar diasteriomer from Example 15A (0.50 g, 0.83 mmol) in methanol (10 mL) was treated with 25% sodium methoxide in methanol (30 drops), stirred for 16 hours, filtered through a 45 mm syringe filter, concentrated to dryness, treated with ethanol (20 mL), heated on a steam bath until crystallization began and allowed to stand at ambient temperature for 5 hours. The solid was collected by filtration, washed with ethanol and dried under vacuum for 16 hours to provide the title compound (0.15 g).

$[\alpha]^{20}{}_D$−105° (DMSO, c 1.0);
MS (ESI(+)) m/z 360 (M+NH$_4$)$^+$;
MS (ESI(−)) m/z 341 (M−H)$^−$;
$^1$H NMR (DMSO-d$_6$) δ 2.86 (m, 1H), 3.09 (m, 1H), 3.38 (m, 2H), 4.02 (s, 2H), 4.49 (AB q, 2H), 4.97 (s, 1H), 7.49 (t, 1H), 7.56–7.68 (m, 3H), 10.14 (s, 1H);
Anal. Calcd for C$_{17}$H$_{14}$N$_2$O$_4$S: C, 59.64; H, 4.12; N, 8.18. Found: C, 59.39; H, 4.25; N, 7.80.

EXAMPLE 16

(−) 9-(3-cyanophenyl)-2,3,5,9-tetrahydro-4H-pyrano[3,4-b]thieno[2,3-e]pyridin-8(7H)-one 1,1-dioxide A suspension of the more polar diasteriomer for Example 15A (0.50 g, 0.83 mmol) in methanol (30 mL) and methylene chloride (5 mL) was treated with 25% sodium methoxide in methanol (10 drops), stirred for 16 hours, filtered through a 45 mm syringe filter, treated dropwise with acetic acid until the yellow color disappeared, concentrated to dryness, treated with ethanol (30 mL), heated on a steam bath until crystallization began and allowed to stand ambient temperature for 5 hours. The solid was collected by filtration, washed with ethanol and dried under vacuum for 16 hours to provide the title compound (0.18 g).

$[\alpha]^{20}{}_D$−103° (DMSO, c 1.0);
MS (ESI(+)) m/z 360 (M+NH$_4$)$^+$;
MS (ESI(−)) m/z 341 (M−H)$^−$;
$^1$H NMR (DMSO-d$_6$) δ 2.86 (m, 1H), 3.09 (m, 1H), 3.38 (m, 2H), 4.02 (s, 2H), 4.49 (AB q, 2H), 4.97 (s, 1H), 7.49 (t, 1H), 7.56–7.68 (m, 3H), 10.14 (s, 1H);

Anal. Calcd for C$_{17}$H$_{14}$N$_2$O$_4$S.0.5 H$_2$O: C, 58.86; H, 4.21; N, 8.08. Found: C, 58.90; H, 4.48; N, 7.80.

EXAMPLE 17

9-(4-chloro-3-nitrophenyl)-2,3,5,9-tetrahydro-4H-pyrano[3,4-b]thieno[2,3-e]pyridin-8(7H)-one 1,1-dioxide A mixture of the product from Example 11C (0.74 g, 6.5 mmol), 4-chloro-3-nitrobenzaldehyde (1.5 g, 7.8 mmol), tetrahydrothiophene-3-oxo-1,1-dioxide (0.87 g, 6.5 mmol) and triethylamine (0.45 mL, 3.2 mmol) in ethanol (20 mL) was processed as in Example 11D yielding a residue which was purified by flash chromatography over silica gel (5% methanol/methylene chloride) and crystallized from ethanol to provide the title compound (1.46 g).
MS (ESI(+)) m/z 414 (M+NH$_4$)$^+$;
MS (ESI(-)) m/z 395 (M-H)$^-$;
$^1$H NMR (DMSO-d$_6$) δ 2.80–2.93 (m, 1H), 3.01–3.13 (m, 1H), 3.39 (t, 2H), 4.04 (s, 2H), 4.49 (AB q, 2H), 5.02 (s, 1H), 7.58 (dd, 1H), 7.69 (d, 1H), 7.86 (d, 1H), 10.22 (s, 1H);
Anal. Calcd for C$_{16}$H$_{13}$N$_2$O$_6$SCl: C, 48.43; H, 3.30; N, 7.06. Found: C, 48.13; H, 3.38; N, 6.79.

EXAMPLE 18

(+)-9-(4-chloro-3-nitrophenyl)-2,3,5,9-tetrahydro-4H-pyrano[3,4-b]thieno[2,3-e]pyridin-8(7H)-one 1,1-dioxide

EXAMPLE 18A (1R,2S,5R)-5-methyl-2-(1-methyl-1-phenylethyl)cyclohexyl 9-(4-chloro-3-nitrophenyl)-8-oxo-2,3,5,7,8,9-hexahydro-4H-pyrano[3,4-b]thieno[2,3-e]pyridine-4-carboxylate 1,1-dioxide The product from Example 17 (1.3 g, 3.3 mmol) was processed as in Example 12A and 12B to provide 0.71 g of the less polar disteriomer and 0.81 g of the more polar diasteriomer.
(less polar diasteromer)
MS (ESI(+)) m/z 672 (M+NH$_4$)$^+$;
MS (ESI(-)) m/z 653 (M-H)$^-$;
(more polar diasteromer)
MS (ESI(+)) m/z 672 (M+NH$_4$)$^+$;
MS (ESI(-)) m/z 653 (M-H)$^-$;

EXAMPLE 18B (+)-9-(4-chloro-3-nitrophenyl)-2,3,5,9-tetrahydro-4H-pyrano[3,4-b]thieno[2,3-e]pyridin-8(7H)-one 1,1-dioxide The less polar diasteriomer from Example 18A (0.71 g, 1.1 mmol) was processed as in Example 16 to provide the title compound (0.23 g).
$[α]^{20}_D$+75° (c=1.0, DMSO);
MS (ESI(-)) m/z 395 (M-H)$^-$;
$^1$H NMR (DMSO-d$_6$) δ 2.80–2.93 (m, 1H), 3.01–3.13 (m, 1H), 3.39 (t, 2H), 4.04 (s, 2H), 4.49 (AB q, 2H), 5.02 (s, 1H), 7.58 (dd, 1H), 7.69 (d, 1H), 7.86 (d, 1H), 10.22 (s, 1H);
Anal. Calcd for C$_{16}$H$_{13}$N$_2$O$_6$SCl: C, 48.43; H, 3.30; N, 7.06. Found: C, 48.26; H, 3.48; N, 6.98.

EXAMPLE 19

(-)-9-(4-chloro-3-nitrophenyl)-2,3,5,9-tetrahydro-4H-pyrano[3,4-b]thieno[2,3-e]pyridin-8(7H)-one 1,1-dioxide The more polar diasteriomer from Example 18A (0.81 g, 1.2 mmol) was processed as in Example 16 to provide the title compound (0.29 g).
$[α]^{20}_D$-74° (DMSO, c 0.97);
MS (ESI(+)) m/z 414 (M+NH$_4$)$^+$;
MS (ESI(-)) m/z 395 (M-H)$^-$;
$^1$H NMR (DMSO-d$_6$) δ 2.80–2.93 (m, 1H), 3.01–3.13 (m, 1H), 3.39 (t, 2H), 4.04 (s, 2H), 4.49 (AB q, 2H), 5.02 (s, 1H), 7.58 (dd, 1H), 7.69 (d, 1H), 7.86 (d, 1H), 10.22 (s, 1H);
Anal. Calcd for C$_{16}$H$_{13}$N$_2$O$_6$SCl: C, 48.43; H, 3.30; N, 7.06. Found: C, 48.42; H, 3.31; N, 6.91.

EXAMPLE 20

5-(3-bromo-4-fluorophenyl)-5,8,9,10-tetrahydro-1H-pyrano[3,4-b]quinoline-4,6(3H,7H)-dione A mixture of the product from Example 11C (0.23 g, 2.0 mmol), 3-bromo-4-fluorobenzaldehyde (0.49 g, 2.4 mmol), 1,3-cyclohexanedione (0.23 g, 2.0 mmol) and triethylamine (0.14 mL, 1.0 mmol) in ethanol (4 mL) was stirred at 80° C. in a sealed tube for 60 hours and cooled to ambient temperature. The resulting solid was collected by filtration, washed with ethanol, dissolved in a mixture of methylene chloride/methanol (4:1); heated on a steam bath to remove the methylene chloride and allowing to crystallize for 4 hours. The crystals were collected by filtration, washed with methanol and dried under vacuum for 16 hours to provide the title compound (0.37 g).
MS (ESI(+)) m/z 392 (M+NH$_4$)$^+$;
MS (ESI(-)) m/z 390 (M-H)$^-$;
$^1$H NMR (DMSO-d$_6$) δ 1.76–2.01 (m, 2H), 2.25 (t, 2H), 2.43–2.64 (m, 2H), 4.01 (s, 2H), 4.48 (AB q, 2H), 4.90 (s, 1H), 7.20 (m, 2H), 7.39 (dd, 1H), 9.82 (bs, 1H);
Anal. Calcd for C$_{18}$H$_{15}$HO$_3$FBr: C, 55.12; H, 3.85; N, 3.57. Found: C, 54.99; H, 4.04; N, 3.49.

EXAMPLE 21

10-(3-bromo-4-fluorophenyl)-3,4,6,10-tetrahydro-2H,5H-pyrano[3,4-b]thiopyrano[2,3-e]pyridin-9(8H)-one 1,1-dioxide A mixture of the product from Example 11C (0.23 g, 2.0 mmol), 3-bromo-4-fluorobenzaldehyde (0.49 g, 2.4 mmol), 1,1-dioxotetrahydro-1-thiopyran-3-one (Dodd, J. H., J. Heterocyclic Chem., (1990), 27, 1453–1456) (0.30 g, 2.0 mmol) and triethylamine (0.14 mL, 1.0 mmol) in ethanol (4 mL) was processed as described in Example 14 to provide the title compound (0.25 g).
MS (ESI(+)) m/z 428 (M+H)$^+$, 445 (M+NH$_4$)$^+$;
MS (ESI(-)) m/z 426 (M-H)$^-$;
$^1$H NMR (DMSO-d$_6$) δ 2.22 (m, 2H), 2.41–2.56 (m, 1H), 2.64 (dt, 1H), 3.09–3.35 (m, 2H), 4.02 (s, 2H), 4.43 (AB q, 2H), 5.06 (s, 1H), 7.25 (m, 2H), 7.41 (dd, 1H), 9.67 (bs, 1H);
Anal. Calcd for C$_{17}$H$_{15}$NO$_4$SFBr: C, 47.68; H, 3.53; N, 3.27. Found: C, 47.36; H, 3.65; N, 3.06.

EXAMPLE 22

5-(3-bromo-4-fluorophenyl)-5,10-dihydro-1H,3H-pyrano[3,4-b]thiopyrano[4,3-e]pyridine-4,6(7H,9H)-dione A mixture of the product from Example 11C (0.23 g, 2.0 mmol), 3-bromo-4-fluorobenzaldehyde (0.49 g, 2.4 mmol), thiopyran-3,5-dion (Fehnel, E. A., J. Amer. Chem. Soc., (1955), 77, 4241–4244) (0.26 g, 2.0 mmol) and triethylamine (0.14 mL, 1.0 mmol) in ethanol (4 mL) was processed as in Example 20 to provide the title compound (0.37 g).

MS (ESI(+)) m/z 410 (M+H)$^+$, 427 (M+NH$_4$)$^+$;
MS (ESI(−)) m/z 408 (M−H)$^-$;
$^1$H NMR (DMSO-d$_6$) δ 3.12 (d, 1H), 3.50 (d, 2H), 3.81 (dd, 1H), 4.03 (s, 2H), 4.48 (AB q, 2H), 4.97 (s, 1H), 7.20 (ddd, 1H), 7.26 (t, 1H), 7.40 (dd, 1H), 9.98 (bs, 1H);
Anal. Calcd for C$_{17}$H$_{13}$NO$_3$SFBr: C, 49.77; H, 3.19; N, 3.41. Found: C, 49.43; H, 3.28; N, 3.21.

EXAMPLE 23

5-(3-bromo-4-fluorophenyl)-5,7,8,9-tetrahydrocyclopenta[b]pyrano[4,3-e]pyridine-4,6(1H,3H)-dione A mixture of the product from Example 11C (0.23 g, 2.0 mmol), 3-bromo-4-fluorobenzaldehyde (0.49 g, 2.4 mmol), 1,3-cyclopentanedione (0.20 g, 2.0 mmol) and triethylamine (0.14 mL, 1.0 mmol) in ethanol (4 mL) was processed as described in Example 14. The solid was dissolved in a mixture of methylene chloride/methanol (4:1), heated on a steam bath to remove the methylene chloride and allowing to crystallize for 4 hours. The crystals were collected by filtration, washed with methanol and dried under vacuum for 16 hours to provide the title compound (0.14 g).
MS (ESI(+)) m/z 378 (M+H)$^+$, 395 (M+NH$_4$)$^+$;
MS (ESI(−)) m/z 376 (M−H)$^-$;
$^1$H NMR (DMSO-d$_6$) δ 2.31 (t, 2H), 2.59 (dt, 1H), 2.73 (dt, 1H), 4.04 (s, 2H), 4.53 (AB q, 2H), 4.71 (s, 1H), 7.22 (m, 2H), 7.43 (dd, 1H), 10.36 (bs, 1H);
Anal. Calcd for C$_{17}$H$_{13}$NO$_3$FBr: C, 53.99; H, 3.46; N, 3.70. Found: C, 53.68; H, 3.63; N, 3.63.

EXAMPLE 24

5-(3-bromo-4-fluorophenyl)-5,8,9,10-tetrahydro-1H-pyrano[3,4-b][1,7]naphthyridine-4,6(3H,7H)-dione hydrochloride

EXAMPLE 24A 8-benzyl-5-(3-bromo-4-fluorophenyl)-5,8,9,10-tetrahydro-1H-pyrano[3,4-b][1,7]naphthyridine-4,6(3H,7H)-dione A mixture of the product from Example 11C (0.13 g, 1.1 mmol), 3-bromo-4-fluorobenzaldehyde (0.28 g, 1.4 mmol), N-benzylpiperidine-3,5-dione (Ziegler, J. Amer. Chem. Soc. (1973), 95, 7458–7464) (0.23 g, 1.1 mmol) and triethylamine (0.14 mL, 1.0 mmol) in ethanol (3 mL) was processed as in Example 2A to provide the title compound (0.35 g).
MS (ESI(+)) m/z 483 (M+H)$^+$, 505 (M+NH$_4$)$^+$;
MS (ESI(−)) m/z 481 (M−H)$^-$.

EXAMPLE 24B vinyl 5-(3-bromo-4-fluorophenyl)-4,6-dioxo-4,5,6,7,9,10-hexahydro-1H-pyrano[3,4-b][1,7]naphthyridine-8(3H)-carboxylate A solution of the product from Example 24A (0.29 g, 0.69 mmol) in methylene chloride (4 mL) was treated with vinyl chloroformate (0.10 mL, 1.2 mmol) and processed as in Example 2B. Purification by flash chromatography over silica gel (EtOAc) provided the title compound (0.13 g).
MS (ESI(+)) m/z 463 (M+H)$^+$, 480 (M+NH$_4$)$^+$;
MS (ESI(−)) m/z 461 (M−H)$^-$.

EXAMPLE 24C 5-(3-bromo-4-fluorophenyl)-5,8,9,10-tetrahydro-1H-pyrano[3,4-b][1,7]naphthyridine-4,6(3H,7H)-dione hydrochloride A solution of Example 24B in ethanol (10 mL) was treated with 6N HCl (5 mL), refluxed for 3 hours and concentrated. Purification by flash chromatography over silica gel (10% methanol/ammonia saturated methylene chloride) provided the title compound (0.080 g) which was converted to the hydrochloride salt.
mp 232–235° C.;
MS (ESI(+)) m/z 393 (M+H)$^+$, 410 (M+NH$_4$)$^+$;
MS (ESI(−)) m/z 391 (M−H)$^-$;
$^1$H NMR (DMSO-d$_6$) δ 3.78 (AB q, 2H), 4.07 (s, 2H), 4.19 (s, 2H), 4.54 (AB q, 2H), 4.95 (s, 1H), 7.27 (m, 2H), 7.46 (dd, 1H), 9.86 (bs, 2H), 10.71 (s, 1H);
Anal. Calcd for C$_{17}$H$_{14}$N$_2$O$_3$FBrH$_2$O0.25EtOH: C, 45.77; H, 4.06; N, 6.10. Found: C, 45.89; H, 4.23; N, 5.91.

EXAMPLE 25

9-(3-bromo-4-fluorophenyl)-5,9-dihydro-3H-furo[3,4-b]pyrano[4,3-e]pyridine-1,8(4H,7H)-dione

EXAMPLE 25A methyl 4-(3-bromo-4-fluorophenyl)-2-methyl-5-oxo-4,5,6,8-tetrahydro-1H-pyrano[3,4-b]pyridine-3-carboxylate A mixture of tetrahydropyran-3,5-dione (Terasawa, J. Org. Chem. (1977), 42, 1163–1169) (1.4 g, 12 mmol), 3-bromo-4-fluorobenzaldehyde (3.0 g, 15 mmol), methyl 3-aminocrotonate (1.4 g, 12 mmol) and ethyl alcohol (10 mL) was processed as described in Example 2A. Purification by flash chromatography over silica gel (1% then 2% and then 5% methyl alcohol/methylene chloride) provided the title compound (2.4 g) as a solid.
mp 206–208.

EXAMPLE 25B methyl 4-(3-bromo-4-fluorophenyl)-2-(bromomethyl)-5-oxo-4,5,6,8-tetrahydro-1H-pyrano[3,4-b]pyridine-3-carboxylate A solution of the product from Example 25A (0.87 g, 2.2 mmol) in chloroform (10 mL) was cooled to −10° C., treated with pyridine (0.21 mL, 2.6 mmol), then treated with pyridinium tribromide (0.84 g, 2.6 mmol), stirred for 1 hour, diluted with methylene chloride (150 mL) and washed with 1N HCl (25 mL). The organic layer was dried (MgSO$_4$), filtered and concentrated. The residue was purified by flash chromatography over silica gel (1% and then 2% methanol/methylene chloride) to provide the title compound (0.68 g) as an oil.

EXAMPLE 25C 9-(3-bromo-4-fluorophenyl)-5,9-dihydro-3H-furo[3,4-b]pyrano[4,3-e]pyridine-1,8(4H,7H)-dione The product from Example 25B (0.30 g, 0.63 mmol) was heated neat to 130° C. for 15 minutes and cooled to ambient temperature. The residue was treated with methylene chloride and the resulting solid was collected by filtration, washed with methylene chloride and dried to provide the title compound (0.074 g) as a white solid.
166–168° C.;
MS (ESI(+)) m/z 380 (M+H)$^+$, 397 (M+NH$_4$)$^+$;
MS (ESI(−)) m/z 378 (M−H)$^-$;
$^1$H NMR (DMSO-d$_6$) δ 4.06 (s, 2H), 4.54 (AB q, 2H), 4.75 (s, 1H), 4.88 (d, 1H), 5.03 (d, 1H), 7.28 (d, 2H), 7.48 (d, 1H), 10.50 (s, 1H);
Anal. Calcd for C$_{16}$H$_{11}$NO$_4$FBr: C, 50.55; H, 2.92; N, 3.68. Found: C, 50.28; H, 3.03; N, 3.61.

EXAMPLE 26

9-(3-bromo-4-fluorophenyl)-2-methyl-2,3,5,9-tetrahydropyrano[3,4-b]pyrrolo[3,4-e]pyridine-1,8(4H,7H)-dione A solution of the product from Example 25B (0.16 g, 0.34 mmol) and 2M methyl amine in methanol (3.5 mL, 7.0 mmol) was stirred at ambient temperature for 16 hours and concentrated. Purification of the residue on silica gel (5% and then 10% methanol in methylene chloride) provided an oil which was crystallized from ethanol, collected by filtration and dried to yield the title compound (0.016 g) as a white solid.
MS (ESI(+)) m/z 393 (M+H)$^+$;
MS (ESI(−)) m/z 391 (M−H)$^−$;
$^1$H NMR (DMSO-d$_6$) δ 2.81 (s, 3H), 3.98 (d, 1H), 4.03 (s, 2H), 4.15 (d, 1H), 4.50 (AB q, 2H), 4.75 (s, 1H), 7.23 (m, 2H), 7.46 (dd, 1H), 10.11 (s, 1H);
Anal. Calcd for $C_{17}H_{14}N_2O_3FBr0.5\ H_2O$: C, 50.76; H, 3.76; N, 6.96. Found: C, 50.64; H, 3.66; N, 6.59.

EXAMPLE 27

9-(3-bromo-4-fluorophenyl)-2,3,5,9-tetrahydropyrano[3,4-b]pyrrolo[3,4-e]pyridine-1,8(4H,7H)-dione The product from Example 25B (0.22 g, 0.46 mmol) was treated with 1:1 ammonia/methanol mixture (60 mL) in a metal Parr stirred reactor for 2.5 days at ambient temperature. The solvent was allowed to evaporate and the residue was purified by chromatography on silica gel (5% and then 10% methanol in methylene chloride) to provide the title compound (0.026 g) as a solid.
ms>260° C.;
MS (ESI(+)) m/z 379 (M+H)$^+$, 396 (M+NH$_4$)$^+$;
MS (ESI(−)) m/z 3.77 (M−H)$^−$;
$^1$H NMR (DMSO-d$_6$) δ 3.90 (d, 1H), 4.03 (s, 2H), 4.07 (d, 1H), 4.50 (AB q, 2H), 4.75 (s, 1H), 7.19–7.29 (m, 2H), 7.44 (dd, 1H), 7.59 (s, 1H), 10.09 (s, 1H);
Anal. Calcd for $C_{16}H_{12}N_2O_3FBr0.5H_2O$: C, 49.50; H, 3.38; N, 7.22. Found: C, 49.34; H, 3.26; N, 7.21.

EXAMPLE 28

5-(4-chloro-3-nitrophenyl)-5,10-dihydro-1H,3H-dipyrano[3,4-b:4,3-e]pyridine-4,6(7H,9H)-dione A mixture of tetrahydropyran-3,5-dione (Terasawa, J. Org. Chem. (1977), 42, 1163–1169) (0.27 g, 2.4 mmol), 4-chloro-3-nitrobenzaldehyde (0.54 g, 2.9 mmol) and the product from Example 11C (0.27 g, 2.4 mmol) in ethanol (3 mL) was heated to 80° C. for 60 hours and then allowed to stand at ambient temperature for 5 hours. The solid was collected by filtration, washed with ethanol, dissolved in 1:1 methanol/methylene chloride, filtered, heated on steam bath (replacing the methylene chloride with methanol and concentrating the mixture to approximately 5 mL) and allowed to stand at ambient temperature for 2 hours. The resulting solid was collected by filtration, washed with methanol and dried to provide the title compound (0.061 g).
mp>260;
MS (ESI(+)) m/z 377 (M+H)$^+$;
MS (ESI(−)) m/z 375 (M−H)$^−$;
$^1$H NMR (DMSO-d$_6$) δ 4.06 (s, 4H), 4.51 (AB q, 4H), 5.02 (s, 1H), 7.54 (dd, 1H), 7.68 (d, 1H), 7.79 (d, 1H), 10.18 (bs, 1H);
Anal. Calcd for $C_{17}H_{13}N_2O_6Cl$: C, 54.20; H, 3.48; N, 7.44. Found: C, 53.84; H, 3.81; N, 7.14.

EXAMPLE 29

5-(3-cyanophenyl)-5,10-dihydro-1H,3H-dipyrano[3,4-b:4,3-e]pyridine-4,6(7H,9H)-dione A mixture of tetrahydropyran-3,5-dione (Terasawa, J. Org. Chem. (1977), 42, 1163–1169) (0.27 g, 2.4 mmol), 3-cyanobenzaldehyde (0.54 g, 2.9 mmol) and the product from Example 11C (0.27 g, 2.4 mmol) in ethanol (3 mL) was heated to 80° C. for 60 hours, cooled and concentrated. The residue was purified by chromatography on silica gel (5% methanol in methylene chloride) to provide a product which was dissolved in 1:5 methanol/methylene chloride, filtered, concentrated on a steam bath to remove the methylene chloride and allowed to stand at ambient temperature for 16 hours. The resulting solid was collected by filtration, washed with methanol and dried to provide the title compound (0.062 g).
mp>260;
MS (ESI(+)) m/z 323 (M+H)$^+$;
MS (ESI(−)) m/z 321 (M−H)$^−$;
$^1$H NMR (DMSO-d$_6$) δ 4.05 (s, 4H), 4.51 (AB q, 4H), 4.99 (s, 1H), 7.48 (m, 1H), 7.54–7.64 (m, 2H), 10.12 (bs, 1H);
Anal. Calcd for $C_{18}H_{14}N_2O_4$: C, 67.08; H, 4.38; N, 8.69. Found: C, 66.76; H, 4.67; N, 8.56.

EXAMPLE 30

5-(4-fluoro-3-iodophenyl)-5,10-dihydro-1H,3H-dipyrano[3,4-b:4,3-e]pyridine-4,6(7H,9H)-dione

EXAMPLE 30A

3-Amino-4-fluorobenzyl alcohol

3-Amino-4-fluorobenzoic acid (15 g, 97 mmol) in tetrahydrofuran at 0° C. was treated with 1.0 M borane-tetrahydrofuran complex (50 mL), stirred overnight at room temperature, treated with an additional 130 mL of 1.0 M borane-tetrahydrofuran complex, stirred 10 hours, quenched by the addition of methanol, stirred 3 hours at room temperature, concentrated and partitioned between aqueous sodium bicarbonate/methylene chloride. The methylene chloride layer was separated, dried (sodium sulfate), filtered, and concentrated. The residue was purified by flash chromatography over silica gel (ethyl acetate/hexane 1:1) to provide 7.0 g of the title compound.
$^1$H NMR (CDCl$_3$) δ 4.58 (s, 2H), 6.67 (br m, 1H), 6.81 (d, 1H), 6.95 (t, 1H).

EXAMPLE 30B

4-Fluoro-3-iodobenzylalcohol

The product from example 30A (7.0 g, 50 mmol) in water (100 mL) at 0° C. was treated slowly with concentrated sulfuric acid (30 mL) at a rate to maintain the temperature below 10° C. and then treated dropwise with an aqueous solution of sodium nitrite (3.45 g, 50 mmol). This solution was then added to a solution of potassium iodide (8.13 g, 50 mmol) in water (15 mL), heated to 60° C. for 2 hours, cooled and extracted with methylene chloride. The methylene chloride layer was washed with 10% sodium hydroxide, washed with 1 M sodium thiosulfate, washed with 10% hydrochloric acid, washed with aqueous sodium bicarbonate, dried (sodium sulfate), filtered, and concentrated. The residue was purified by flash chromatography over silica gel (ethyl acetate/hexane 7:3) to provide 6.4 g of the title compound.
$^1$H NMR (CDCl$_3$) δ 1.69 (t, 1H), 4.66 (d, 2H), 7.05 (t, 1H), 7.60 (d, 1H), 7.78 (dd, 1H).

EXAMPLE 30C

4-Fluoro-3-iodobenzaldehyde

The product from Example 30B (6.4 g, 26 mmol) in chloroform (300 mL) was treated with manganese dioxide (4.5 g, 50 mmol), stirred overnight, treated with an additional portion of manganese dioxide (2.25 g), stirred overnight, filtered and concentrated. The residue was purified by flash chromatography over silica gel (ethyl acetate/hexane 1:4) to provide 1.9 g of the title compound.
$^1$H NMR (CDCl$_3$) δ 7.23 (t, 1H), 7.89 (m, 1H), 8.32 (dd, 1H), 9.91 (s, 1H).

EXAMPLE 30D

5-(4-fluoro-3-iodophenyl)-5,10-dihydro-1H,3H-dipyrano[3,4b:4,3-e]pyridine-4,6(7H,9H)-dione A mixture of the 30% pure product from example 11B (tetrahydropyran-3,5-dione) (Terasawa, J. Org. Chem. (1977), 42, 1163–1169) (0.365 g, 2.4 mmol), the product from Example 30C (0.20 g, 0.80 mmol) and the product from Example 11C (0.090 g, 080 mmol) in ethanol (2 mL) were processed as described in Example 29 to provide the title compound (0.087 g) as a white solid.
mp>260° C.;
$^1$H NMR (DMSO-d$_6$) δ 4.05 (s, 4H), 4.50 (AB q, 4H), 4.90 (s, 1H), 7.15 (t, 1H), 7.20 (m, 1H), 7.57 (dd, 1H), 10.10 (bs, 1H);
MS (ESI+) m/z 442 (M+H)$^+$;
MS (ESI−) m/z 440 (M−H)$^-$;
Anal. Calcd for C$_{17}$H$_{13}$NO$_4$FI: C, 46.28; H, 2.97; N, 3.17. Found: C, 45.38; H, 3.68; N, 2.91.

EXAMPLE 31

5-(5-bromo-2-hydroxyphenyl)-5,10-dihydro-1H,3H-dipyrano[3,4b:4,3-e]pyridine-4,6(7H,9H)-dione A mixture of 30% pure product from Example 11B (tetrahydropyran-3,5-dione) (Terasawa, J. Org. Chem. (1977), 42, 1163–1169) (0.81 g, 1.7 mmol), 5-bromosalicylaldehyde (0.43 g, 2.2 mmol) and the product from Example 11C (0.20 g, 1.7 mmol) in ethanol (4 mL) was heated to 80° C. for 60 hours and then allowed to stand at ambient temperature for 4 hours. The resulting solid was collected by filtration, washed with ethanol and dried to provide the title compound (0.12 g).
mp>260° C.;
MS (ESI(+)) m/z 392 (M+H)$^+$;
MS (ESI(−)) m/z 390 (M−H)$^-$;
$^1$H NMR (DMSO-d$_6$) δ 4.03 (s, 4H), 4.48 (AB q, 4H), 4.93 (s, 1H), 6.66 (d, 1H), 7.07–14 7.15 (m, 2H), 9.50 (s, 1H), 10.09 (bs, 1H);
Anal. Calcd for C$_{17}$H$_{14}$NO$_5$Br: C, 52.06; H, 3.60; N, 3.57. Found: C, 51.81; H, 3.45; N, 3.48.

EXAMPLE 32

5-[4-fluoro-3-(trifluoromethyl)phenyl]-5,10-dihydro-1H,3H-dipyrano[3,4-b:4,3-e]pyridine-4,6(7H,9H)-dione A mixture of 30% pure product from Example 11B (tetrahydropyran-3,5-dione) (Terasawa, J. Org. Chem. (1977), 42, 1163–1169) (0.81 g, 1.7 mmol), 4-fluoro-3-(trifluoromethyl) benzaldehyde (0.42 g, 2.2 mmol) and the product from Example 11C (0.20 g, 1.7 mmo) in ethanol (4 mL) was processed as described in Example 31 to provide the title compound (0.12 g) as a white solid.
mp>260° C.;
MS (ESI(+)) m/z 384 (M+H)$^+$, 401 (M+NH$_4$)$^+$;
MS (ESI(−)) m/z 382 (M−H)$^-$;
$^1$H NMR (DMSO-d$_6$) δ 4.06 (s, 4H), 4.51 (AB q, 4H), 5.01 (s, 1H), 7.40 (t, 1H), 7.52 (d, 2H), 10.11 (bs, 1H);
Anal. Calcd for C$_{18}$H$_{13}$NO$_4$F$_4$: C, 56.40; H, 3.42; N, 3.65. Found: C, 56.13; H, 3.62; N, 3.45.

EXAMPLE 33

5-(3,4-dichlorophenyl)-5,10-dihydro-1H,3H-dipyrano[3,4b:4,3-e]pyridine-4,6(7H,9H)-dione A mixture of 30% pure product from Example 11B (tetrahydropyran-3,5-dione) (Terasawa J. Org. Chem. (1977), 42, 1163–1169) (0.81 g, 1.7 mmol), 3,4-dichlorobenzaldehyde (0.39 g, 2.2 mmol) and the product from Example 11C (0.20 g, 1.7 mmol) in ethanol (4 mL) was processed as described in Example 31 to provide the title compound (0.15 g) as a white solid.
mp>260° C.;
MS (ESI(+)) m/z 366 (M+H)$^+$, 383 (M+NH$_4$)$^+$;
MS (ESI(−)) m/z 364 (M−H)$^-$;
$^1$H NMR (DMSO-d$_6$) δ 4.05 (s, 4H), 4.50 (AB q, 4H), 4.94 (s, 1H), 7.19 (dd, 1H), 7.36 (d, 1H), 7.53 (d, 1H), 10.12 (bs, 1H);
Anal. Calcd for C$_{17}$H$_{13}$NO$_4$Cl$_2$0.375C$_2$H$_6$O: C, 55.60; H, 4.01; N, 3.65. Found: C, 55.21; H, 3.64; N, 3.36.

EXAMPLE 34

5-(2,1,3-benzoxadiazol-5-yl)-5,10-dihydro-1H,3H-dipyrano[3,4-b:4,3-e]pyridine-4,6(7H,9H)-dione A mixture of tetrahydropyran-3,5-dione (Terasawa, J. Org. Chem. (1977), 42, 1163–1169) (0.27 g, 2.4 mmol), 2,1,3-benzoxadiazole-5-carboxaldehyde (Gasco, A. M. Eur. J. Med. Chem. Chim. Ther. (1996), 31,3–10) (0.54 g, 2.9 mmol) and the product from Example 11C (0.27 g, 2.4 mmol) in ethanol (3 mL) was processed as described in Example 29 to provide the title compound (0.088 ) as a solid.
mp>260° C.;
MS (ESI(−)) m/z 338 (M−H)$^-$;
$^1$H NMR (DMSO-d$_6$) δ 4.08 (s, 4H), 4.54 (AB q, 4H), 5.06 (s, 1H), 7.61 (m, 2H), 7.97 (d, 1H), 10.23 (bs, 1H);
Anal. Calcd for C$_{17}$H$_{13}$N$_3$O$_5$0.5C$_2$H$_6$O: C, 59.15; H, 4.26; N, 11.83. Found: C, 59.09; H, 4.32; N, 11.99.

EXAMPLE 35

5-(5-nitro-2-thienyl)-5,10-dihydro-1H,3H-dipyrano[3,4-b:4,3e-]pyridine-4,6(7H,9H)-dione A mixture of 30% pure Example 11B (tetrahydropyran-3,5-dione) (Terasawa, J. Org. Chem. (1977), 42, 1163–1169) (0.60 g, 1.3 mmol), 5-nitro-2-thiophene carboxaldehyde (0.25 g, 1.6 mmol) and the product from Example 11C (0.15 g, 1.3 mmol) in ethanol (3 mL) was processed as described in Example 29 to provide the title compound (0.087 g) as a solid.
MS (ESI(+)) m/z 366 (M+NH$_4$)$^+$;
MS (ESI(−)) m/z 347 (M−H)$^-$;
$^1$H NMR (DMOS-d$_6$) δ 4.10 (dd, 2H), 4.17 (d, 2H), 4.52 (AB q, 4H), 5.22 (s, 1H), 6.86 (dd, 1H), 7.93 (d, 1H), 10.35 (s, 1H);
Anal. Calcd for C$_{15}$H$_{12}$N$_2$O$_6$S0.25H$_2$O0.25C$_2$H$_6$O: C, 51.10; H, 3.87; N, 7.69. Found: C, 51.04; H, 3.92; N, 7.41.

EXAMPLE 36

5-(5-nitro-3-thienyl)-5,10-dihydro-1H,3H-dipyrano[3,4-b:4,3-e]pyridine-4,6(7H,9H)-dione A mixture of 30% pure product from Example 11B (tetrahydropyran-3,5-dione) (Terasawa, J. Org. Chem.

(1977), 41, 1163–1169) (0.60 g, 1.3 mmol), 2-nitrothiophene 4-carboxaldehyde (0.25 g, 1.6 mmol) and the product from Example 11C (0.15 g, 1.3 mmol) in ethanol (3 mL) was processed as described in Example 29 to provide the title compound (0.084 g) as a solid.
mp>260° C.;
MS (ESI(+)) m/z 366 (M+NH$_4$)$^+$;
MS (ESI(−)) m/z 347 (M−H)$^-$;
$^1$H NMR (DMSO-d$_6$) δ 4.09 (AB q, 4H), 4.50 (AB q, 4H), 5.01 (s, 1H), 7.58 (d, 1H), 7.76 (d, 1H), 10.15 (bs, 1H);
Anal. Calcd for C$_{15}$H$_{12}$N$_2$O$_6$S0.25H$_2$O: C, 51.06; H, 3.57; N, 7.94. Found: C, 51.33; H, 3.78; N, 7.57.

EXAMPLE 37

9-(4-fluoro-3-iodophenyl)-2,3,5,9-tetrahydro-4H-pyrano[3,4-b]thieno[2,3-e]pyridin-8(7H)-one 1,1-dioxide

EXAMPLE 37A tert-butyl 9-(3-bromo-4-fluorophenyl)-8-oxo-2,3,5,7,8,9-hexahydro-4H-pyrano[3,4-b]thieno[2,3-e]pyridine-4-carboxylate 1,1-dioxide A mixture of the product from Example 12C (0.040 g, 0.096 mmol), di-tert-butyl dicarbonate (0.12 g, 0.55 mmol) and 4-dimethylaminopyridine (0.0020 g, 0.016 mmol) in acetonitrile (3 mL) was stirred for 2 hours at ambient temperature and concentrated. The residue was purified by chromatography on silica gel (2:1 and then 1:1 hexanes/ethyl acetate) to provide the title compound (0.035 g) which crystallized on standing.
MS (ESI(+)) m/z 531 (M+NH$_4$)$^+$.

EXAMPLE 37B tert-butyl 9-[4-fluoro-3-(trimethylstannyl)phenyl]-8-oxo-2,3,5,7,8,9-hexahydro-4H-pyrano [3,4-b]thieno [2,3-e]pyridine-4-carboxylate 1,1-dioxide A mixture of the product from Example 37A (0.035 g, 0.068 mmol) in anhydrous 1,4-dioxane (1 mL) under an atmosphere of nitrogen was treated with hexamethylditin (0.14 mL, 0.5 mmol), treated with tetrakis (triphenylphosphine) palladium(0) (0.050 g, 0.043 mmol), stirred at 100° C. for 1 hour, cooled to ambient temperature and concentrated. The residue was purified by chromatography on silica gel (3:2 hexanes:ethyl acetate) to provide the title compound (0.031 g) which crystallized on standing.
MS (ESI(+)) m/z 598 (M+H)$^+$.

EXAMPLE 37C 9-(4-fluoro-3-iodophenyl)-2,3,5,9-tetrahydro-4H-pyrano[3,4-b]thieno[2,3-e]pyridin-8(7H)-one 1,1-dioxode A mixture of the product from Example 37B (0.023 g, 0.038 mmol) in 1% acetic acid in methanol (25 mL) was treated with N-chlorosuccinimide (0.010 g, 0.077 mmol), then treated with sodium iodide (0.011 g, 0.077 mmol), stirred for 10 minutes, treated with pulverized sodium thiosulfate pentahydrate (0.020 g, 0.080 mmol), stirred for 10 minutes and concentrated to dryness. The residue was treated with trifluoroacetic acid (3 mL), stirred at ambient temperature for 15 minutes and concentrated to dryness. The residue was treated with trifluoroacetic acid (3 mL), heated gently on a steam bath for 1 minute, cooled to ambient temperature and concentrated to dryness. The residue was purified by chromatography on silica gel (2% methanol and then 5% methanol in methylene chloride) to provide the title compound (0.0156 g).
mp>260° C.;
MS (ESI(−)) m/z 460 (M−H)$^-$;
$^1$H NMR (DMSO-d$_6$) δ 2.77–2.90 (m, 1H), 3.01–3.14 (m, 1H), 3.32–3.43 (m, 2H), 4.02 (s, 2H), 4.49 (AB q, 2H), 4.87 (s, 1H), 7.16 (t, 1H), 7.24 (m, 1H), 7.59 (dd, 1H), 10.13 (bs, 1H);
Anal. Calcd for C$_{16}$H$_{13}$NO$_4$SFI: C, 41.66; H, 2.84; N, 3.04. Found: C, 41.28; H, 2.79; N, 2.87.

EXAMPLE 38

5-(3-chloro-4-fluorophenyl)-2,3,5,7,8,9-hexahydro-1H-cyclopenta[b][1,7]naphthyridine-4,6-dione hydrochloride

EXAMPLE 38A 2-benzyl-5-(3-chloro-4-fluorophenyl)-2,3,5,7,8,9-hexahydro-1H-cyclopenta [b][1,7]naphthyridine-4,6-dione A mixture of 3-amino-2-cyclopenten-1-one (Kikani, B. B., Synthesis, (1991), 2, 176) (0.78 g, 8 mmol), 3-chloro-4-fluorobenzaldehyde (1.12 g, 8 mmol), and N-benzylpiperidine-3,5-dione (Ziegler, J. Amer. Chem. Soc. (1973), 95, 7458–7464) (1.78 g, 8 mmol) in ethanol (8 mL) was processed in Example 5A to provide 1.8 of the title compound.
MS (ESI(−)) m/z 421 (M−H)$^-$;
$^1$H NMR (DMSO-d$_6$) δ 2.3 (m, 2H), 2.5–2.72 (m, 2H), 3.07 (Abqu, 2H), 3.5 (m, 2H), 3.67 (s, 2H), 4.65 (s, 1H), 7.15 (s, 1H), 7.42 (m, 7H), 10.28 (s, 1H).

EXAMPLE 38B (1R,2S,5R)-5-methyl-2-(1-methyl-1-phenylethyl) cyclohexyl 5-(3-chloro-4-fluorophenyl)-4,6-dioxo-1,3,4,5,6,7,8,9-octahydro-2H-cyclopenta[b][1,7] naphthyridine-2-carboxylate The product from Example 38A (1.8 g, 4.3 mmol) was processed as in Example 5B to provide 0.2 g of the title compound as the less polar isomer.
MS (ESI(−)) m/z 589 (M−H)$^-$.

EXAMPLE 38C 5-(3-chloro-4-fluorophenyl)-2,3,5,7,8,9-hexahydro-1H-cyclopenta[b][1,7]naphthyridine-4,6-dione hydrochloride The product from Example 38B (0.2 g, 0.33 mmol) was treated with 48% hydrogen bromide in acetic acid (4 mL), stirred for 72 hours, neutralized with concentrated ammonium hydroxide, and extracted with methylene chloride (3×). The combined organic layers were dried (Na$_2$SO$_4$), filtered, and concentrated. Purification of the residue on silica gel (10% ethanol/ammonia saturated methylene chloride) to provide the title compound (0.03 g) which was converted to the HCl salt.
MS (ESI(−)) m/z 331 (M−H)$^-$;
$^1$H NMR (DMSO-d$_6$) δ 2.28 (t, 2H), 2.52–2.7 (m, 2H), 3.18 (s, 2H), 3.6 (m, 2H), 4.68 (s, 1H), 7.2 (m, 1H), 7.23 (t, 1H), 7.32 (dd, 1H), 10.18 (s, 1H);
Anal. Calcd for C$_{17}$H$_{14}$N$_2$FClO$_2$HCl2H$_2$O: C, 50.49; H, 4.51; N, 6.73. Found: C, 49.52; H, 4.26; N, 6.09.

EXAMPLE 39

9-(3-bromo-4-fluorophenyl)-5,6,7,9-tetrahydrofuro
[3,4-b][1,7]naphthyridine-1,8(3H,4H)-dione
hydrochloride

EXAMPLE 39A methyl 7-benzyl-4-(3-bromo-4-fluorophenyl)-2-
methyl-5-oxo-1,4,5,6,7,8-hexahydro [1,7]
naphthyridine-3-carboxylate A solution of methyl 3-aminocrotonate (0.58 g, 5 mmol), 3-bromo-4-fluorobenzaldehyde (1.0 g, 5 mmol) and N-benzylpiperidine-3,5-dione (Ziegler, J. Amer. Chem. Soc. (1973), 95, 7458–7464) (1.1 g, 5 mmol) in ethanol (5 mL) was heated at reflux in a sealed tube for 24 hours and concentrated. Purification of the residue on silica gel eluting with 5% ethanol/methylene chloride provided the title compound (1.3 g) as a yellow foam.
MS (ESI(-)) m/z 485 (M–H)$^-$.

EXAMPLE 39B 6-benzyl-9-(3-bromo-4-fluorophenyl)-5,6,7,9-
tetrahydrofuro[3,4-b][1,7]naphthyridine-1,8(3H,4H)-
dione A solution of the product from Example 39A (3.1 g, 6.3 mmol) in chloroform (50 mL) was cooled to 0° C., treated with 90% pyridinium tribromide (2.45 g, 6.9 mmol), warmed to ambient temperature, stirred for 16 hours and washed with water. The chloroform layer was isolated, dried (MgSO$_4$), filtered, refluxed for 16 hours and cooled in an ice bath. The resulting precipitate was collected by filtration and dried to provide the title compound (2.1 g) as tan crystals.
MS (ESI(-)) m/z 467 (M–H)$^-$;
$^1$H NMR (DMSO-d$_6$) δ 3.08 (AB q, 2H), 3.5 (d, 2H), 3.65 (d, 2H), 4.7 (s, 1H), 4.9 (AB q, 2H), 7.3 (m, 7H), 7.47 (m, 1H). 10.1 (1H).

EXAMPLE 39C 9-(3-bromo-4-fluorophenyl)-5,6,7,9-tetrahydrofuro
[3,4-b][1,7]naphthyridine-1,8(3H,4H)-dione
hydrochloride A solution of product from Example 39B (0.35 g, 0.75 mmol) in methylene chloride (10 ml) was treated with vinyl chloroformate (0.1 mL, 1.2 mmol), stirred at ambient temperature for 16 hours, concentrated to dryness, treated with ethanol (10 mL), treated with 6N HCl (3 mL), refluxed for 5 hours and concentrated to dryness. Purification of the residue on silica gel (10:90:1 ethanol/methylene chloride/ saturated ammonium hydroxide) provided the title compound (0.08 g) which was converted the HCl salt.
mp255–257° C.;
MS (ESI(-)) m/z 377 (M–H)$^-$;
$^1$H NMR (DMSO-d$_6$) δ 3.2 (s, 2H), 3.62 (s, 2H), 4.7 (s, 1H), 4.83 (d, 1H), 4.99 (d, 1H), 7.27 (m, 2H), 7.49 (dd, 1H), 10.25 (s, 1H);
Anal. Calcd for $C_{16}H_{11}N_2FBrO_3HCl0.5C_2H_5OH$: C, 46.65; H, 3.45; N, 6.40. Found: C, 46.99; H, 3.69; N, 6.42.

EXAMPLE 40

9-(3-bromo-4-fluorophenyl)-5,6,7,9-tetrahydrofuro
[3,4-b][1,7]naphthyridine-1,8(3H, 4H)-dione
hydrochloride

EXAMPLE 40A (1R,2S,5R)-5-methyl-2-(1-methyl-1-phenylethyl)
cyclohexyl 9-(3-bromo-4-fluorophenyl)-1,8-dioxo-1,
4,5,7,8,9-hexahydrofuro[3,4-b][1,7]naphthyridine-6
(3H)-carboxylate A solution of the product from Example 39C (1.46 g, 2.13 mmol) in tetrahydrofuran (70 ml) was treated with 8-phenylmenthol chloroform prepared from (-)-8-phenylmenthol as described in (Yamamoto, Y., J. Amer. Chem. Soc. (1992), 114, 121–125) (1.1 g, 3.74 mmol), refluxed for 36 hours, filtered to remove the unreacted starting material and concentrated. Purification of the residue on silica gel (9:9:2 methylene chloride/ethyl acetate/ hexane) provided the title compound (0.46 g) as the less polar diastereomer.
MS (ESI(-)) m/z 635 (M–H)$^-$.

EXAMPLE 40B 9-(3-bromo-4-fluorophenyl)-5,6,7,9-tetrahydrofuro
[3,4-b][1,7]naphthyridine-1,8)3H,4H)-dione
hydrochloride A solution of the product from Example 40A (0.4 g, 0.63 mmol) in acetic acid (2 mL) was treated with 48% hydrobromic acid (0.5 mL), heated to 60° C. for 5 hours, cooled to ambient temperature, neutralized with saturated ammonium hydroxide and extracted with chloroform (10 mL). The organic layer was dried (MgSO$_4$), filtered concentrated. The residue was purified on silica gel (20:80:1 ethanol/ methylene chloride/saturated ammonium hydroxide) to provide the unreacted starting material (0.21 g) and the title compound (0.05 g) which was converted to the HCl salt.
MS (ESI(-)) m/z 379 (M–H)$^-$;
$^1$H NMR (DMSO-d$_6$) (free base) δ 3.25 (s, 2H), 3.68 (s, 2H), 4.7 (s, 1H), 4.85 (d, 1H), 4.98 (d, 1H), 7.28 (m, 2H), 7.5 (dd, 1H), 10.23 (s, 1H);
Anal. Calcd for $C_{16}H_{11}N_2BrFO_3HCl:H_2O$: C, 44.42; H, 3.26; N, 6.47. Found: C, 44.74; H, 3.93; N, 6.51.

EXAMPLE 41

5-(3-bromo-4-fluorophenyl)-7,7-dimethyl-5,8,9,10-
tetrahydro-1H-pyrano[3,4-b]quinoline-4,6(3H,7H)-
dione A mixture of the product from Example 11C (0.16 g, 1.4 mmol), 3-bromo-4-fluorobenzaldehyde (0.29 g, 1.4 mmol), 4,4-dimethyl-1,3-cyclohexanedione (2.0 g, 1.4 mmol) and ethanol (18 mL) was heated at 80° C. for 60 hours, cooled, concentrated to an oil and triturated with 3:1 ethanol/diethyl ether (3×). The resulting solid was dried to provide the total compound (0.11 g) as a yellow solid.
mp>260° C.;
MS (DCI/NH$_3$) m/z 420 (M+H)$^+$;
$^1$H NMR (DMSO-d$_6$) δ 9.76 (br s, 1H), 7.38 (dd, 1H, J=6.8, 2.0 Hz), 7.24-7.13 (m, 2H), 4.88 (s, 1H), 4.46 (AB q, 2H, JAB=11.2, dvAB=15.9 Hz), 4.01 (s, 2H), 2.68-2.48 (m, 2H), 1.78 (t, 2H), 0.98 (s, 3H), 0.93 (s, 3H);
$^{13}$C NMR (DMSO-d$_6$) δ 199.7, 191.2 155.9, 149.9, 144.5, 131.9, 128.5, 116.2, 110.1, 108.6, 107.2, 107.0, 71.2, 63.2, 39.6, 34.0, 31.4, 24.7, 24.0, 23.1;
Anal. Calcd for $C_{20}H_{19}BrFNO_3$; C, 57.16; H, 4.56; N, 3.33. Found: C, 57.10; H, 4.70; N, 3.19.

EXAMPLE 42

(9R)-9-(3-bromo-4-fluorophenyl)-5,9-dihydro-3H-
furo[3,4-b]pyrano[4,3-e]pyridine-1,8(4H,7H)-dione The enantiomers of Example 25C were separated by chiral chromatography on a Chiralpak AS column (5.0 cm inner diameter, 50 cm length, 20 micron packing) using 80:20 hexane:ethanol at a flow rate of 117 mL/minute as the mobile phase. A total of 227 mg in 100 mL hot ethanol (three injections of 20 mL, 40 mL and 40 mL) was used to provide the faster moving isomer which was repurified by chromatography on silica gel using a gradient of 1%–2% and 5% methanol in methylene chloride to provide the title compound (0.080 g).

MS (ESI(+)) m/z 380 (M+H)$^+$, 397 (M+NH$_4$)$^+$;

MS (ESI(−)) m/z 378 (M−H)$^-$;

$^1$H NMR (DMSO-d$_6$) δ 4.06 (s, 2H), 4.54 (AB q, 2H), 4.75 (s, 1H), 4.88 (d, 1H), 5.03 (d, 1H), 7.28 (d, 2H), 7.48 (d, 1H), 10.50 (s, 1H);

Anal. Calcd for C$_{16}$H$_{11}$NO$_4$FBr0.1875 CH$_2$Cl$_2$; C, 49.09; H, 2.89; N, 3.54. Found: C, 49.11; H, 2.93; N, 3.17.

EXAMPLE 43

(9S)-9-(3-bromo-4-fluorophenyl)-5,9-dihydro-3H-furo[3,4-b]pyrano[4,3-e]pyridine-1,8(4H, 7H)-dione The title compound (0.080 g) was provided as the slower moving enantiomer from the procedure described in Example 42.

MS (ESI(+)) m/z 380 (M+H)$^+$, 397 (M+NH$_4$);

MS (ESI(−)) m/z 378 (M−H)$^-$;

$^1$NMR (DMSO-d$_6$) δ 4.06 (s, 2H), 4.54 (AB q, 2H), 4.75 (s, 1H), 4.88 (d, 1H), 5.03 (d, 1H), 7.28 (d, 1H), 10.50 (s, 1H);

Anal. Calcd for C$_{16}$H$_{11}$NO$_4$FBr0.125 CH$_2$Cl$_2$; C, 49.46; H, 2.90; N, 3.58. Found: C, 49.54; H, 3.07; N, 3.27.

EXAMPLE 44

10-(3-chloro-4-fluorophenyl)-3,4,6,10-tetradydro-2H-pyrano[3,4-b][1,6]naphthyridine-1,9(5H,8H)-dione A mixture of the product from Example 11C (0.023 g, 0.2 mmol), piperidine-2,4-dione (Nakagawa, S., Heterocycles (1979), 13, 447–495) (0.23 g, 0.2 mmol), 3-chloro-4-fluorobenzaldehyde (0.032 g, 0.2 mmol) and ethanol (2 mL) was heated to 80° C. for 60 hours and cooled to ambient temperature. The resulting solid was collected by filtration, washed with ethanol and dried under vacuum to provide the title compound.

MS (APCI(+)) m/z 349 (M+H)$^+$;

MS (APCI(−)) m/z 347 (M−H)$^-$;

$^1$H NMR (DMSO-d$_6$) δ 2.34-2.57 (m,2H), 3.13-3.28 (m, 2H), 4.00 (s, 2H), 4.45 (AB q, 2H), 4.96 (s, 1H), 7.17 (ddd, 1H), 7.26 (t, 1H), 7.28 (dd, 1H), 9.55 (s, 1H).

EXAMPLE 45

10-(3,4-dichlorophenyl)-3,4,6,10-tetrahydro-2H-pyrano[3,4-b][1,6]naphthyridine-1,9(5H,8H)-dione Example 11C was processed as in Example 44 but substituting 3,4-dichlorobenzaldehyde for 3-chloro-4-fluorobenzaldehyde to provide the title compound.

MS (APCI(+)) m/z 365 (M+H)$^+$;

MS (APCI(−)) m/z 363 (M−H)$^-$;

$^1$H NMR (DMSO-d$_6$) δ 2.36-2.58 (m, 2H), 3.14-3.26 (m, 2H), 4.00 (AB q, 2H), 4.45 (AB q, 2H), 4.96 (s, 1H), 7.09 (s, 1H), 7.17 (dd, 1H), 7.34 (d, 1H), 7.49 (d, 1H), 9.57 (s, 1H).

EXAMPLE 46

10-[4-chloro-3-(trifluoromethyl)phenyl]-3,4,6,10-tetrahydro-2H-pyrano[3,4-b][1,6]naphthyridine-1,9(5H,8H)-dione Example 11C was processed as in Example 44 but substituting 4-chloro-3-(trifluoromethyl)benzaldehyde for 3-chloro-4-fluorobenzaldehyde to provide the title compound.

MS (APCI(+)) m/z 399 (M+H)$^+$;

MS (APCI(−)) m/z 397 (M−H)$^-$;

$^1$H NMR (DMSO-d$_6$) δ 2.36-2.58 (m, 2H), 3.15-3.26 (m, 2H), 4.00 (AB q, 2H), 4.45 (AB q, 2H), 5.02 (s, 1H), 7.11 (s, 1H), 7.46 (dd, 1H), 7.63 (d, 1H), 9.60 (s, 1H).

EXAMPLE 47

10-(4-chloro-3-nitrophenyl)-3,4,6,10-tetrahydro-2H-pyrano[3,4-b][1,6]naphthyridine-1,9(5H,8H)-dione Example 11C was processed as in Example 44 but substituting 4-chloro-3-nitrobenzaldehyde for 3-chloro-4-fluorobenzaldehyde to provide the title compound.

MS (APCI(−)) m/z 374 (M−H)$^-$;

$^1$H NMR (DMSO-d$_6$) δ 2.42-2.57 (m, 2H), 3.16-3.30 (m, 2H), 4.01 (AB q, 2H), 4.46 (AB q, 2H), 5.03 (s, 1H), 7.12 (d, 1H), 7.52 (dd, 1H), 7.64 (d, 1H), 7.76 (d, 1H), 9.62 (s, 1H).

EXAMPLE 48

10-(3,4-dibromophenyl)-3,4,6,10-tetrahydro-2H-pyrano[3,4-b][1,6]naphthyridine-1,9(5H,8H)-dione Example 11C was processed as in Example 44 but substituting 3,4-dibromobenzaldehyde for 3-chloro-4 fluorobenzaldehyde to provide the title compound.

MS (APCI(+)) m/z 453 (M+H)$^+$;

MS (APCI(−)) m/z 451 (M−H)$^-$;

$^1$H NMR (DMSO-d$_6$) δ 2.41-2.57 (m, 2H), 3.18-3.26 (m, 2H), 4.00 (AB q, 2H), 4.45 (AB q, 2H), 4.93 (s, 1H), 7.09 (bs, 1H), 7.49 (d, 1H), 7.61 (d, 1H), 9.56 (s, 1H).

EXAMPLE 49

10-(5-nitro-3-thienyl)-3,4,6,10-tetrahydro-2H-pyrano[3,4-b][1,6]naphthyridine-1,9(5H,8H)-dione Example 11C was processed as in Example 44 but substituting 5-nitrothiophene-3-carboxaldehyde for 3-chloro-4-fluorobenzaldehyde to provide the title compound.

MS (APCI(+)) m/z 348 (M+H)$^+$;

MS (APCI(−)) m/z 346 (M−H)$^-$;

$^1$H NMR (DMSO-d$_6$) δ 2.39-2.54 (m, 2H), 3.19-3.30 (m, 2H), 4.02 (s, 2H), 4.42 (AB q, 2H), 5.00 (s, 1H), 7.09 (d, 1H), 7.48 (d, 1H), 7.75 (d, 1H), 9.69 (bs, 1H).

EXAMPLE 50

5-(3-bromo-4-fluorophenyl)-5,8,9,10-tetrahydro-1H-thiopyrano[3,4-b]quinoline-4,6(3H,7H)-dione A mixture of thiopyran-3,5-dione (Fehnel, E. A., J. Amer. Chem. Soc., (1955), 77, 4241–4244) (0.12 g, 1.0 mmol), 3-bromo-4-fluorobenzaldehyde (0.20 g, 1.0 mmol), 3-amino-2-cyclohexene-1-one (0.11 g, 1.0 mmol) and ethanol (5 mL) was heated to 80° C. in a sealed tube for 60 hours and cooled to ambient temperature. The resulting solid was collected by filtration, washed with ethanol and fried for 16 hours under high vacuum to provide the title compound (0.13 g).

MS (APCI(+)) m/z 408 (M+H)$^+$;

MS (APCI(−)) m/z 406 (M−H)$^-$;

$^1$H NMR (DMSO-d$_6$) δ 1.77-1.88 (m, 1H), 1.89-1.98 (m 1H), 2.25 (dd, 2H), 2.46-2.62 (m, 2H), 3.10 (dd, 1H), 3.48 (ddd, 2H), 3.82 (d, 1H), 4.96 (s, 1H), 7.15-7.24 (m, 2H), 7.41 (dd, 1H), 9.71 (s, 1H);

Anal. Calcd for $C_{18}H_{15}BrFNO_2S$: C,52.95; H, 3.70; N, 3.43. Found: C, 52.81; H, 3.79; N, 3.17.

EXAMPLE 51

5-(3-bromo-4-fluorophenyl)-5,7,8,9-tetrahydrocyclopenta[b]thiopyrano[4,3-e]pyridine-4,6(1H,3H)-dione Thiopyran-3,5-dione (Fehnel, E. A., J. Amer. Chem. Soc., (1955), 77, 4241–4244) (0.12 g, 1.0 mmol) was processed as described in Example 50 but substituting 3-amino-2-cyclopentene-1-one for 3-amino-2-cyclohexene-1-one to provide a solid. The solid was purified by chromatography on silica gel eluting with 1:1 acetone:methylene chloride to provide the title compound (0.13 g).
MS (APCI(+)) m/z 394 (M+H)$^+$;
MS (APCI(−)) m/z 392 (M−H)$^−$;
$^1$H NMR (DMSO-d$_6$) δ 2.28 (t, 2H), 2.48-2.73 (m 2H), 3.14 (dd, 2H), 3.47 (dd, 1H), 3.54 (dd, 1H), 3.82 (dd, 1H), 4.72 (s, 1H), 7.18-7.25 (m, 2H), 7.42 (dd, 1H), 10.27 (s, 1H);
Anal. Calcd for $C_{17}H_{13}NO_2SFBr$: C,51.79; H, 3.32; N, 3.55. Found: C, 51.46; H, 3.49; N, 3.39.

EXAMPLE 52

10(3-bromo-4-fluorophenyl)-3,4,6,10-tetrahydro-2H-pyrano[3,4-b][1,6]naphthyridine-1,9(5H,8H)-dione Example 11C was processed as in Example 44 but substituting 3-bromo-4-fluorobenzaldehyde for 3-chloro-4-fluorobenzaldehyde to provide the title compound (0.79 g).
MS (APCI(+)) m/z 393 (M+)$^+$;
MS (APCI(−)) m/z 391 (M−H)$^−$;
$^1$H NMR (DMSO-d$_6$) δ 2.38-2.60 (m, 2H), 3.18-3.26 (m, 2H), 4.00 (s, 2H), 4.45 (AB q, 2H), 4.95 (s, 1H), 7.14 (s, 1H), 7.16-7.28 (m, 2H), 7.41 (dd, 1H), 9.59 (s, 1H);
Anal. Calcd for $C_{17}H_{14}N_2O_3FBr$: C, 51.93; H, 3.59; N, 7.12. Found: C, 51.68; H, 3.83; N, 7.10.

Determination of Potassium Channel Opening Activity Membrane Hyperpolarization Assays Compounds were evaluated for potassium channel opening activity using primary cultured guinea-pig urinary bladder (GPB) cells.

For the preparation of urinary bladder smooth muscle cells, urinary bladders were removed from male guinea-pigs (Harley, Charles River, Wilmington, Mass.) weighing 300–400 grams (g) and placed in ice-cold $Ca^{2+}$-free Krebs solution (Composition, millimolar (mM):KCl, 2.7; $KH_2PO_4$, 1.5; NaCl, 75; $Na_2HPO_4$; 9.6; $Na_2HPO_4$; $7H_2O$, 8; $MgSO_4$, 2; glucose, 5; HEPES, 10; pH 7.4). Cells were isolated by enzymatic dissociation (Klockner, U. and Isenberg, G., Pflugers Arch. (1985), 405, 329–339). The bladder was cut into small sections and incubated in 5 milliliters (mL) of the Kreb's solution containing 1 milligram per milliliter (mg/mL) of collagenase (Sigman, St. Louis, Mo.) and 0.2 mg/mL of pronase (Calbiochem, La Jolla, Calif.) with continuous stirring in a cell incubator for 30 minutes. The mixture was then centrifuged at 1300×g for 5 minutes, and the pellet resuspended in Dulbecco's phosphate buffered saline (PBS) (GIBCO, Gaithersburg, Md.) and recentrifuged to remove residual enzyme. The cell pellet was resuspended in 5 mL growth media (composition: Dulbecco's modified Eagle's medium supplemented with 10% fetal bovine serum, 100 units/mL penicillin, 100 units/mL streptomycin and 0.25 mg/mL amphotericin B) and further dissociated by pipetting the suspension through a flame-polished Pasteur pipette and passing it through a polypropylene mesh membrane (Spectrum, Houston, Tex.). The cell density was adjusted to 100,000 cells/mL by resuspension in growth media. Cells were plated in clear-bottomed black 96- well plates (Packard) for membrane potential studies at a density of 20,000 cells/well and maintained in a cell incubator with 90% air:10% $CO_2$ until confluent. Cells were confirmed to be of smooth muscle type by cytoskeletal staining using a monoclonal mouse anti human-α-smooth muscle actin (Biomeda, Foster City, Calif.).

Functional activity at potassium channels was measured by evaluating changes in membrane potential using the bis-oxonal dye DiBAC(4)$_3$ (Molecular Probes) in a 96-well cell-based kinetic assay system using a Fluorescent Imaging Plate Reader (FLIPR) (K. S. Schroeder et al., J. Biomed. Screen., v. 1 pp. 75–81 (1996)). DiBAC(4)$_3$ is an anionic potentiometric probe which partitions between cells and extracellular solution in a membrane potential-dependent manner. With increasing membrane potential (for example, $K^+$ depolarization), the probe further partitions into the cell; this is measured as an increase in fluorescence due to dye interaction with intracellular lipids and proteins. Conversely, decreasing membrane potential (hyperpolarization by potassium channel openers) evokes a decrease in fluorescence.

Confluent guinea-pig urinary bladder cells cultured in black clear-bottomed 96-well plates were rinsed twice with 200 mL assay buffer (composition, mM: HEPES, 20; NaCl, 120; KCl, 2; $CaCl_2$, 2; $MgC_2$; 1; glucose, 5; pH 7.4 at 25° C.) containing 5 μM DiBAC(4)$_3$ and incubated with 180 mL of the buffer in a cell incubator for 30 minutes at 37° C. to ensure dye distribution across the membrane. After recording the baseline fluorescence for 5 minutes, the reference or test compounds, prepared at 10 times the concentration in the assay buffer, were added directly to the wells. Changes in fluorescence were monitored for an additional 25 minutes. Hyperpolarization responses were corrected for any background noise and were normalized to the response observed with 10 μM of the reference compound P1075 (assigned as 100%), a potent opener of smooth muscle $K_{ATP}$ channels (Quast et al., Mol. Pharmacol., v. 43 pp. 474–481 (1993)).

Routinely, five concentrations of P1075 or test compounds (log or half-log dilutions) were evaluated and the maximal steady-state hyperpolarization values (expressed as % relative to P1075) plotted as a function of concentration. The $Ec_{50}$ (concentration that elicits 50% of the maximal response for the test sample) values were calculated by non-linear regression analysis using a four parameter sigmoidal equation. The maximal micromolar $EC_{50}$ response of each compound (expressed as % relative to P1075) is reported. Stock solutions of compounds were prepared in 100% DMSO and further dilutions were carried out in the assay buffer and added to a 96-well plate.

TABLE 1

Membrane Hyperpolarization (MHP) in Guinea-Pig Bladder (GPB) Cells

| Example Number | Maximal Response (% P1075) | EC50 (μM) |
|---|---|---|
| 1 | 96 | 0.027 |
| 2 | 88 | 0.65 |

TABLE 1-continued

Membrane Hyperpolarization (MHP) in Guinea-Pig Bladder (GPB) Cells

| Example Number | Maximal Response (% P1075) | EC50 ($\mu$M) |
|---|---|---|
| 3 | 41 | 27 |
| 4 | 21 | |
| 5 | 97 | 0.19 |
| 6 | 83 | 1.0 |
| 7 | 75 | 0.57 |
| 8 | 33 | 5.0 |
| 9 | 89 | 2.6 |
| 10 | 87 | 1.4 |
| 11 | 104 | 0.023 |
| 12 | 101 | 0.014 |
| 13 | 101 | 0.24 |
| 14 | 99 | 0.40 |
| 15 | 90 | 0.64 |
| 16 | 57 | 8.8 |
| 17 | 93 | 0.0042 |
| 18 | 95 | 0.058 |
| 19 | 94 | 1.8 |
| 20 | 93 | 0.035 |
| 21 | 79 | 0.066 |
| 22 | 85 | 0.046 |
| 23 | 82 | 0.040 |
| 24 | 74 | 0.73 |
| 25 | 106 | 0.0098 |
| 26 | 90 | 0.013 |
| 27 | 87 | 0.97 |
| 28 | 98 | 0.064 |
| 29 | 87 | 1.1 |
| 30 | 84 | 0.0074 |
| 31 | 83 | 1.3 |
| 32 | 102 | 0.015 |
| 33 | 92 | 0.0034 |
| 34 | 88 | 0.091 |
| 35 | 98 | 0.025 |
| 36 | 98 | 0.082 |
| 37 | 105 | 0.00064 |
| 38 | 82 | 0.39 |
| 39 | 80 | 0.68 |
| 40 | 111 | 0.32 |
| 41 | 66 | 0.071 |
| 42 | 102 | 0.026 |
| 43 | 98 | 0.011 |
| 44 | 96 | |
| 45 | 85 | 0.20 |
| 46 | 83 | 0.34 |
| 47 | 91 | 0.49 |
| 48 | 91 | 0.084 |
| 49 | 85 | 2.3 |
| 50 | 108 | 0.084 |
| 51 | 88 | 0.12 |
| 52 | 105 | 0.38 |

In vitro Functional models

Compounds were evaluated for functional potassium channel opening activity using tissue strips obtained from Landrace pig bladders.

Landrace pig bladders were obtained from female Landrace pigs of 9–30 kg. Landrace pigs were euthanized with an intraperitoneal injection of pentobarbital solution, Somlethal®, J. A. Webster Inc. Sterling Mass. The entire bladder was removed and immediately placed into Krebs Ringer bicarbonate solution (composition, mM: NaCl, 120; $NaHCO_3$, 20; dextrose, 11; KCl, 4.7; $CaCl_2$, 2.5; $MgSO_4$, 1.5; $KH_2PO_4$, 1.2; $K_2EDTA$, 0.01, equilibrated with 5% $CO_2$/95% $O_2$ pH 7.4 at 37° C.). Propranolol (0.004 mM) was included in all of the assays to block β-adrenoceptors. The trigonal and dome portions were discarded. Strips 3–5 millimeters (mm) wide and 20 mm long were prepared from the remaining tissue cut in a circular fashion. The mucosal layer was removed. One end was fixed to a stationary glass rod and the other to a Grass FT03 transducer at a basal preload of 1.0 g. Two parallel platinum electrodes were included in the stationary glass rod to provide field stimulation of 0.05 Hz, 0.5 milli-seconds at 20 volts. This low frequency stimulation produced a stable twitch response of 100–500 centigrams. Tissues were allowed to equilibrate for at least 60 minutes and primed with 80 mM KCl. A control concentration response curve (cumulative) was generated for each tissue using the potassium channel opener P1075 as the control agonist. P1075 completely eliminated the stimulated twitch in a dose dependent fashion over a concentration range of $10^{-9}$ to $10^{-5}$M using ½ log increments. After a 60 minute rinsing period, a concentration response curve (cumulative) was generated for the test agonist in the same fashion as that used for the control agonist P1075. The maximal efficacy of each compounds (expressed as % relative to P1075) is reported. The amount of agent necessary to cause 50% of the agent's maximal response ($ED_{50}$) was calculated using "ALLFIT" (DeLean et al., Am. J. Physiol., 235, E97 (1980)), and agonist potencies were expressed as $p_{D2}$ (the negative logarithm). Agonist potencies were also expressed as an index relative to P1075. The index was calculated by dividing the $ED_{50}$ for P1075 by the $ED_{50}$ for the test agonist in a given tissue. Each tissue was used for only one test agonist, and the indices obtained from each tissue were averaged to provide an average index of potency. These data are shown in Table 2.

TABLE 2

Functional Potassium Channel Opening Activity in Isolated Bladder Strips

| | Landrace Pig Bladder | | |
|---|---|---|---|
| Example Number | Efficacy (% P1075) | $pD_2$ | Index |
| 1 | 97 | 6.9 | 0.36 |
| 2 | 99 | 5.8 | 0.041 |
| 5 | 100 | 6.4 | 0.16 |
| 6 | 100 | 5.4 | 0.022 |
| 7 | 97 | 5.4 | 0.040 |
| 8 | 90 | 5.2 | 0.023 |
| 9 | 82 | 3.9 | 0.0015 |
| 10 | 96 | 4.3 | 0.0028 |
| 11 | 91 | 6.8 | 1.2 |
| 12 | 85 | 7.2 | 3.3 |
| 13 | 98 | 5.9 | 0.13 |
| 15 | 100 | 5.7 | 0.027 |
| 18 | 100 | 7.3 | 1.6 |
| 19 | 100 | 6.0 | 0.70 |
| 20 | 93 | 5.6 | 0.43 |
| 22 | 100 | 5.6 | 0.027 |
| 24 | 100 | 6.0 | 0.055 |
| 28 | 94 | 6.7 | 0.42 |
| 29 | 89 | 5.8 | 0.075 |
| 30 | 100 | 7.6 | 1.1 |
| 31 | 85 | 5.1 | 0.065 |
| 32 | 100 | 6.3 | 0.41 |
| 33 | 93 | 5.9 | 0.27 |
| 34 | 93 | 7.0 | 0.96 |
| 35 | 100 | 7.4 | 1.8 |
| 36 | 100 | 6.5 | 0.24 |
| 37 | 95 | 7.3 | 2.1 |
| 38 | 80 | 5.3 | 0.024 |
| 39 | 96 | 5.6 | 0.036 |
| 40 | 91 | 6.0 | 0.13 |
| 42 | 95 | 6.2 | 0.17 |

TABLE 2-continued

Functional Potassium Channel Opening Activity
in Isolated Bladder Strips

Landrace Pig Bladder

| Example Number | Efficacy (% P1075) | $pD_2$ | Index |
|---|---|---|---|
| 43 | 88 | 6.7 | 0.68 |
| 47 | 96 | 6.2 | 0.28 |
| 52 | 99 | 5.3 | 0.069 |

As shown by the data in Tables 1 and 2, the compounds of this invention reduce stimulated contractions of the bladder by opening potassium channels and therefore may have utility in the treatment of symptoms and/or diseases prevented by or ameliorated with potassium channel openers.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such a propylene glycol; esters such as ethyl oleate and ethyl laurate; agar; buffering agents such as magnesium hydroxide and aluminum hydroxide; alginic acid; pyrogen-free water; isotonic saline; Ringers's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator.

The present invention provides pharmaceutical compositions which comprise compounds of the present invention formulated together with one or more non-toxic pharmaceutically acceptable carriers. The pharmaceutical compositions can be formulated for oral administration in solid or liquid form, for parenteral injection or for rectal administration.

Further included within the scope of the present invention are pharmaceutical compositions comprising one or more of the compounds of formula I–VIII prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersion. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan ester, microcrystalline cellulose, aluminum metahydroxide, bentonite, agar—agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar—agar, calcium carbonate, potato or tapioca starch, alginic acid, certain silicates, and sodium carbonate; e) solution retarding agents such as paraffin); f) absorption accelerators such as quaternary ammonium compounds; g) wetting agents such as cetyl alcohol and glycerol monostearate;) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelating capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polymide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds of the present invention may also be administered in the form of liposomes. As is known in the art, liposomes are generally derived from phospholidpids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholidpids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

The term "pharmaceutically acceptable cation, " as used herein, refers to a positively-charged inorganic or organic ion that is generally considered suitable for human consumption. Examples of pharmaceutically acceptable cations are hydrogen, alkali metal (lithium, sodium and potassium), magnesium, calcium, ferrous, ferric, ammonium, alkylammonium, kialkylammonium, trialkylammonium, tetraalkylammonium, diethanolammonium, and choline. Cations may be interchanged by methods known in the art, such as ion exchange.

The terms "pharmaceutically acceptable salts, esters and amides," as used herein, refer to carboxylate salts, amino acid addition salts, zwitterions, esters and amides of compounds of formula I–VIII which are, within the scope of sound medical judgement, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt," as used herein, refers to salts that are well known in the art. For example, S. M. Berge et al. describe pharmaceutically acceptable salts in detail in (J. Pharmaceutical Sciences, 66:1–19 (1997)). Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include nitrate, bisulfate, borate, formate, butyrate, valerate, 3-phenylpropionate, camphorate, adipate, benzoate, oleate, palmitate, stearate, laurate, lactate, fumarate, ascorbate, aspartate, nicotinate, p-toluenesulfonate, camphorsulfonate, methanesulfonate, 2-hydroxyethanesulfonate, gluconate, glucoheptonate, lactobionate, glycerophaosphate, pectinate, lauryl sulfate, and the like, metal salts such as sodium, potassium, magnesium or calcium salts or amino salts such as ammonium, triethylamine salts, and the like, all of which may be prepared according to conventional methods.

The term "pharmaceutically acceptable ester," as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula I–VIII may be prepared according to conventional methods.

The term "pharmaceutically acceptable amide," as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula I–VIII may be prepared according to conventional methods. It is intended that amides of the present invention include amino acid and peptide derivatives of the compounds of formula I–VIII, as well.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to the parent compound of the above formula I–VIII, for example, by hydrolysis in blood. A thorough discussion is provided in (T. Higuchi and V. Stella, Pro-drugs as Novel Delivery Systems. V. 14 of the A.C.S. Symposium Series, and in Edward B. Roche, ed., Bioreversible Carriers in Drug Design, American Pharmaceutical Association and Pergamon Press (1987)).

The term "prodrug ester group," as used herein refers, to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art. Other examples of prodrug ester groups can be found in the book ("Pro-drugs as Novel Delivery Systems," by Higuchi and Stella) cited above.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

The present invention contemplates pharmaceutically active metabolites formed by in vivo biotransformation of compounds of formula I–VIII. The term pharmaceutically active metabolite, as used herein, refers to a compound formed by the in vivo biotransformation of compounds of formula I–VIII. The present invention contemplates compounds of formula I–VIII and metabolites thereof. A thorough discussion of biotransformation is provided in Goodman and Gilman's, The Pharmacological Basis of Therapeutics, seventh edition, hereby incorporated by reference.

The compounds of the invention, including but not limited to those specified in the examples possess potassium channel opening activity in mammals (especially humans). As potassium channel openers, the compounds of the present invention are useful for the treatment and prevention of diseases such as asthma, epilepsy, hypertension, Raynaud's syndrome, impotence, migraine, pain, eating disorders, urinary incontinence, functional bowel disorders, neurodegeneration and stroke.

The ability of the compounds of the invention to treat asthma, epilepsy, hypertension, Raynaud's syndrome, male sexual dysfunction, female sexual dysfunction, migraine, pain, eating disorders, urinary incontinence, functional bowel disorders, neurodegeneration and stroke can be demonstrated according to the methods described (D. E. Nurse et a., Br. J. Urol., v 68 pp 27–31 (1991); B. B. Howe et al., J. Pharmacol. Exp. Ther., v. 274 pp. 884–890 (1995); K.

Lawson, Pharmacol. Ther., v. 70 pp. 39–63 (1996); D. R. Gehlert, et al., Neuro-Psychopharmacol & Biol. Psychiat., v. 18 pp. 1093–1102 (1994); M. Gopalakrishnan et al., Drug Development Research, v. 28 pp. 95–127 (1993); J. E. Freedman et al., The Neuroscientist, v. 2 pp. 145–152 (1966); D. Spanswick et al., Nature, v. 390 pp. 521–25 (Dec. 4, 1997)).

Aqueous liquid compositions of the present invention are particularly useful for the treatment and prevention of asthma, epilepsy, hypertension, Raynaud's syndrome, male sexual dysfunction, female sexual dysfunction, migraine, pain, eating disorders, urinary incontinence, functional, bowel disorders, neurodegeneration and stroke.

When used in the above or other treatments, a therapeutically effective amount of one of the compounds of the present invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 10 mg/kg/day. For purposes of oral administration, ore preferable doses can be in the range of from about 0.01 to about 5 mg/kg/day. If desired, the effective daily dose can be divided into multiple doses for purposes of administration, consequently, single dose compositions may contain such amounts or submultiples thereof to make up the daily dose.

We claim:

1. A compound having formula I

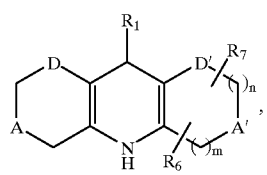

I or a pharmaceutically acceptable salt, amide, ester, or prodrug thereof, wherein n is 0–1;

m is 1–2;

A is selected from the group consisting of $NR_2$, O, and S;

A' is selected from the group consisting of $NR_3$, O, S and $CR_4R_5$;

D is selected from the group consisting of $CH_2$ and $C(O)$;

D' is selected from the group consisting of $CH_2$, $C(O)$, $S(O)$, and $S(O)_2$;

$R_1$ is selected from the group consisting of aryl and heterocycle;

$R_2$ and $R_3$ are independently selected from the group consisting of hydrogen, alkoxyalkyl, alkyl, arylalkyl, cycloalkyl, cycloalkylalkyl, haloalkyl, heterocyclealkyl, hydroxy, hydroxyalkyl, $-NZ_1Z_2$, and $(NZ_1Z_2)$alkyl wherein $A_1$ and $Z_2$ are independently selected from the group consisting of hydrogen, alkyl, alkylcarbonyl, aryl, arylalkyl, and formyl;

$R_4$ and $R_5$ are independently selected from the group consisting of hydrogen and alkyl;

$R_6$ and $R_7$ are independently selected from the group consisting of hydrogen and alkyl;

with the proviso that when D is $CH_2$ then D' is other than $CH_2$; and with the proviso that when D' is $S(O)$ or $S(O)_2$ then A' is $CR_4R_5$.

2. A compound according to claim 1 of formula II:

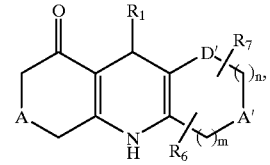

II or a pharmaceutically acceptable salt, amide, ester, or prodrug thereof wherein, n is 0–1;

m is 1–2;

A is selected from the group consisting of $NR_2$, O, and S;

A' is selected from the group consisting of $NR_3$, O, S and $CR_4R_5$;

D' is selected from the group consisting of $CH_2$, $C(O)$, $S(O)$, and $S(O)_2$;

$R_1$ is selected from the group consisting of aryl and heterocycle;

$R_2$ and $R_3$ are independently selected from the group consisting of hydrogen, alkoxyalkyl, alkyl, arylalkyl, cycloalkyl, cycloalkylalkyl, haloalkyl, heterocyclealkyl, hydroxy, hydroxyalkyl, $-NZ_1Z_2$, and $(NZ_1Z_2)$alkyl wherein $Z_1$ and $Z_2$ are independently selected from the group consisting of hydrogen, alkyl, alkylcarbonyl, aryl, arylalkyl, and formyl;

$R_4$ and $R_5$ are independently selected from the group consisting of hydrogen and alkyl; and $R_6$ and $R_7$ are independently selected from the group consisting of hydrogen and alkyl.

3. A compound according to claim 2 wherein A is $NR_2$.

4. A compound according to claim 2 wherein A is O.

5. A compound according to claim 2 wherein A is S.

6. A compound according to claim 1 of formula III:

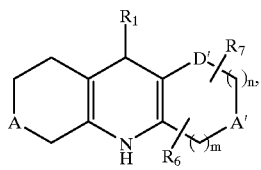

or a pharmaceutically acceptable salt, amide, ester, or prodrug thereof wherein, n is 0–1;

m is 1–2;

A is selected from the group consisting of $NR_2$, O, and S;

A' is selected from the group consisting of $NR_3$, O, S and $CR_4R_5$;

D' is selected from the group consisting of $CH_2$, C(O), S(O), and $S(O)_2$;

$R_1$ is selected from the group consisting of aryl and heterocycle;

$R_2$ and $R_3$ are independently selected from the group consisting of hydrogen, alkoxyalkyl, alkyl, arylalkyl, cycloalkyl, cycloalkylalkyl, haloalkyl, heterocyclealkyl, hydroxy, hydroxyalkyl, —$NZ_1Z_2$, and ($NZ_1Z_2$)alkyl wherein $Z_1$ and $Z_2$ are independently selected from the group consisting of hydrogen, alkyl, alkylcarbonyl, aryl, arylalkyl, and formyl;

$R_4$ and $R_5$ are independently selected from the group consisting of hydrogen and alkyl; and $R_6$ and $R_7$ are independently selected from the group consisting of hdyrogen and alkyl.

7. A compound according to claim 6 wherein A is $NR_2$.

8. A compound according to claim 6 wherein A is O.

9. A compound according to claim 6 wherein A is S.

10. A compound according to claim 1 of formula IV:

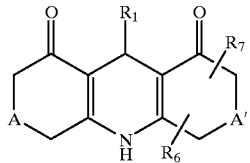

or a pharmaceutically acceptable salt, amide, ester, or prodrug thereof wherein, A is selected from the group consisting of $NR_2$, O, and S;

A' is selected from the group consisting of $NR_3$, O, S and $CR_4R_5$;

$R_1$ is selected from the group consisting of aryl and heterocycle;

$R_2$ and $R_3$ are independently selected from the group consisting of hydrogen, alkoxyalkyl, alkyl, arylalkyl, cycloalkyl, cycloalkylalkyl, haloalkyl, heterocyclealkyl, hydroxy, hydroxyalkyl, —$NZ_1Z_2$, and ($NZ_1Z_2$)alkyl wherein $Z_1$ and $Z_2$ are independently selected from the group consisting of hydrogen, alkyl, alkylcarbonyl, aryl, arylalkyl, and formyl;

$R_4$ and $R_5$ are independently selected from the group consisting of hydrogen and alkyl; and $R_6$ and $R_7$ are independently selected from the group consisting of hydrogen and alkyl.

11. A compound according to claim 10 wherein

A is $NR_2$; and

A' is $NR_3$.

12. A compound according to claim 10 wherein

A is $NR_2$;

A' is $NR_3$;

$R_6$ is hydrogen; and $R_7$ is hyydrogen.

13. A compound according to claim 12 that is 5-(3-bromo-4-fluorophenyl)- 2,3,5,8,9,10-hexahydropyrido[3,4-b][1,7]naphthyridine-4,6(1H,7H)-dione.

14. A compound according to claim 10 wherein

A is $NR_2$; and

A' is O.

15. A compound according to claim 10 wherein

A is $NR_2$; and

A' is S.

16. A compound according to claim 10 wherein

A is O; and

A' is $NR_3$.

17. A compound according to claim 10 wherein

A is O;

A' is $NR_3$;

$R_6$ is hydrogen; and $R_7$ is hydrogen.

18. A compound according to claim 17 that is 5-(3-bromo-4-fluorophenyl)-5,8,9,10-tetrahydro-1H-pyrano[3,4-b][1,7]naphthyridine-4,6(3H,7H)-dione.

19. A compound according to claim 10 wherein

A is O; and

A' is O.

20. A compound according to claim 10 wherein

A is O;

A' O $R_6$ is hydrogen; and $R_7$ is hydrogen.

21. A compound according to claim 20 selected from the group consisting of 5-(3-bromo-4-fluorophenyl)-5,10-dihydro-1H,3;H-dipyrano[3,4-b:4,3-e]pyridine-4,6(7H,9H)-dione, 5-(4-chloro-3-nitrophenyl)-5,10-dihydro-1H,3H-dipyrano[3,4-b:4,3-e]pyridine-4,6(7H,9H)-dione, 5-(3-cyanophenyl)-5,10-dihydro-1H,3H-dipyrano[3,4-b:4,3-e]pyridine-4,6(7H,9H)-dione, 5-(4-fluoro-3-iodophenyl)-5,10-dihydro-1H,3H-dipyrano[3,4-b:4,3-e]pyridine-4,6(7H,9H)-dione, 5-(5-bromo-2-hydroxyphenyl)-5,10-dihydro-1H,3H-dipyrano[3,4-b:4,3-e]pyridine-4,6(7H,9H)-dione, 5-[4-fluoro-3-(trifluoromethyl)phenyl]-5,10-dihydro-1H,3H-dipyrano[3,4-b:4,3-e]pyridine-4,6)7H,9H)-dione, 5-(3,4-dichlorophenyl)-5,10-dihydro-1H,3H-dipyrano[3,4-b:4,3-e]pyridine-4,6(7H,9H)-dione, 5-(2,1,3-benzoxadiazol-5-yl)-5,10-dihydro-1H,3H-dipyrano[3,4-b:4,3-e]pyridine-4,6(7H,9H)-dione, 5-(5-nitro-2-thienyl)-5,10-dihydro-1H,3H-dipyrano[3,4-b:4,3-e]pyridine-4,6(7H,9H)-dione, and 5-(5-nitro-3-thienyl)-5,10-dihydro-1H,3H-dipyrano[3,4-b:4,3-e]pyridine-4,6(7H,9H)-dione.

22. A compound according to claim 10 wherein

A is O; and

A' is S.

23. A compound according to claim 10 wherein
A is O;
A' is S
$R_6$ is hydrogen; and
$R_7$ is hydrogen.
24. A compound according to claim 23 that is 5-(3-bromo-4-fluorophenyl)-5,10-dihydro-1H,3H-pyrano[3,4-b]thiopyrano[4,3-e]pyridine-4,6)7H,9H)-dione.
25. A compound according to claim 10 wherein
A is S; and
A' is $NR_3$.
26. A compound according to claim 10 wherein
A is S; and
A' is O.
27. A compound according to claim 10 wherein
A is S; and
A' is S.
28. A compound according to claim 1 of formula V:

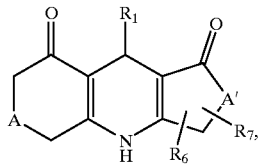

V or a pharmaceutically acceptable salt, amide, ester, or prodrug thereof wherein,
A is selected from the group consisting of $NR_2$, O, and S;
A' is selected from the group consisting of $NR_3$, O, S and $CR_4R_5$;
$R_1$ is selected from the group consisting of aryl and heterocycle;
$R_2$ and $R_3$ are independently selected from the group consisting of hydrogen, alkoxyalkyl, alkyl, arylalkyl, cycloalkyl, cycloalkylalkyl, haloalkyl, heterocyclealkyl, hydroxy, hydroxyalkyl, $-NZ_1Z_2$, and $(NZ_1Z_2)$alkyl wherein $Z_1$ and $Z_2$ are independently selected from the group consisting of hydrogen, alkyl, alkylcarbonyl, aryl, arylalkyl, and formyl;
$R_4$ and $R_5$ are independently selected from the group consisting of hydrogen and alkyl; and
$R_6$ and $R_7$ are independently selected from the group consisting of hydrogen and alkyl.
29. A compound according to claim 28 wherein
A is $NR_2$; and
A' is $NR_3$.
30. A compund according to claim 28 wherein
A is $NR_2$; and
A' is O.
31. A compound according to claim 28 wherein
A is $NR_2$;
A' is O;
$R_6$ is hydrogen; and
$R_7$ is hydrogen.
32. A compund according to claim 31 that is selected from the group consisting of 9-(3-bromo-4-fluorophenyl)-5,6,7,9-tetrahydrofuro[3,4-b][1,7]naphthyridine-1,8)3H,4H)-dione,
(+) 9-(3-bromo-4-fluorophenyl)-5,6,7,9-tetrahydrofuro[3,4-b][1,7]naphthyridine-1,8(3H,4H)-dione; and
(−) 9-(3-bromo-4-fluorophenyl)-5,6,7,9-tetrahydrofuro[3,4-b][1,7]naphthyridine-1,8(3H,4H)-dione.
33. A compound according to claim 28 wherein
A is $NR_2$; and
A' is S.
34. A compound according to claim 28 wherein
A is $NR_2$; and
A' is $CR_4R_5$.
35. A compound according to claim 28 wherein
A is $NR_2$;
A' is $CR_4R_5$;
$R_4$ is hydrogen;
$R_5$ is hydrogen;
$R_6$ is hydrogen; and
$R_7$ is hydrogen.
36. A compound according to claim 35 that is selected from
(−)-5-(3-bromo-4-fluoroophenyl)-2,3,5,7,8,9-hexahydro-1H-cyclopenta[b][1,7]naphthyridine-4,6-dione,
(+)-5-(3-bromo-4-fluorophenyl)-2,3,5,7,8,9-hexahydro-1H-cyclopenta[b][1,7]naphthyridine-4,6-dione,
(+) 5-(3-chloro-4-fluorophenyl)-2,3,5,7,8,9-hexahydro-1H-cyclopenta[b][1,7]naphthyridine-4,6-dione, and
(−) 5-(3-chloro-4-fluorophenyl)-2,3,5,7,8,9-hexahydro-1H-cyclopenta[b][1,7]naphthyridine-4,6-dione.
37. A compound according to claim 28 wherein
A is O; and
A' is $NR_3$.
38. A compound according to claim 28 wherein
A is O;
A' is $NR_3$;
$R_6$ is hydrogen; and
$R_7$ is hydrogen.
39. A compound according to claim 38 that is selected from the group consisting of
9-(3-bromo-4-fluorophenyl)-2-methyl-2,3,5,9-tetrahydropyrano[3,4-b]pyrrolo[3,4-e]pyridine-1,8(4H,7H)-dione; and
9-(3-bromo-4-fluorophenyl)-2,3,5,9-tetrahydropyrano[3,4-b]pyrrolo[3,4-e]pyridine-1,8(4H,7H)-dione.
40. A compound according to claim 28 wherein
A is O; and
A' is O.
41. A compound according to claim 28 wherein
A is O;
A' is O;
$R_6$ is hydrogen; and
$R_7$ is hydrogen.
42. A compound according to claim 41 that is selected from the group consisting of
9-(3-bromo-4-fluorophenyl)-5,9-dihydro-3H-furo[3,4-b]pyrano[4,3-e]pyridine-1,8(4H,7H)-dione,
(9R)-9-(3-bromo-4-fluorophenyl)-5,9-dihydro-3H-furo[3,4-b]pyrano[4,3-e]pyridine-1,8(4H,7H)-dione; and
(9S)-9-(3-bromo-4-fluorophenyl)-5,9-dihydro-3H-furo[3,4-b]pyrano[4,3-e]pyridine-1,8(4H,7H)-dione.
43. A compound according to claim 28 wherein
A is O; and
A' is S.
44. A compound according to claim 28 wherein
A is O; and A' is CR$_4$R$_5$.

45. A compound according to claim 28 wherein

A is O;

A' is CR$_4$R$_5$;

R$_4$ is hydrogen;

R$_5$ is hydrogen;

R$_6$ is hydrogen; and

R$_7$ is hydrogen.

46. A compound according to claim 45 that is selected from the group consisting of 5-(3-bromo-4-fluorophenyl)-5,7,8,9-tetrahydrocyclopenta[b]pyrano[4,3-e]pyridine-4,6 (1H,3H)-dione and 5-(4-chloro-3-nitrophenyl)-5,7,8,9-tetrahydrocyclopenta [b]pyrano[4,3-e]pyridine-4,6-(1H,3H)-dione.

47. A compound according to claim 28 wherein

A is S; and

A' is NR$_3$.

48. A compound according to claim 28 wherein

A is S; and

A' is O.

49. A compound according to claim 28 wherein

A is S; and

A' is S.

50. A compound according to claim 28 wherein

A is S; and

A' is CR$_4$R$_5$.

51. A compound according to claim 28 wherein

A is S;

A' is CR$_4$R$_5$;

R$_4$ is hydrogen;

R$_5$ is hydrogen;

R$_6$ is hydrogen; and

R$_7$ is hydrogen.

52. A compound according to claim 51 that is 5-(3-bromo-4-fluorophenyl)-5,7,8,9-tetrahydrocyclopenta[b]thiopyrano [4,3-e]pyridine-4,6(1H,3H)-dione.

53. A compound according to claim 1 of formula VI:

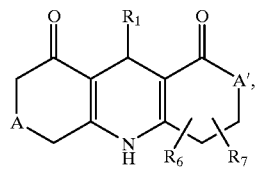

VI or a pharmaceutically acceptable salt, amide, ester, or pro-drug thereof wherein, A is selected from the group consisting of NR$_2$, O, and S;

A' is selected from the group consisting of NR$_3$, O, S and CR$_4$R$_5$;

R$_1$ is selected from the group consisting of aryl and heterocycle;

R$_2$ and R$_3$ are independently selected from the group consisting of hydrogen, alkoxyalkyl, alkyl, arylalkyl, cycloalkyl, cycloalkylallyl, haloalkyl, heterocyclealkyl, hydroxy, hydroxyalkly, —NZ$_1$Z$_2$, and (NZ$_1$Z$_2$)alkyl wherein Z$_1$ and Z$_2$ are independently selected from the group consisting of hydrogen, alkyl, alkylcarbonyl, aryl, arylalkyl, and formyl;

R$_4$ and R$_5$ are independently selected from the group consisting of hydrogen and alkyl; and R$_6$ and R$_7$ are independently selected from the group consisting of hydrogen and alkyl.

54. A compound according to claim 53 wherein

A is NR$_2$; and

A' is NR$_3$.

55. A compound according to claim 53 wherein

A is NR$_2$; and

A' is O.

56. A compound according to claim 53 wherein

A is NR$_2$; and

A' is S.

57. A compound according to claim 53 wherein

A is NR$_2$; and

A' is CR$_4$R$_5$.

58. A compound according to claim 53 wherein

A is NR$_2$;

A' is CR$_4$R$_5$;

R$_4$ is hydrogen;

R$_5$ is hydrogen;

R$_6$ is hydrogen; and

R$_7$ is hydrogen.

59. A compound according to claim 58 that is selected from the group consisting of 5-(3-bromo-4-fluorophenyl)-2,3,5,8,9,10-hexahydrobenzo[b][1,7]naphthyridine-4,6(1H, 7H)-dione, 5-(3-bromo-4-fluorophenyl)-2-methyl-2,3,5,8,9,10-hexahydrobenzo[b][1,7]naphthyridine-4,6(1H,7H)-dione, (−)-5-(3-bromo-4-fluorophenyl)-2,23,5,8,9,10 hexahydrobenzo[b][1,7]naphthyridine-4,6(1H,7H)-dione; and (+)-5-(3-bromo-4-fluorophenyl)-2,3,5,8,9,10-hexahydrobenzo[b][1,7]naphthyridine-4,6(1H,7H)-dione.

60. A compound according to claim 53 wherein

A is O; and

A' is NR$_3$.

61. A compound according to claim 53 wherein

A is O;

A' is NR$_3$;

R$_6$ is hydrogen; and

R$_7$ is hydrogen.

62. A compound according to claim 61 that is selected from the group consisting of 10-(3-chloro-4-fluorophenyl)-3,4,6,10-tetrahydro-2H-pyrano[3,4-b][1,6]naphthyridine-1, 9(5H,8H)-dione, 10-(3,4-dichlorophenyl)-3,4,6,10-tetrahydro-2H-pyrano [3,4-b][1,6]naphthyridine- 1,9(5H,8H)-dione, 10-[4-chloro-3-(trifluoromethyl)phenyl]-3,4,6,10-tetrahydro-2H-pyrano[3,4-b][1,6]naphthyridine-1,9 (5H,8H)-dione, 10-(4-chloro-3-nitorphenyl)-3,4,6,10-tetrahydro-2H-pyrano[3,4-b][1,6]naphthyridine-1,9(5H,8H)-dione, 10-(3,4-dibromophenyl)-3,4,6,10-tetrahydro-2H-pyrano [3,4-b][1,6]naphthyridine-1,9(5H,8H)-dione, 10-(5-nitro-3-thienyl)-3,4,6,10-tetrahydro-2H-pyrano[3, 4-b][1,6]napthhyridine-1,9(5H,8H)-dione; and 10-(3-bromo-4-fluorophenyl)-3,4,6,10-tetrahydro-2H-pyrano[3,4-b][1,6]naphthyridine-1,9)5H,8H)-dione.

63. A compound according to claim 53 wherein

A is O; and

87

A' is O.

64. A compound according to claim 53 wherein

A is O; and

A' is S.

65. A compound according to claim 53 wherein

A is O; and

A' is $CR_4R_5$.

66. A comound according to claim 53 wherein

A is O;

A' is $CR_4R_5$;

$R_6$ is hydrogen; and $R_7$ is hydrogen.

67. A compound according to claim 53 wherein

A is O;

A' is $CR_4R_5$;

$R_4$ is hydrogen;

$R_5$ is hydrogen, $R_6$ is hydrogen; and $R_7$ is hydrogen.

68. A compound according to claim 67 that is 5-(3-bromo-4-fluorophenyl)-5,8,9,10-tetrahydro-1H-pyrano[3,4-b]quinoline-4,6(3H,7H)-dione.

69. A compound according to claim 53 wherein

A is O;

A' is $CR_4R_5$;

$R_4$ is methyl;

$R_5$ is methyl;

$R_6$ is hdyrogen; and $R_7$ is hydrogen.

70. A compound according to claim 69 that is 5-(3-bromo-4-fluorophenyl)-7,7-dimethyl-5,8,9,10-tetrahydro-1H-pyrano[3,4b]quinoline-4,6(3H,7H)-dione.

71. A compound according to claim 53 wherein

A is S; and

A' is $NR_3$.

72. A compound according to claim 53 wherein

A is S; and

A' is O.

73. A compound according to claim 53 wherein

A is S; and

A' is S.

74. A compound according to claim 53 wherein

A is S; and

A' is $CR_4R_5$.

75. A compound according to claim 53 wherein

A is S;

A' is $CR_4R_5$;

$R_4$ is hydrogen;

$R_5$ is hydrogen, $R_6$ is hydrogen; and $R_7$ is hydrogen.

76. A compound according to claim 75 that is 5-(3-bromo-4-fluorophenyl)-5,8,9,10-tetrahydro-1H-thiopyrano[3,4-b]quinoline-4,6(3H,7H)-dione.

88

77. A compound according to claim 1 of formula VII:

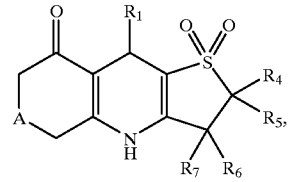

VII or a pharmaceutically acceptable salt, amide, ester, or prodrug thereof wherien, A is selected from the group consisting of $NR_2$, O, and S;

$R_1$ is selected from the group consisting of aryl and heterocycle;

$R_2$ is selected from the group consisting of hydrogen, alkoxyalkyl, alkyl, arylalkyl, cycloalkyl, cycloalkylalkyl, haloalkyl, heterocyclealkyl, hydroxy, hydroxyalkyl, —$NZ_1Z_2$, and ($NZ_1Z_2$)alkyl wherein $Z_1$ and $Z_2$ are independently selected from the group consisting of hydrogen, alkyl, alkylcarbonyl, aryl, arylalkyl, and formyl;

$R_4$ and $R_5$ independently selected from the group consisting of hydrogen and alkyl; and $R_6$ and $R_7$ are independently selected from the group consisting of hydrogen and alkyl.

78. A compound according to claim 77 wherein A is $NR_2$.

79. A compound according to claim 77 wherein

A is $NR_2$;

$R_4$ is hydrogen;

$R_5$ is hydrogen;

$R_6$ is hydrogen; and $R_7$ is hydrogen.

80. A compound according to claim 79 that is 9-(3-bromo-4-fluorophenyl)-2,3,5,6,7,9-hexahyydrothieno[3,2-b][1,7]naphthyridin-8(4H)-one 1,1-dioxide.

81. A compound according to claim 77 wherein A is O.

82. A compound according to claim 77 wherein

A is O;

$R_4$ is hydrogen;

$R_5$ is hydrogen;

$R_6$ is hydrogen; and $R_7$ is hydrogen.

83. A compound according to claim 82 that is selected from the group consisting of 9-(3-bromo-4-fluorophenyl)-2,3,5,9-tetrahydro-4H-pyrano[3,4-b]thieno[2,3-e]pyridin-8(7H)-one 1,1-dioxide, (+)-9-(3-bromo-4-fluorophenyl)-2,3,5,9-tetrahydro-4H-pyrano[3,4-b]thieno[2,3-e]pyridin-8(7H)-one 1,1-dioxide, (−)-9-(3-bromo-4-fluorophenyl)-2,3,5,9-tetrahydro-4H-pyrano[3,4-b]thieno[2,3-e]pyridin-8(7H)-one 1,1-dioxide, 9-(3-cyanophenyl)-2,3,5,9-tetrahydro-4H-pyrano[3,4-b]thieno[2,3-e]pyridin-8(7H)-one 1,1-dioxide, (+) 9-(3-cyanophenyl)-2,3,5,9-tetrahydro-4H-pyrano[3,4-b]thieno[2,3-e]pyridin-8(7H)-one 1,1-dioxide, (−) 9-(3-cyanophenyl)-2,3,5,9-tetrahydro-4H-pyrano[3,4-b]thieno[2,3-e]pyridin-8(7H)-one 1,1-dioxide, 9-(4-chloro-3-nitrophenyl)-2,3,5,9-tetrahydro-4H-pyrano[3,4-b]thieno[2,3-e]pyridin-8(7H)-one 1,1-dioxide, (+)-9(4-chloro-3-nitrophenyl)-2,3,5,9-tetrahydro-4H-pyrano[3,4-b]thieno[2,3-e]pyridin-8(7H)-one 1,1-dioxide, (−)-9-(4-chloro-3-nitrophenyl)-2,3,5,9-tetrahydro-4H-pyrano[3,4-b]thieno[2,3-e]pyridin-8(7H)-one 1,1-dioxide, (+) 9-(4-fluoro-3-iodophenyl)-2,3,5,9-tetrahydro-4H-pyrano[3,4-b]thieno[2,3-e]pyridin-8(7H)-one 1,1-dioxide; and (−) 9-(4-fluoro-3-iodophenyl)-2,3,5,9-tetrahydro-4H-pyrano[3,4b]thieno[2,3-e]pyridin-8(7H)-one 1,1-dioxide.

84. A compound according to claim 77 wherein A is S.

85. A compound according to claim 1 of formula VIII:

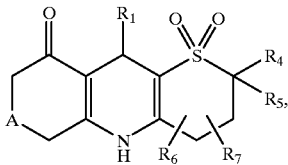

VIII or a pharmaceutically acceptable salt, amide, ester, or prodrug thereof wherein, A is selected from the group consisting of $NR_2$, O, and S;

$R_1$ is selected from the group consisting of aryl and heterocycle;

$R_2$ is selected from the group consisting of hydrogen, alkoxyalkyl, alkyl, arylalkyl, cycloalkyl, cycloalkylalkyl, haloalkyl, heterocyclealkyl, hydroxy, hydroxyalkyl, —$NZ_1Z_2$, and $(NZ_1Z_2)$alkyl wherein $Z_1$ and $Z_2$ are independently selected from the group consisting of hydrogen, alkyl, alkylcarbonyl, aryl, arylalkyl, and formyl;

$R_4$ and $R_5$ are independently selected from the group consisting of hydrogen and alkyl; and $R_6$ and $R_7$ are independently selected from the group consisting of hydrogen and alkyl.

86. A compound according to claim 85 wherein A is $NR_2$.

87. A compound according to claim 85 wherein

A is $NR_2$;

$R_4$ is hydrogen;

$R_5$ is hydrogen;

$R_6$ is hydrogen; and $R_7$ is hydrogen.

88. A compound according to claim 87 that is 10-(3-bromo-4-flurorphenyl)-3,4,6,7,8,10-hexahydro-2H-thiopyrano[3,2-b][1,7]naphthyridin-9(5H)-one 1,1-dioxide.

89. A compound according to claim 85 wherein A is O.

90. A compound according to claim 85 wherein

A is O;

$R_4$ is hydrogen;

$R_5$ is hydrogen;

$R_6$ is hydrogen; and $R_7$ is hydrogen.

91. A compound according to claim 90 that is 10-(3-bromo-4-fluorophenyl)-3,4,6,10-tetrahydro-2H,5H-pyrano[3,4-b]thiopyrano[2,3-e]pyridin-9(8H)-one 1,1-dioxide.

92. A compound according to claim 85 wherein A is S.

93. A pharmaceutical composition comprising a therapeutically effective amount of a comound of claim 1 in combination with a pharmaceutically acceptable carrier.

94. A method of treating asthma, epilepsy, hypertension, Raynaud's syndrome, migraine, pain, eating disorders, functional bowel disorders, neurodegeneration and stroke in a host mammal in need of such treatment comprising administering a therapeutically effective amount of a compound of claim 1.

95. The method of claim 94 for treating urinary incontinence.

96. A method of treating male erectile dysfunction and premature ejaculation in a host mammal in need of such treatment comprising administering a therapeutically effective amount of a compound of claim 1.

97. A method of treating female anorgasmia, clitoral erectile insufficiency, vaginal engorgement, dyspareunia and vaginismus in a host mammal in need of such treatment comprising administering a therapeutically effective amount of a compound of claim 1.

* * * * *

UNITED STATES PATENT AND TRADEMARK OFFICE
CERTIFICATE OF CORRECTION

PATENT NO.    : 6,191,140 B1
DATED         : February 20, 2001
INVENTOR(S)   : William A. Carroll et al.

It is certified that error appears in the above-identified patent and that said Letters Patent is hereby corrected as shown below:

<u>Drawings,</u>
Figure 11,

Replace 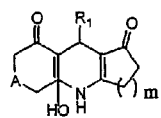 With 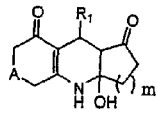

Figure 12

Replace 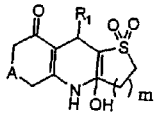 With 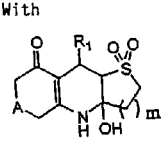

<u>Column 19,</u>
Line 17, replace "dihyrdopyridines" with -- dihydropyridines --.
Line 50, replace "$NaHB_4$" with -- $NaBH_4$ --.

<u>Column 20,</u>
Line 53, replace "ad" with -- as --.

<u>Column 25,</u>
Lines 26 and 27, replace "heminaminals" with -- hemiaminals --.

<u>Column 27,</u>
Line 39, replace "dihydrophyridines" with -- dihydropyridines --.

<u>Column 28,</u>
Line 56, replace "dihydropyridiens" with -- dihydropyridines --.

<u>Column 33,</u>
Line 47, replace "(81 using" with -- (81) using --.

<u>Column 36,</u>
Line 38, replace "tribluoroethane" with -- trifluoroethane --.

<u>Column 82,</u>
Line 55, replace "7H, 9H)" with -- (7H, 9H) --.

UNITED STATES PATENT AND TRADEMARK OFFICE
CERTIFICATE OF CORRECTION

PATENT NO.    : 6,191,140 B1
DATED         : February 20, 2001
INVENTOR(S)   : William A. Carroll et al.

It is certified that error appears in the above-identified patent and that said Letters Patent is hereby corrected as shown below:

Column 83,
Line 9, replace "7H, 9H)" with -- (7H, 9H) --.
Line 64, replace "3H, 4H)" with -- (3H,4H) --.

Column 84,
Line 25, replace "(+) 5-" with -- (+)-5- --.
Line 27, replace "(-) 5-" with -- (-)-5- --.

Column 86,
Line 65, replace "5H), 8H)" with -- (5H), 8H) --.

Column 87,
Line 40, replace "[3,4b]quinoline" with -- [3,4-b]quinoline --.

Column 89,
Line 7, replace "(+) 9" with -- (+)-9 --.
Line 10, replace "(-) 9" with -- (-)-9 --.
Line 11, replace "[3,4b]thieno" with -- [3,4-b]thieno --.

Signed and Sealed this

Twenty-sixth Day of August, 2003

JAMES E. ROGAN
*Director of the United States Patent and Trademark Office*